US007241461B2

(12) United States Patent
Myhill et al.

(10) Patent No.: US 7,241,461 B2
(45) Date of Patent: *Jul. 10, 2007

(54) COMPOSITIONS FOR ALLEVIATING INFLAMMATION AND OXIDATIVE STRESS IN A MAMMAL

(75) Inventors: Paul R. Myhill, Castle Rock, CO (US); William J. Driscoll, Englewood, CO (US)

(73) Assignee: Lifeline Nutraceuticals Corporation, Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/088,323

(22) Filed: Mar. 23, 2005

(65) Prior Publication Data

US 2005/0226942 A1 Oct. 13, 2005

Related U.S. Application Data

(60) Provisional application No. 60/646,707, filed on Jan. 25, 2005, provisional application No. 60/643,754, filed on Jan. 13, 2005, provisional application No. 60/610,749, filed on Sep. 17, 2004, provisional application No. 60/607,648, filed on Sep. 7, 2004, provisional application No. 60/604,638, filed on Aug. 26, 2004, provisional application No. 60/590,528, filed on Jul. 23, 2004, provisional application No. 60/555,802, filed on Mar. 23, 2004.

(51) Int. Cl.
*A61K 36/82* (2006.01)
*A61K 36/9066* (2006.01)

(52) U.S. Cl. .................. 424/729; 424/756; 424/725

(58) Field of Classification Search ............... None
See application file for complete search history.

(56) References Cited

U.S. PATENT DOCUMENTS

| 4,522,811 A | 6/1985 | Eppstein et al. |
| 5,854,287 A | 12/1998 | Weglicki |
| 5,939,395 A * | 8/1999 | Yu et al. .................. 514/23 |
| 6,093,404 A * | 7/2000 | Kattan ........................ 424/732 |
| 6,372,265 B2 * | 4/2002 | Saito ............................. 424/682 |
| 6,495,170 B1 | 12/2002 | Smit et al. |
| 6,646,013 B1 | 11/2003 | Barker et al. |
| 2002/0086067 A1 * | 7/2002 | Choi et al. .................. 424/729 |
| 2003/0072823 A1 | 4/2003 | Fleischner |

OTHER PUBLICATIONS

Albert, "The Role of C-Reactive Protein in Cardiovascular Disease Risk," *Curr. Cardio. Rep.*, 2000; vol. 2: pp. 274-279.
Alexandrakis, et al., "The Relation Between Bone Marrow Angiogenesis and the Proliferation Index Ki-67 in Multiple Myeloma," *J. Clin. Pathol.*, 2004; vol. 57: pp. 856-860.
Baeuerle, et al., "IκB: A Specific Inhibitor of the NF-κB Transcription Factor," *Science*, 1988; vol. 242: pp. 540-546.
Al-Shaer, "C-Reactive Protein and Risk of Colon Cancer," *JAMA*, 2004; vol. 291, No. 23: pp. 2818-2819.
Anderson, et al., "Differential Response of Human Ovarian Cancer Cells to Induction of Apoptosis by Vitamin E Succinate and Vitamin E Analogue, α-TEA," *Cancer Res.*, 2004; vol. 64: pp. 4263-4269.
Baker, et al., "Reduced RBC Versus Plasma Microvascular Flow Due to Endotoxin," *Circul. Shock*, 1986; vol. 20: pp. 127-139.
Barbosa, et al., "Decreased Oxidative Stress in Patients with Ulcerative Colitis Supplemented with Fish Oil ω-3 Fatty Acids," *Nutrition*, 2003; vol. 19: pp. 837-842.
Bhattacharya, et al., "Antioxidant Activity of Glycowithanolides from *Withania sominfera*," *Ind. J. Exper. Biol.*, 1997; vol. 35: pp. 236-239.
Bhattacharya, et al., "Antixidant Activity of *Bacopa monniera* in Rat Frontal Cortex, Striatum and Hippocampus," *Phytother. Res.*, 2000; vol. 14: pp. 174-179.
Bogarty, et al., "Biological Profiles in Subjects with Recurrent Acute Coronary Events Compared with Subjects with Long-standing Stable Angina," *Circulation*, 2001; vol. 103: pp. 3062-3068.
Bolibar, et al., "Short-term Prognostic Value of Lipid Measurements in Patients with Angina Pectoris," *Thromb. Haemost.*, 2000; vol. 84: pp. 955-960.
Bose, et al., "Membrane Lipid Peroxidation by UV-A: Mechanism and Implications," *Biotech. App. Biochem.*, 1990; vol. 12: pp. 557-561.
Boyd-Kimball, et al., "Rodent Aβ(1-42) Exhibits Oxidative Stress Properties Similar to Those of Human Aβ(1-42): Implications for Proposed Mechanisms of Toxicity," *J. Alzh. Dis.*, 2004; pp. 515-525.
Bridi, et al., "The Antioxidant Activity of Standardized Extract of *Ginkgo biloba* (EGb 761) in Rats," *Phytother. Res.*, 2001; vol. 15: pp. 449-451.
Chaudhri, et al., "Reactive Oxygen Species Facilitate the In Vitro an In Vivo Lipopolysaccharide-induced Release of Tumor Necrosis Factor," *J. Immun.*, 1989; vol., 142, No. 4; pp. 1290-1294.
Cole, et al., "Metal-catalyzed Oxidation of Alpha Synuclein: Helping to Define the Relationship Between Oligomers, Protofibrils and Filaments," *JBC Papers in Press*, Dec. 21, 2004; Man. M409946200.

(Continued)

*Primary Examiner*—Susan Hoffman
(74) *Attorney, Agent, or Firm*—Swanson & Bratschun, L.L.C.

(57) ABSTRACT

An antioxidant-promoting composition that increases antioxidant defense potential in a subject is disclosed comprising *Bacopa monniera* extract; milk thistle extract, ashwagandha powder, green tea extract, *Gotu kola* powder, *Ginko biloba* leaf extract; *Aloe vera* powder; turmeric extract; and N-acetyl cysteine. The antioxidant-promoting composition of the invention safely induces cellular antioxidant potential to achieve an overall net decrease in oxidative stress without the undesirable side-effects associated with the individual components of the antioxidant-promoting composition. Also disclosed is a method for reducing the undesirable side-effects of free radicals in a subject by administering to a subject in need of such antioxidants an effective amount of antioxidant-promoting composition of the invention.

3 Claims, 21 Drawing Sheets

OTHER PUBLICATIONS

Dawes, et al., "Rheumatoid Arthritis: Treatment which Controls the C-Reactive Protein and Erythrocyte Sedimentation Rate Reduces Radiological Progression," *Brit. J. Rheum.*, 1986; vol. 25: pp. 44-49.

Demopoulos, "The Basis of Free Radical Pathology," *Fed. Proc.*, 1973; vol. 32, No. 8: pp. 1859-1861.

Dessein, et al., "Cardiovascular Risk in Rheumatoid Arthritis Versus Osteoarthritis" Acute Phase Response Related Decreased Insulin Sensitivity and High-density Lipoprotein Cholesterol as well as Clustering of Metabolic Syndrome Features in Rheumatoid Arthritis, *Arthr. Res.*, 2002; vol. 4, No. R5: pp. 1-6.

Drash, et al., "Effect of Probucol on Development of Diabetes Mellitus in BB Rats," *Amer. J. Card.*,1988; vol. 62: pp. 27B-30B.

D'Souza, et al., "Brine Shrimp Lethality Assay of *Bacopa monnieri,*" *Phytother. Res.*, 2002; vol. 16: pp. 197-198.

Duh, et al., "Tumor Necrosis Factor α Activates Human Immunodeficiency Virus Type 1 Through Induction of Nuclear Factor Binding to the NF-κB Sites in the Long Terminal Repeat," *Proc. Natl. Acad. Sci. USA*, 1989; vol. 86: pp. 5974-5978.

Eck, et al., "Low Concentrations of Acid-Soluble Thiol (Cysteine) in the Blood Plasma of HIV-1 Infected Patients," *Biol. Chem.*, 1989; vol. 370: pp. 101-108.

Eck, et al., "Influence of the Extracellular Glutamate Concentration on the Intracellular Cyst(e)ine Concentration in Macrophages and on the Capacity to Release Cysteine," *Biol. Chem.*, 1989; vol. 370: pp. 109-113.

Hag, et al., "Immunomodulation by Neutrophil Myeloperoxidase and Hydrogen Peroxide: Differential Susceptibility of Human Lymphocyte Functions," *J. Immun.*, 1986; vol. 136, No. 9: pp. 3420-3426.

Fagan, et al., "Serum Levels of C-reactive Proteinin Crohn's Disease and Ulcerative Colitis," *Eur. J. Clin. Invest.*, 1982; vol. 12: pp. 351-359.

Fantone, et al., "Role of Oxygen-Derived Free Radicals and Metabolites in Leukocyte-dependent Inflammatory Reactions," *AJP*, 1982; vol. 107, No. 3: pp. 397-418.

Fischman, et al., "Inhibition of Lectin-induced Lymphocyte Activation by 2-Cyclohexene-1-One: Decreased Intracellular Glutathione Inhibits an Early Event in the Activation Sequence," *J. Immun.*, 1981; vol. 127, No. 6: pp. 2257-2262.

Fraser, et al., "Turnover of Type II Collagen and Aggrecan in Cartilage Matrix at the Onset of Inflammatory Arthritis in Humans," *Arth. Rheum.*, 2003; vol. 48, No. 11: pp. 3085-3095.

Hamanaka, et al., "Protoprotective Effect on Topically Applied Superoxide Dismutase on Sunburn Reaction in Comparison with Sunscreen," *J. Derm.*, 1990; vol. 17: pp. 595-598.

Haverkate, et al., "Haemostasis Factors in Angina Pectoris; Relation to Gender, AGen and Acute-Phase Reaction," *Thromb. Haemost.*, 1995; vol. 73, No. 4: pp. 561-567.

Hebbel, et al., "Spontaneous Oxygen Radical Generation by Sickle Erythrocytes," *J. Clin. Invest.*, 1982; vol. 70: pp. 1253-1259.

Hernandez, et al., "Calcium Antagonists and Atherosclerosis Protection in Hypertension," *Amer. J. Therap.*, 2003; vol. 10: pp. 409-414.

Machiedo, et al., "Temporal Relationship of Hepatocellular Dysfunction and Ischemia in Sepsis," *Arch. Surg.*, 1988; vol. 123: pp. 424-427.

Kalebic, et al., "Suppression of Human Immunodeficiency Virus Expression in Chronically Infected Monocytic Cells by Glutathione, Glutathione Ester, and N-acetylcysteine," *Proc. Natl. Acad. Sci. USA*, 1991; vol. 88: pp. 986-990.

Kar, et al., "Relative Efficacy of Three Medicinal Plant Extracts in the Lateration of Thyroid Hormone Concentrations in Male Mice," *J. Ethnopharm.*, 2002; vol. 81: pp. 281-285.

Kline, et al., "Vitamin E and Breast Cancer," *J. Nutr.* 2004; vol. 134: pp. 3458S-3462S.

Koenig, et al., "C-Reactive Protein, a Sensitive Marker of Inflammation, Predicts Future Risk of Coronary Heart Disease in Initially Healthy Middle-Aged Men," *Circulation*, 1999; vol. 99: pp. 237-242.

Kraut, et al., "The Effect of Oxidant Injury on the Lymphocyte Membrane and Functions," *J. Lab. Clin. Med.*, 1981; vol. 98: pp. 697-703.

Lenzen, et al., "Low Antioxidant Enzyme Gene Expression in Pancreatic Islets Compared with Various Other Mouse Tissues," *Free Rad. Bio. Med.*, 1996; vol. 20, No. 3: pp. 463-466.

Li, et al., "Is Hypertension an Inflammatory Disease?" *Med. Hyp.*, 2005; vol. 64: pp. 236-240.

Lipsky, "Immunosuppression by D-Penicillamine in Vitro," *J. Clin. Invest.*, 1984; vol. 73: pp. 53-65.

Luczaj, et al., "Green Tea Protection Against Age-Dependent Ethanol-Induced Oxidative Stress," *J. Tox. Envir. H., Part A.*, 2004; vol. 67: pp. 595-606.

Massey, et al., "α-Tocopherol Attenuates Myocardial Membrane-Related Alterations Resulting from Ischemia and Reperfusion," *Am. J. Physiol.*, 1989; vol. 256 (Heart Circ. Physiol. 25): pp. H1192-H1199.

McArdle, et al., "The Relationship Between Interleukin-6 and C-Reactive Protein in Patients with Benign and Malignant Prostate Disease," *Br. J. Canc.*, 2004; vol. 91: pp. 1755-1757.

McCord, "Free Radicals and Myocardial Ischemia: Overview and Outlook," *Free Rad. Bio. Med.*, 1988; vol. 4: pp. 9-17.

McCord, et al., "Superoxide Dismutase; an Enzymic Function for Erythrocuprein (Hemocuprein)," *J. Bio. Chem.*, 1969; vol. 244, No. 22: pp. 6049-6055.

McKechnie, et al., "Modification by Oxygen Free Radical Scavengers of the Metabolic and Cardiovascular Effects of Endotoxin Infusion in Conscious Rats," *Cir. Sh.*, 1986; vol. 19: pp. 429-439.

McKeown, et al., "The Relationship Between Circulating Concentrations of C-reactive Protein, Inflammatory Cytokines and Cytokine Receptors in Patients with Non-Small-Cell Lung Cancer,", *Br. J. Can.*, 2004; vol. 91: pp. 1993-1995.

Morrow, et al., "C-Reactive Protein is a Potent Predictor of Mortality Independently of and in Combination With Troponin T in Acute Coronary Syndromes: A TIMI 11A Substudy," *JACC*, 1998; vol. 31, No. 7: pp. 1460-1465.

Moukarbel, et al., "C-Reactive Protein is a Marker for a Complex Culprit Lesion Anatomy in Unstable Angina," *Clin. Cardiol.*, 2001; vol. 24: pp. 506-510.

Nomikos, et al., "Brief Communication Involvement of $O_2$ radicals in 'autoimmune' diabetes," *Immunol. Cell Biol.* 1989; vol. 67 pp. 85-87.

Pasaoglu, et al., "Lipid Peroxidation and Resistance to Oxidation in Patients with Type 2 Diabetes Mellitus," *Toh. J. Exp. Med.*, 2004; vol. 203: pp. 211-218.

Pauling, "Vitamin C Therapy of Advanced Cancer," *NE. J. of Med.*, 1980; vol. 302, No. 12: pp. 694-695.

Pelle, et al., "An in Vitro Model to Test Relative Antioxidant Potential: Ultraviolet-Induced Lipid Peroxidation in Liposomes," *Arch. of Biochem. and Biophys.*, 1990; vol. 283, No. 2: pp. 234-240.

Rabinovitch, et al., "Human Pancreatic Islet β-Cell Destruction by Cytokines Involves Oxygen Free Radicals and Aldehyde Production," *J. of Clin. Endo. and Metab.*, 1996; vol. 81, No. 9: pp. 3197-3202.

Puapairoj, et al., "Effect of Ethanol on Paraquat Toxicity in F344 Rats," *Fd Chem. Toxic.*, 1994; vol. 32, No. 4: pp. 379-386.

Rifai, et al., "High-Sensitivity C-Reactive Protein: A Novel and Promising Marker of Coronary Heart Disease," *Clin. Chem.*, 2001; vol. 47, No. 3: pp. 403-411.

Roederer, et al., "Cytokine-stimulated human immunodeficiency virus replication is inhibited by N-acetyl-L-cysteine." *Proc. Natl. Acad. Sci. USA*, 1990; vol. 87: pp. 4884-4888.

Greenwald, "C-Reactive Protein Elevation and the Risk of Colorectal Cancer," *Gastroent. Nur.*, 2004; vol. 27, No. 5: pp. 246-247.

Sager, et al., "Oxygen Free Radicals in Essential Hypertension," *Mol. &Cell. Biochem.*, 1992; vol. 111: pp. 103-108.

Schiffrin, "Vascular Stiffening and Arterial Compliance: Implications for Systolic Blood Pressure," *AJH*, 2004; vol. 17: pp. 39S-48S.

Singh, et al., "Chemomodulatory Action of *Aloe vera* on the Profiles of Enzymes Associated with Carcinogen Metabolism and Antioxidant Status Regulation in Mice," *Phytomedicine*, 2000; vol. 7, No. 3: pp. 209-219.

Skrzydlewska, et al., "Lipid Peroxidation and Antioxidant Status in Colorectal Cancer," *World J. Gastroent.*, 2005; vol. 11, No. 3: pp. 403-406.

Shukla, et al., "Asiaticoside-induced Elevation of Antioxidant Levels in Healing Wounds," *Phytother. Res.*, 1999; vol. 13: pp. 50-54.

Soto, et al., "Silymarin Increases Antiodixdant Enzymes In Alloxan-Induced Diabetes In Rat Pancreas," *Comp. Biochem. Phys.*, 2003; Part C, vol. 136: pp. 205-212.

Sowers, et al., "C-Reactive Protein as a Biomarker of Emergent Osteoarthritis," *Osteoarth. Cart.*, 2002; vol. 10: pp. 595-601.

Staal, et al., "Intracellular Thiols Regulate Activation of Nuclear Factor κB and Transcription of Human Immunodeficiency Virus," *Pro. Natl. Acad. Sci. USA*, 1990; vol. 87: pp. 9943-9947.

Ungvari, et al., "Vascular Inflammation in Aging," *Hertz*, 2004; vol. 29, No. 8: pp. 733-740.

Sturmer, et al., "Severity And Extent Of Osteoarthritis And Low Grade Systemic Inflammation As Assessed By High Sensitivity C Reaction Protein," *Ann Rhuem Dis*, 2004; vol. 63: pp. 200-205.

Swei, et al., "Mechanisms of Oxygen Free Radical Formation in Experimental Forms of Hypertension," *On-line Proceedings of the 5th Internet World Congress on Biomedical Sciences '98 at McMaster University, Canada*, Presentation No. SAswei0837, 1998.

Tabatabaie, et al., "Spin Trapping Agent Phenyl N-*tert*-butylnitrone Protects Against the Onset of Drug-Induced Insulin-Dependent Diabetes Mellitus," *FEBS*, 1997; vol. 407: 148-152.

Till, et al., "Role of Xanthine Oxidase in Thermal Injury of Skin," *Amer. J. of Patho.*, 1989, vol. 135, No. 1: pp. 195-202.

Vincent, et al., "Oxidative Stress in the Pathogenesis of Diabetic Neuropathy," *Endo. Rev.*, 2004; vol. 25, No. 4: pp. 612-628.

Walter, et al., "Serum Levels of Thiobarbituric Acid Reactive Substances Predict Cardiovascular Events in Patients With Stable Coronary Artery Disease: A Longitudinal Analysis of the PREVENT Study," *J. Amer. Col. Cardio. Fd.*, 2004; vol. 44, No. 10: pp. 1996-2002.

Wang, et al., "Effect of C-Reactive Protein on Gene Expression in Vascular Endothelial Cells," *Am. J. Physiol. Heart Circ. Physiol.*, 2005; vol. 288: pp. H1539-H1545.

Weiss, "The Role of Superoxide in the Destruction of Erythrocyte Targets by Human Neutrophils," *J. of Biol. Chem.*, 1980; vol. 255, No. 20: pp. 9912-9917.

Guohua, et al., "Expression of C5aR (CD88) Of Synoviocytes Isolated From Patients With Rheumatoid Arthritis and Osteoarthritis," *Chin. Me. J.*, 2003; vol. 116, No. 9: pp. 1408-1412.

Niwa, "Lipid Peroxides and Superoxide Dismutase (SOD) Induction in Skin Inflammatory Diseases, and Treatment with SOD Preparations," *Dermatologica*, 1989; vol. 179: pp. 101-106.

Zweier, et al., "Direct Measurement of Free Radical Generation Following Reperfusion of Ischemic Myocardium," *Proc. Natl. Acad. Sci. USA*, 1987; vol. 84: pp. 1404-1407.

Reddy and Lokesh (1994) Food and Chemical Toxicology 32(3):279-283.

Chen et al., Protective effects of silybin and tetrandrine on the outcome of spontaneously hypertensive rats subjected to acute coronary artery occlusion, (1993) International Journal of Cardiology 41:103-108.

Falchi et al., Effects of Silymarin on Platelet Aggregation in Hypercholesterolaemised Rabbits, (1983) Drugs Exptl. Clin. Res. IX(6):419-422.

Tripathi et al., *Bacopa monniera* Linn. as an antioxidant: Mechanism of action, (Jun. 1996) Indian Journal of Experimental Biology, 34:523-526.

* cited by examiner

A

B

COMPOSITIONS FOR ALLEVIATING INFLAMMATION AND OXIDATIVE STRESS IN A MAMMAL

RELATED APPLICATIONS

This application is claims the benefit of priority under 35 U.S.C. §120 from U.S. Ser. No. 60/555,802, filed on Mar. 23, 2004; U.S. Ser. No. 60/590,528, filed on Jul. 23, 2004; U.S. Ser. No. 60/604,638, filed on Aug. 26, 2004; U.S. Ser. No. 60/607,648, filed on Sep. 7, 2004; U.S. Ser. No. 60/610,749, filed on Sep. 17, 2004; U.S. Ser. No. 60/643,754, filed on Jan. 13, 2005, and U.S. Ser. No. 60/646,707, filed on Jan. 25, 2005, the contents of which are incorporated herein by reference in their entireties.

FIELD OF THE INVENTION

The present invention relates to compositions for alleviating inflammation and oxidative stress in a subject. Specifically, the present invention is directed to the field of natural remedies and the development of compositions to increase the antioxidant potential of a subject by inducing the subject's natural cellular defenses.

DESCRIPTION OF THE INVENTION

Free radicals have come to be appreciated for their importance to human health and disease. Many common and life-threatening diseases, including atherosclerosis, cancer, and aging, have free radical reactions as an underlying mechanism of injury. One of the most common types of radicals is the reactive oxygen species (ROS). These are the products of normal cell respiration and metabolism and are generally regulated by cellular defense systems present in the body. Such cellular defense systems reduce the amount of damage that free and reactive species radicals may cause by scavenging free radicals or enzymatically converting the free radicals to less toxic chemical species, thereby serving a physiological role as antioxidants.

Superoxide dismutase (SOD), catalase (CAT), and glutathione peroxidase (GPX) are three mammalian enzymes important to cellular defense against ROS-mediated cellular damage. Due to environmental agents such as pollution, and lifestyle factors such as smoking or exercising, the cellular exposure to free radicals is increased. Such increase may bring the body out of balance, especially as the body ages and the mechanisms that produce antioxidants or remove ROS are insufficient to counter oxidative stress. The body's antioxidant defense system(s), including SOD, CAT, and GPX, can be impaired by the aging process and or compromised, for example, by inflammation, microbial infection, viral infection, the progression of cancer or neurological disorders, and many other disorders characterized by or caused in part by oxidative stress. The resulting damage can range from disruption of biological processes, killing of cells, and mutation of genetic material, which may lead to the occurrence of cancer. Accordingly, the potential use of antioxidant containing dietary supplements for protection against the effects of oxidative stress and the progression of degenerative diseases and aging has been the subject of an increasing number of studies during the past four decades, see for example, Pauling L., N Engl J. Med., Vitamin C therapy of advanced cancer, Mar. 20, 1980; 302(12):694-5.

Non-enzymatic antioxidants can react with free radicals directly and become self-oxidized (therefore no longer available to quench free radicals); or one antioxidant may act as a reducing agent and another antioxidant oxidized in cyclical fashion (e.g., the interaction of ascorbic acid and alpha-tocopherol). Other non-enzymatic free radical scavengers have been used experimentally with varying results (e.g. mannitol, PBS, etc.); their clinical use is severely limited due to their toxicities. Other synthetic antioxidants, e.g., BHA (butylated hydroxy anisole), BHT (butylated hydroxy toluene) and NDGA (nordihydro guaiaretic acid) may cause allergic reactions and oncogenesis due to their strong toxicity in the body, and be easily disrupted by heat due to temperature sensitivity.

Enzymatic antioxidants (e.g., SOD, CAT and GPX), on the other hand, are not consumed in the reactions with free radicals, although they can be damaged under pathological conditions and consequently rendered non-functional. In the local cellular milieu, damaged enzymatic antioxidants would render that cellular environment compromised and subject to free radical attack. The disadvantage of administering enzymatic antioxidants to humans is (1) the possibility of allergic reactions (in the case of a bacterial or fungal derived enzyme) of varying degrees of severity; (2) the great cost of harvesting these enzymes; (3) the limitation of quantities of enzymatic antioxidants able to be administered at a given time (theoretically to avoid side-effects such as serum sickness or other immune reaction to the recombinant protein); (4) they serve a singular purpose (i.e., they react with only one type of oxidant); and (5) they do not quench all radicals, that may be important for beneficial metabolic pathways, e.g., nitric oxide induced vasodilation and immune system support (see, e.g., Griscavage J M, Wilk S, Ignarro L J., Proc Natl Acad Sci USA., Inhibitors of the proteasome pathway interfere with induction of nitric oxide synthase in macrophages by blocking activation of transcription factor NF-kappa B., Apr. 16, 1996; 93(8):3308-12.

The efficacy of direct oral administration of SOD, CAT, or GPX has been limited by the sensitivity of these enzymes to the milieu of the digestive system and/or lack of bioavailability. For example, research indicated that the digestive system destroyed SOD, and that neither CAT nor GPX was absorbed via the digestive tract.

Since administration by direct ingestion of the antioxidants showed disappointing results, efforts have been directed to provide the body with the so-called "building blocks" of each of the three antioxidants. A promising approach has been the development of compositions directed toward increasing the activities of SOD, CAT, and GPX in the body. Accordingly, supplements have been formulated to increase levels of the body's zinc, copper, and manganese, to assist the body's production of SOD. Similarly, iron, selenium, and glutathione related supplements have been developed to increase CAT and GPX. These compounds have toxic effects in large quantities.

SUMMARY OF THE INVENTION

The present invention provides compositions that can be administered to a mammalian subject, and will safely induce in the subject, increased antioxidant potential in the subject by increasing the activity of at least one antioxidant enzyme which include, e.g., SOD, CAT, and GPX, and thereby decreasing the tissue level of pathologic free radical species. The compositions of the present invention yield an overall net decrease in oxidative stress and inflammation when administered to a mammalian subject in an effective amount with minimal undesirable side-effects. Advantageously, the compositions of the invention provides fewer side effects than may be associated with each of the individual active agents in the composition.

In one aspect, the invention provides an antioxidant-promoting composition that comprises active ingredients comprising at least two agents that include, e.g., *Bacopa monniera* extract; milk thistle extract, ashwagandha powder, green tea extract, *Gotu kola* powder, *Ginko biloba* leaf extract; *Aloe vera* powder; turmeric extract; and N-acetyl cysteine, wherein the composition increases the enzyme activity level of at least one antioxidant enzyme, e.g., superoxide dismutase; catalase; and glutathione peroxidase and decreases the plasma concentration level of thiobarbituric acid reactive chemical species, when administered in an effective amount to a mammalian subject in need thereof. In one embodiment, the *Bacopa monniera* extract is standardized extract prepared from the leaves of the *Bacopa monniera* plant. In one embodiment, the *Bacopa monniera* standardized extract contains at least 20% bacosides. In one embodiment, the *Bacopa monniera* extract is present at a concentration of about 5 weight percent to about 50 weight percent of the total dry weight of active ingredients of the composition. In one embodiment, the *Bacopa monniera* extract is present at a concentration of about 10 weight percent to about 30 weight percent of the total dry weight of active ingredients of the composition. In one embodiment, the *Bacopa monniera* extract is present at a concentration at least about 22 weight percent of the total dry weight of active ingredients of the composition. In one embodiment, *Bacopa monniera* extract is present at a concentration at least about 12 weight percent of the total dry weight of active ingredients of the composition. In one embodiment, the milk thistle extract is standardized to contain at least about 70 weight percent silymarin. In one embodiment, the milk thistle extract is present at a concentration from about 5 weight percent to about 60 weight percent of the total dry weight of active ingredients of the composition. In one embodiment, the milk thistle extract is present at a concentration from about 10 weight percent to about 50 weight percent of the total dry weight of active ingredients of the composition. In one embodiment, the milk thistle extract is present at a concentration at least about 33 weight percent of the total dry weight of active ingredients of the composition. In one embodiment, the milk thistle extract is present at a concentration at least about 22 weight percent of the total dry weight of active ingredients of the composition. In one embodiment, the ashwagandha powder is present at a concentration from about 5 weight percent to about 50 weight percent of the total dry weight of active ingredients of the composition. In one embodiment, the ashwagandha powder is present at a concentration from about 10 weight percent to about 30 weight percent of the total dry weight of active ingredients of the composition. In one embodiment, the ashwagandha powder is present at a concentration at least about 22 weight percent of the total dry weight of active ingredients of the composition. In one embodiment, the ashwagandha powder is present at a concentration at least about 12 weight percent of the total dry weight of active ingredients of the composition. In one embodiment, the turmeric extract is standardized to contain at least about 95 weight percent curcumin. In one embodiment, turmeric extract is present at a concentration from about 2.5 weight percent to about 25 weight percent of the total dry weight of active ingredients of the composition. In one embodiment, the turmeric extract is present at a concentration from about 5 weight percent to about 15 weight percent of the total dry weight of active ingredients of the composition. In one embodiment, the turmeric extract is present at a concentration at least about 11 weight percent of the total dry weight of active ingredients of the composition. In one embodiment, the turmeric extract is present at a concentration at least about 6 weight percent of the total dry weight of active ingredients of the composition. In one embodiment, the green tea extract is standardized to contain at least about 40% polyphenols. In one embodiment, the at least one polyphenol is polyphenol (–)-epigallocatechin gallate. In one embodiment, the green tea extract is present at a concentration from about 2.5 weight percent to about 25 weight percent of the total dry weight of active ingredients of the composition. In one embodiment, the green tea extract is present at a concentration from about 5 weight percent to about 15 weight percent of the total dry weight of active ingredients of the composition. In one embodiment, the green tea extract is present at a concentration at least about 11 weight percent of the total dry weight of active ingredients of the composition. In one embodiment, the green tea extract is present at a concentration at least about 6 weight percent of the total dry weight of active ingredients of the composition. In one embodiment, the *Gotu kola* powder is present at a concentration from at least about 5 weight percent to about 50 weight percent of the total dry weight of active ingredients of the composition. In one embodiment, the *Gotu kola* powder is present at a concentration from at least about 10 weight percent to about 30 weight percent of the total dry weight of active ingredients of the composition. In one embodiment, the *Gotu kola* extract is present at a concentration at least about 12 weight percent of the total dry weight of active ingredients of the composition. In one embodiment, the *Ginko biloba* leaf extract is present at a concentration from at least about 5 weight percent to about 50 weight percent of the total dry weight of active ingredients of the composition. In one embodiment, the *Ginko biloba* leaf extract is present at a concentration from at least about 10 weight percent to about 30 weight percent of the total dry weight of active ingredients of the composition. In one embodiment, the *Ginko biloba* leaf extract is present at a concentration at least about 12 weight percent of the total dry weight of active ingredients of the composition. In one embodiment, the *Aloe vera* powder is present at a concentration from at least about 5 weight percent to about 50 weight percent of the total dry weight of active ingredients of the composition. In one embodiment, the *Aloe vera* powder is present at a concentration from at least about 10 weight percent to about 30 weight percent of the total dry weight of active ingredients of the composition. In one embodiment, the *Aloe vera* powder is present at a concentration at least about 12 weight percent of the total dry weight of active ingredients of the composition. In one embodiment, the N-acetyl cysteine is present at a concentration of about 2 weight percent to about 20 weight percent of the total dry weight of active ingredients of the composition. In one embodiment, the N-acetyl cyteine is present at a concentration of about 5 weight percent to about 15 weight percent of the total dry weight of active ingredients of the composition. In one embodiment, the N-acety cysteine is present at a concentration of at least about 6 weight percent of the total dry weight of active ingredients of the composition.

In one embodiment, the composition of the invention contains at least two (2) of the active ingredients of the antioxidant-promoting composition. In one embodiment, the composition of the invention contains at least three (3) of the active ingredients of the antioxidant-promoting composition. In one embodiment, the composition of the invention contains at least four (4) of the active ingredients of the antioxidant-promoting composition. In one embodiment, the composition of the invention contains at least five (5) of the active ingredients of the antioxidant-promoting composition. In one embodiment, the composition of the invention contains at least six (6) of the active ingredients of the antioxidant-promoting composition. In one embodiment, the composition of the invention contains at least seven (7) of the active ingredients of the antioxidant-promoting composition. In one embodiment, the composition of the invention contains at least eight (8) of the active ingredients of the antioxidant-promoting composition. In one embodiment, the composition of the invention contains at least nine (9) of the active ingredients of the antioxidant-promoting composition.

In another embodiment, the composition of the invention is an antioxidant-promoting composition comprising active ingredients comprising *Bacopa monniera* extract; milk thistle extract, ashwagandha powder, green tea extract, and turmeric extract, wherein the composition increases the enzyme activity level of at least one antioxidant enzyme, e.g., superoxide dismutase; catalase; and glutathione peroxidase and decreases the plasma concentration level of thiobarbituric acid reactive chemical species, when administered in an effective amount to a mammalian subject in need thereof. In one embodiment, the *Bacopa monniera* extract is a standardized extract prepared from the leaves of the *Bacopa monniera* plant. In one embodiment, the standardized *Bacopa monniera* extract contains at least 20% bacosides. In one embodiment, the *Bacopa monniera* extract is present at a concentration of about 5 weight percent to about 50 weight percent of the total dry weight of active ingredients of the composition. In one embodiment, the *Bacopa monniera* extract is present at a concentration of about 10 weight percent to about 30 weight percent of the total dry weight of active ingredients of the composition. In one embodiment, the *Bacopa monniera* extract is present at a concentration at least about 22 weight percent of the total dry weight of active ingredients of the composition. In one embodiment, the *Bacopa monniera* extract is present at a concentration at least about 12 weight percent of the total dry weight of active ingredients of the composition. In one embodiment, the milk thistle extract is standardized to contain at least about 70 weight percent silymarin. In one embodiment, the milk thistle extract is present at a concentration from about 5 weight percent to about 60 weight percent of the total dry weight of active ingredients of the composition. In one embodiment, the milk thistle extract is present at a concentration from about 10 weight percent to about 50 weight percent of the total dry weight of active ingredients of the composition. In one embodiment, the milk thistle extract is present at a concentration at least about 33 weight percent of the total dry weight of active ingredients of the composition. In one embodiment, the milk thistle extract is present at a concentration at least about 22 weight percent of the total dry weight of active ingredients of the composition. In one embodiment, the ashwagandha powder is present at a concentration from about 5 weight percent to about 50 weight percent of the total dry weight of active ingredients of the composition. In one embodiment, the ashwagandha powder is present at a concentration from about 10 weight percent to about 30 weight percent of the total dry weight of active ingredients of the composition. In one embodiment, the ashwagandha powder is present at a concentration at least about 22 weight percent of the total dry weight of active ingredients of the composition. In one embodiment, the ashwagandha powder is present at a concentration at least about 12 weight percent of the total dry weight of active ingredients of the composition. In one embodiment, the turmeric extract is standardized to contain at least about 95 weight percent curcumin. In one embodiment, the turmeric extract is present at a concentration from about 2.5 weight percent to about 25 weight percent of the total dry weight of active ingredients of the composition. In one embodiment, the turmeric extract is present at a concentration from about 5 weight percent to about 15 weight percent of the total dry weight of active ingredients of the composition. In one embodiment, the turmeric extract is present at a concentration at least about 11 weight percent of the total dry weight of active ingredients of the composition. In one embodiment, the turmeric extract is present at a concentration at least about 6 weight percent of the total dry weight of active ingredients of the composition. In one embodiment, the green tea extract is standardized to contain at least about 40% polyphenols. In one embodiment, at least one polyphenol is polyphenol (–)-epigallocatechin gallate. In one embodiment, the green tea extract is present at a concentration from about 2.5 weight percent to about 25 weight percent of the total dry weight of active ingredients of the composition. In one embodiment, the green tea extract is present at a concentration from about 5 weight percent to about 15 weight percent of the total dry weight of active ingredients of the composition. In one embodiment, the green tea extract is present at a concentration at least about 11 weight percent of the total dry weight of active ingredients of the composition. In one embodiment, the green tea extract is present at a concentration at least about 6 weight percent of the total dry weight of active ingredients of the composition. In one embodiment, the composition further comprises the active ingredients *Gotu kola* powder, *Ginko biloba* leaf extract and *Aloe vera* powder. In one embodiment, the *Gotu kola* powder is present at a concentration from at least about 5 weight percent to about 50 weight percent of the total dry weight of active ingredients of the composition. In one embodiment, the *Gotu kola* powder is present at a concentration from at least about 10 weight percent to about 30 weight percent of the total dry weight of active ingredients of the composition. In one embodiment, the *Gotu kola* powder extract is present at a concentration at least about 12 weight percent of the total dry weight of active ingredients of the composition. In one embodiment, the *Ginko biloba* leaf extract is present at a concentration from at least about 5 weight percent to about 50 weight percent of the total dry weight of active ingredients of the composition. In one embodiment, the *Ginko biloba* leaf extract is present at a concentration from at least about 10 weight percent to about 30 weight percent of the total dry weight of active ingredients of the composition. In one embodiment, the *Ginko biloba* leaf extract is present at a concentration at least about 12 weight percent of the total dry weight of active ingredients of the composition. In one embodiment, the *Aloe vera* powder is present at a concentration from at least about 5 weight percent to about 50 weight percent of the total dry weight of active ingredients of the composition. In one embodiment, the *Aloe vera* powder is present at a concentration from at least about 10 weight percent to about 30 weight percent of the total dry weight of active ingredients of the composition. In one embodiment, the *Aloe vera* powder is present at a concentration at least about 12 weight percent of the total dry weight of active ingredients of the composition.

In some embodiments, the compositions of the present invention further comprise at least one excipient, e.g., calcium carbonate; croscarmellose sodium; dicalcium phosphate; magnesium stearate; microcrystalline cellulose; modified cellulose; silica; and stearic acid.

In another embodiment the invention provides an antioxidant-promoting composition comprising: (a) active ingredients comprising at least about 150 milligrams *Bacopa monniera*, extract 45 percent bacosides; at least about 225 milligrams milk thistle extract, between about 70 percent and about 80 percent silymarin; at least about 150 mg ashwagandha powder; at least about 75 milligrams green tea extract; 98 percent polyphenols; 45 percent (−)-epigallocatechin gallate; at least about 75 milligrams turmeric extract; 95 percent curcumin; and (b) other ingredients comprising calcium carbonate; croscarmellose sodium; dicalcium phosphate; magnesium stearate; microcrystalline cellulose; modified cellulose; silica; and stearic acid; wherein the composition increases the enzyme activity level of at least one antioxidant enzyme selected from the group consisting of: superoxide dismutase; catalase; and glutathione peroxidase and decreases the plasma concentration level of thiobarbituric acid reactive chemical species, when administered in an effective amount to a mammalian subject in need thereof. In one embodiment, the composition is formulated as an oral dosage form. In one embodiment, the oral dosage form is selected from the group consisting of: a tablet; capsule; and caplet.

In another aspect the invention provides a method of increasing the antioxidant activity level of a mammalian subject in need thereof, by increasing the level of enzyme activity of at least one enzyme, e.g., superoxide dismutase; catalase; and glutathione peroxidase, by administering to the subject an effective amount of an antioxidant-promoting composition of the invention, wherein the increased enzyme activity decreases the tissue damage caused by pathological free radicals. In one embodiment, the tissue damage caused by pathological free radicals occurs in a mammalian subject with a disease or condition selected from the group which includes, e.g., inflammation; infection; atherosclerosis; hypertension; cancer; radiation injury; neurological disease; neurodegenerative disease; ischemia/reperfusion injury; aging; wound healing; glutathione deficiency; acquired immunodeficiency syndrome; sickle cell anemia; and diabetes mellitus. In one embodiment of the method, the antioxidant-promoting composition is administered as an oral dietary supplement.

In one embodiment, the invention provides a method of reducing the plasma level of c-reactive protein in a mammalian subject, by administering to the subject an effective amount of an antioxidant-promoting composition of the invention. In one embodiment of the method, the antioxidant-promoting composition is administered as an oral dietary supplement. In one embodiment of the method, the plasma level of c-reactive protein decreases by at least 10% or more in a 30 day period. In one embodiment of the method, the plasma level of c-reactive protein decreases by at least 20% or more in a 30 day period.

In one embodiment, the invention provides a method of reducing the blood pressure in a mammalian subject, by administering to the subject an effective amount of an antioxidant-promoting composition of the invention. In one embodiment of the method, the antioxidant-promoting composition is administered as an oral dietary supplement.

The compositions of the present invention are useful to promote healthful benefits as follows: relaxation; bone marrow and women's health (e.g., stabilizes fetus and regenerates hormones); mental function (e.g., memory and concentration); sexual function; diuretic; anti-inflammatory; anti-mutagenic agent; anti-cancer agent; cholagogueue; depurative; fumitory; hemostatic agent; hepatoprotective agent; lactagogue; stomachic; tonic; vulnerary; tissue healing (e.g.; wounds; skin; other connective tissues; lymph tissue; blood vessels; and mucous membranes); remove free radicals in the peripheral and/or cerebral vascular systems; and inhibit lipid peroxidation; improve cerebral blood circulation and to protect the nerves against damaging free radicals; protective against cell damage caused by chemotherapy and radiation therapy; to enhance immune function; and to protect against toxins (e.g., acetametaphen and other drugs; mercury; lead).

The compositions of the present invention are useful to prevent or treat the following disorders and diseases: memory loss; Parkinson's disease; aging; toxin-induced hepatotoxicity; inflammation; liver cirrhosis; chronic hepatitis; and diabetes due to cirrhosis; indigestion; fatigue; stress; cough; infertility; tissue inflammation; cancer; anxiety disorders; panic attacks; rheumatism; pain; manic depression; alcoholic paranoia; schizophrenia; fever; insomnia; infertility; aging; skin inflammations and disorders; alcoholism; anemia; carbuncles; convalescence; emaciation; HIV; AIDS; immune system problems; lumbago; multiple sclerosis; muscle energy loss; paralysis; swollen glands; ulcers; breathing difficulties; inflammation; psoriasis; cancer (e.g.; prostate cancer, lung cancer and breast cancer); pain; cardiovascular disease (e.g.; arteriosclerosis and atherosclerosis); ischemia/reperfusion injury; anxiety; attention deficit disorder; leprosy; arthritis (e.g., psoriatic arthritis; anklylosing spondvlitis; and rheumatoid arthritis); hemorrhoids; tuberculosis; high blood pressure; congestive heart failure; venous insufficiency (pooling of blood in the veins; usually in the legs); sore throat; hepatitis; syphilis; stomach ulcers; epilepsy; diarrhea; asthma; burns; piles; sunburn; wrinkles; headache; insect bites; cuts; ulcers; sores; herpes; jaundice; bursitis; canker sores; sore gums; poison ivy; gastritis; high cholesterol; heart disease; bacterial infection; viral infection; acne; aging; immune disorders; dental caries; periodontitis; halitosis; dandruff; cardiovascular disease (e.g., hypertension; thrombosis; arteriosclerosis); migraine headaches, diabetes; elevated blood glucose; diseases of the alimentary canal and respiratory system; age-related physical and mental deterioration (e.g., Alzheimer's Disease and age-related dementia); cardiovascular disease; cerebral vascular insufficiency and impaired cerebral performance; congestive symptoms of premenstrual syndrome; allergies; age-related vision loss; depression; Raynaud's disease; peripheral vascular disease; intermittent claudication; vertigo; equilibrium disorder; prevention of altitude sickness; tinnitus (ringing in the ear); liver fibrosis; macular degeneration; asthma; graft rejection; and immune disorders that induce toxic shock; bronchoulmonary disease as cystic fibrosis; chronic bronchitis; gastritis; heart attack; angina pectoris; chronic obstructive pulmonary disease; kidney damage during coronary angiography; Unverricht-Lundborg disease; pseudoporphyria; pneumonia; and paracetamol hepatotoxicity

DETAILED DESCRIPTION OF THE INVENTION

Figure 1:
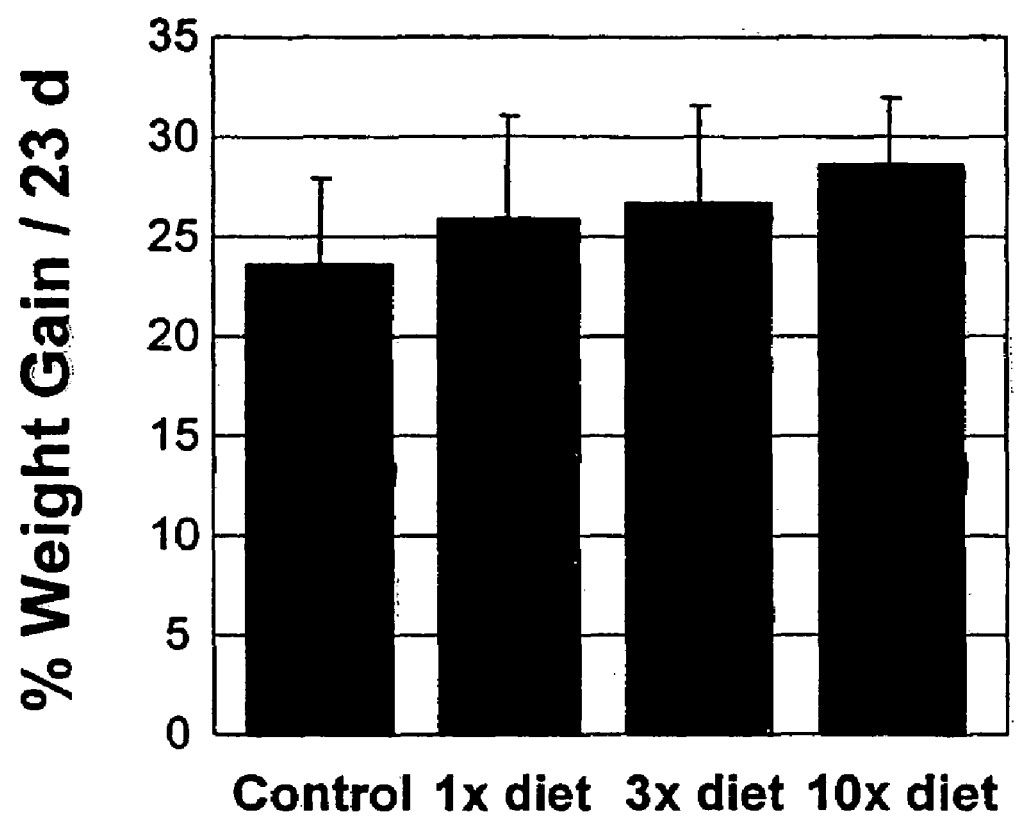
FIG. 1 is a graph illustrating effect of Protandim I dietary supplementation on percent weight gain of mice after 23 days.

There remains a need to formulate improved compositions and supplements that increase the SOD, CAT, or GPX levels in a mammal, that may be more effective and have fewer side-effects and lowered toxicity. The present invention provides compositions that can be administered to a mammalian subject, and will safely induce in the subject, increased antioxidant potential in the subject by increasing the activity of at least one antioxidant enzyme which include, e.g., SOD, CAT, and GPX, and thereby decreasing the tissue level of pathologic free radical species. The composition provides for an overall net decrease in oxidative stress experienced by the mammal, with minimal undesirable side-effects. Advantageously, the composition itself provides fewer side effects than may be associated with each of the individual active agents in the composition.

Accordingly, the various aspects of the present invention relate to therapeutic or prophylactic uses of certain particular compositions (e.g., dietary supplement compositions) in order to prevent or treat a disease or an injury induced by pathological free and reactive radical reactions. The various aspects of the present invention further relate to therapeutic or prophylactic uses of certain particular compositions in order to prevent or treat a disease or an injury associated with decreased SOD, CAT, and/or GPX enzyme activity, or that would benefit from increased SOD, CAT, and/or GPX enzyme activity, such as inflammation and oxidative stress.

Various particular embodiments that illustrate these aspects follow.

It is to be appreciated that the various modes of treatment or prevention of medical conditions as described are intended to mean "substantial", which includes total but also less than total treatment or prevention, and wherein some biologically or medically relevant result is achieved. A "subject," as used herein, is preferably a mammal, such as a human, but can also be an animal, e.g., domestic animals (e.g., dogs, cats and the like), farm animals (e.g., cows, sheep, pigs, horses and the like) and laboratory animals (e.g., rats, mice, guinea pigs and the like). An "effective amount" of an antioxidant inducing composition, as used herein, is a quantity of the composition provided by a particular route of administration and at a particular dosing regimen, that is sufficient to achieve a desired therapeutic and/or prophylactic effect. For example, an amount that results in the prevention of or a decrease in the symptoms associated with a disease that is being treated. The amount of the composition administered to the subject will depend on the type and severity of the disease, the amenability of the disorder to respond to antioxidants, and on the characteristics of the individual and their metabolic ability to respond to the compositions to produce in vivo, the antioxidants, such factors including general health, age, sex, body weight and tolerance to the active agents in the compositions. The skilled artisan will be able to determine appropriate dosages depending on these and other factors. Typically, an effective amount of the compositions of the present invention, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. The compositions of the present invention can also be administered in combination with each other, or with one or more additional therapeutic or prophylactic compounds.

It is advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the dietary supplement and the particular therapeutic effect to be achieved, and the limitations inherent in the art of compounding such an active compound for the treatment of individuals. The pharmaceutical compositions can be included in a container, pack, or dispenser together with instructions for administration. Typically, an oral dose is taken two-times to four-times daily, until symptom relief is apparent. The compositions of the present invention can also be administered in combination with each other, or with one or more additional therapeutic compounds.

It is to be appreciated that certain aspects, modes, embodiments, variations and features of the invention are described below in various levels of detail in order to provide a substantial understanding of the present invention. In general, such disclosure provides compositions beneficial to the health of a subject. In one embodiment, the compositions of the invention is a dietary supplement composition. In another embodiment, the compositions of the invention are combined with other dietary supplement compositions. In yet other embodiments, the composition of the invention is a pharmaceutical formulation.

Radicals, Oxidative Stress and Cellular Defense

Over the past few decades, free and bound reactive radicals, highly reactive and thereby destructive molecules, have come to be appreciated increasingly for their importance to human health and disease. Many common and life-threatening human diseases, including atherosclerosis, cancer, and aging, have radical-based pathological reactions as an underlying mechanism of injury.

A radical, or a free radical, is generally understood as a molecule with one or more unpaired electrons in its outer orbital shell. Many molecular species with bound radicals are monoxides or other oxygen containing compounds, generally referred to as reactive oxygen species (ROS). These highly unstable molecules tend to react rapidly with adjacent molecules, donating, abstracting, or even sharing their outer orbital electron(s). This reaction not only changes the adjacent, target molecule, sometimes in profound and beneficial ways, but it can also damage it, or alternatively the unpaired electron can be passed along to the target, i.e., as in a free radical, generating a second unwanted ROS, which can then go on to react positively or detrimentally with a new target. In fact, much of the high reactivity of ROS is due to their generation of such molecular chain reactions, effectively amplifying their effects many fold. Antioxidants afford protection because they can scavenge ROS and free radicals before they cause damage to the various biological molecules, or prevent oxidative damage from spreading, e.g., by interrupting the radical chain reaction of lipid peroxidation. The reactivity of radicals in the body, and the burden on the body that results in eventual pathological conditions, is known as oxidative stress.

For example, oxidative stress in the circulatory system is seen as atherosclerosis and by plaque deposition on the vessel walls. Plaques cause inflammatory responses, which increase radical formation by recruited immune cells, which worsens the cycle. It has been observed that the prime targets of both free radicals and ROS are the polyunsaturated fats in the membrane lipids of cells. The oxidative deterioration of polyunsaturated fats is known as lipid peroxidation. Lipid peroxidation severely impairs membrane function, which is believed to lead to the disorganization of cell structure and function. Products of lipid peroxidation such as malondialdehyde, a known mutagen reactive with proteins and amino acids, are a good measure of the amount of oxidative stress on the body. Lipofuscin, another byproduct of lipid peroxidation, accumulates in the body with age and it is believed that cytosolic buildup of this byproduct compromises brain function. What begins as localized pathological radical reactions thus result in oxidative stress that can and will eventually impact distal organ systems.

Vitamins such as vitamin C and vitamin E, both of which are found in foods and available as supplements, help the body reduce effects of oxidative stress. A more powerful combatant against the free radicals and ROS, however, is the body's own self defense system of naturally produced chemicals called antioxidants. These antioxidants act to terminate the propagation of free and bound radicals on ROS either by giving an electron to the free radical or ROS or by hindering their formation.

The body's antioxidant defense system includes three important natural antioxidants: superoxide dismutase (SOD), catalase (CAT), and glutathione peroxidase (GPX). Studies conducted have indicated that these antioxidants can work synergistically as the reactions they catalyze are metabolically sequential, beginning first with SOD followed by the actions of CAT and GPX.

SODs are a class of enzymes that catalyze reactions similar to the one below:

The role of SOD in the defense system is to remove superoxide radicals, which are a type of ROS. SOD is found in the body, primarily in three forms: (1) in the cytoplasm as Cu—Zn SOD; (2) in the mitochondrion as Mn-SOD; (3) and in an extracellular environment as CuSOD. Accordingly, the body is dependent upon the presence of zinc, copper, and manganese for the manufacture of SOD. During the removal of superoxide radicals by SOD, both hydroxyl and oxygen radicals are produced, which are catalyzed by CAT and GPX respectively.

Catalase (CAT) is present in the peroxisomes of nearly all aerobic cells, and serves to protect the cell from the toxic effects of hydrogen peroxide by catalyzing its decomposition into molecular oxygen and water without the production of free radicals.

The overall reaction is as follows:

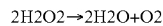

The protein exists as a dumbbell-shaped tetramer of four identical subunits (220,000 to 350,000 kDa). Each monomer contains a heme prosthetic group at the catalytic center. CAT monomers from certain species (e.g., cow) also contain one tightly bound NADP per subunit. This NADP may serve to protect the enzyme from oxidation by its $H_2O_2$ substrate. The body's production of CAT is dependent upon the availability of iron.

Glutathione peroxidases (GPXs) are a large class of diverse enzymes which catalyze the reduction of hydrogen peroxide (H2O2), organic hydroperoxides and lipid hydroperoxides to the corresponding alcohol using glutathione (GSH; glutamylcysteinylglycine) as the electron donor (Ursini et al., 1995). The GPX enzymes catalyze the reduction of $H_2O_2$ to water and organic peroxides (R—O—O—H) to the corresponding stable alcohols (R—O—H) using glutathione (GSH) as a source of reducing equivalents:

GPXs are important in helping to protect cells against oxidative damage, particularly lipid peroxidation. (Flohé et al., 1976). In mammals, the cytosolic (c) GPX family as well as a family of phospholipid hydroperoxide (PH) GPXs possess a selenocysteine residue at their active site. With the exception of phospholipid-hydroperoxide GPX, a monomer, all of the GPX enzymes are comprised of four identical subunits (monomer Mr 22-23 kDa). Each subunit contains a molecule of selenocysteine in the enzyme active site. The selenocysteine is thought to participate directly in electron donation to the peroxide substrate and become oxidized in the process. The enzyme then uses glutathione as an electron donor to regenerate the reduced form of the selenocysteine (Ursini, 1995). The GPX enzymes accept a wide variety of organic peroxides as substrates. The body's ability to produce GPX is in part dependent upon the adequate supply of selenium, and the supply of glutathione, a tripeptide that the body produces from the amino acids cysteine, glutamic acid, and glycine. Mammals contain plasma (p) GPXs, which are nonselenium containing enzymes in which cysteine replaces selenocysteine at their active site (Ursini et al., 1995). However, with the exception of phospholipid hydroperoxide GPX and perhaps pl-GPX, the enzymes exhibit a strong preference for glutathione as a source of reducing equivalents.

Despite the presence of SOD, CAT, and GPX, the body's antioxidant defense system is constantly subject to oxidative stress, and its ability to produce SOD, CAT, and GPX is compromised by the aging process and can further be impaired by inflammation, microbial or viral infections, the progression of cancer and neurological disorders, and other pathological conditions that produce, are caused by, or are exacerbated by oxidative stress.

Herb-Containing Compositions of the Invention

One object of the present invention is to provide new and useful compositions that alleviate oxidative stress in a subject. Another object of the present invention is to provide compositions that assist the body's natural antioxidant defense system(s) to alleviate the harm associated with oxidative stress. A further object of the present invention is to provide new compositions that upregulates the levels of SOD, CAT, and GPX, lowers the concentrations of free radicals and ROS, and decreases the rate of lipid peroxidation. Also, an object of the present invention is to provide dietary supplement compositions that alleviate oxidative stress as well as provide the body with other healthful benefits. Yet another object of the present invention is to formulate a composition in the form of a tonic or capsule, with the beneficial effects of alleviating oxidative stress that is of a sufficient concentration that may be easily implemented as part of a daily supplement regime. As noted above, the compositions of the invention provide for an overall net decrease in oxidative stress experienced by the mammal, with minimal undesirable side-effects. Advantageously, the composition itself provides fewer side effects than may be associated with each of the individual active agents in the composition.

These and other objects of the present invention will become more readily appreciated and understood from a consideration of the following detailed description of the present invention.

The present invention provides compositions derived from plant sources that induce the body's production of the antioxidants SOD, CAT, and GPX, and to a method of alleviating oxidative stress through use of these compositions. The compositions provide for efficient upregulation of these antioxidant enzymes enzymes, but advantageously the composition has lowered side-effects, i.e., reduced toxicity in the combination relative to the toxicity of each active agent when administered alone.

Observations related to lipid peroxidation are a good measure as to the amount of oxidative stress in a subject. Ideally, natural dietary supplements that induce production of SOD, CAT and GPX should also have the effect of reducing the concentration of free radicals and ROS in the body and result in decreased rates of lipid peroxidation. However, it has been observed that some formulations of dietary supplements that induce antioxidant production may contemporaneously cause an increase in the concentration of ROS leading to increased rates of lipid peroxidation. In other words, while some supplements may achieve an increase in the body's production of SOD, CAT, and GPX, it leaves the body with an overall net increase in oxidative stress. The present compositions do not add to the oxidative stress of the body.

Accordingly, choosing an active agent based simply on its ability to cause the induction of antioxidant production, per se, may not be an adequate selection criterion to achieve the overall desired goal of alleviating oxidative stress. Furthermore, plant extracts, which are typically the ingredients of natural dietary supplements, generally have their respective undesirable side-effects, that also need to be properly balanced in an overall formulation that accomplishes a dilution of individual undesirable effects. For example, research has indicated that an ethanol extract of *Bacopa monniera* produces toxicity in the brine shrimp lethality assay at about 300 mg/L (D'Souza et al. Phytotherapy Res. 2002, vol 16, 197-8) and enhances thyroid function, which may be an undesirable side effect (Kar et al. J. Ethnopharmacol. 2002, vol 81, 281-5).

The foregoing problems, among others, have been resolved by the present invention. Specifically, the present invention provides compositions containing appropriate mixtures of plant extracts are to safely induce antioxidant production to achieve an overall net decrease in oxidative stress, while at the same time diluting or reducing the undesirable side-effect and toxicity profiles associated with the individual extracts that make up the composition or any pharmaceutically acceptable formulation thereof.

The mixture contemplated by the present invention is comprised of the following nine plant derived active agents, which are listed in the following table along with the desired amounts of each agent. In one aspect, an antioxidant inducing agent further comprises any of the following nine plant derived active agents, which are incorporated into the antioxidant-inducing preparation in currently preferred concentrations (wt/wt) ranging from about 0.001 mg to about 1000 g, preferably about 0.1 mg to about 10 g, more preferably about 1 mg to about 2 grams, and most preferably about 50 mg to about 500 mg.

TABLE 1

| ACTIVE AGENTS | AMOUNT Per dosage unit | POSSIBLE UNDESIRED EFFECTS |
|---|---|---|
| *Bacopa monniera* extract | 0.001 mg to 1000 g | Considered very safe, but shows cytotoxicity in cultured cells (100 mg/kg) and anticancer activity (D'Souza et al., Phytotherapy Res. 2002, vol 16, 197-8); enhances thyroid function (200 mg/kg) (Kar et al. J. Ethnopharmacol. 2002, vol 81, 281-5) |
| Gotu Kola powder | 0.001 mg to 1000 g | Sedative and antidepressive effects; Possible hypotensive effect (PDR for Herbal Medicines (First Edn). Medical Economics Co., 1998, 729-30) |
| Ashwagandha powder | 0.001 mg to 1000 g | Considered very safe, but shows tranquilizing and hypotensive effects at 25 mg/kg (Mishra et al. Altern. Med. Rev. 2000, vol 5, 334-346); (Malhotra et al., Indian J. Physiol Pharmacol. 1965, vol 9, 127-136) |
| Green tea 98% Polyphenols 45% EGCG | 0.001 mg to 1000 g | Stimulant (caffeine); possible gastric irritant (PDR for Herbal Medicines (First Edn). Medical Economics Co., 1998, 710-1) |
| Turmeric extract 95% | 0.001 mg to 1000 g | Possible gastric irritant; possible antifertility effects at 125 mg/kg (PDR for Herbal Medicines (First Edn). Medical Economics Co., 1998, 786-7) |

TABLE 1-continued

| ACTIVE AGENTS | AMOUNT Per dosage unit | POSSIBLE UNDESIRED EFFECTS |
|---|---|---|
| Milk Thistle extract 70-80% | 0.001 mg to 1000 g | Considered very safe, but causes increases cell division in vitro (PDR for Herbal Medicines (First Edn). Medical Economics Co., 1998, 1138-9); May be proinflammatory at high doses of 250 mg/kg (Johnson et al. Planta Med. 2003, vol. 69, pp. 44-49) |
| *Aloe vera* powder | 0.001 mg to 1000 g | Laxative effect; Gastrointestinal cramping (PDR for Herbal Medicines (First Edn). Medical Economics Co., 1998, 630-3); inhibits thyroid function at 125 mg/kg (Kar et al., J. Ethnopharmacol. 2002, vol 81, 281-5) |
| *Ginko biloba* leaf extract | 0.001 mg to 1000 g | Mild gastrointestinal irritant; hypersensitivity reactions; may interfere with antithrombotic therapy at 240 mg/day (PDR for Herbal Medicines (First Edn). Medical Economics Co., 1998, 871-3) |
| N-Acetyl Cysteine | 0.001 mg to 1000 g | Considered Safe |

TABLE 2

| ACTIVE AGENTS | DOSAGE/DAY |
|---|---|
| *Bacopa monniera* extract | 10-4,000 mg |
| Milk Thistle extract 70-80% | 15-6,000 mg |
| Ashwagandha powder | 10-4,000 mg |
| Turmeric extract 95% | 5-2,000 mg |
| Gotu Kola powder | 10-4,000 mg |
| *Aloe vera* powder | 10-4,000 mg |
| Green tea, 98% Polyphenols 45% EGCG | 5-2,000 mg |
| *Ginko biloba* leaf extract | 5-2,000 mg |
| N-Acetyl Cysteine | 50-5,000 mg |

As shown in Table 1, many of the plant extracted active agents listed have the possibility of undesirable side-effects at high doses. However, by using a combination of some or all of these nine active agents in the respective amounts as listed in Table 2 to formulate a plant based composition (e.g., an oral dietary supplement), the desirable effects are additive and in certain embodiments, even synergistic. The overall effect then, is to upregulate at least one antioxidant enzyme, e.g., SOD, CAT, and GPX, while decreasing the concentration of free radicals and ROS and the rate of lipid peroxidation and other undesirable chemical reactions that result in oxidative stress on the body. For example, tissue level of thiobarbituric acid reactive chemical species (e.g., plasma TBARS) are reduced after administration of a composition of the invention to a subject. Furthermore, the likelihood of observing the undesired side-effects listed for each respective active agent is more remote as each extract is diluted out by a factor of up to nine (9).

Further, it is expected that the above-described active agents, in the amounts listed, will provide a combined remedy for oxidative stress that may be processed, in one embodiment, into a dosage unit for oral administration. This dosage unit is then administered, as a tablet, capsule, gel cap, pellet (globule), or in other carrier suitable for oral administration. Alternatively, the composition could be made available as a powder to be mixed with a suitable liquid, such as water, to form a tonic. In one embodiment, the formulation of the herb-containing composition of the invention is an oral dietary supplement. As such, an efficient, proper, and effective balance of these active agents can be formulated as to provide a composition that can be administered as a suitable daily oral dietary supplement.

In one embodiment, the herb-containing composition of the invention contains at least two (2) of the components (e.g., ingredients) summarized in Table 2. In some embodiments, the herb-containing composition of the invention contains two (2), three (3), four (4), five (5), six (6), seven (7), eight (8), or nine (9) of the components summarized in Table 2. The herb-containing composition of the invention can contain the components summarized in Table 2 in any quantity, or combination, suitable to give the desired oxidant preventative, therapeutic, or alleviating effect.

Antioxidant Properties and Uses of the Compositions of the Invention

The invention provides a method of preventing, alleviating or treating oxidative stress in a subject. The active agents of the invention are formulated into a composition that retains the prophylactic and therapeutic antioxidant inducing properties of the individual active agents, providing an additive or even synergistic antioxidant inducing effect relative to the effect of each active alone, while also decreasing the toxic side effect(s) to a subject, of the individual active agents of the compositions. The compositions of the invention are useful to eradicate free and bound radical reactions presently taking place or it may be used as prophylaxis against pathological free or bound radical reactions, which may occur as a result of a possible oxidant promoting incident (e.g., ischemic injury).

The present invention provides compositions for increasing the levels of antioxidants, via alteration of the activity level of SOD, CAT, and GPX enzymes in the body. The composition provides in one embodiment, a mixture of herbal extracts of *Bacopa monniera* (*B. monniera* or *Bacopa*), which contains a high percentage of the active chemicals bacosides A & B. Ingestion of Bacopa induces SOD, CAT, and GPX and provides the beneficial activities thereof, with pronounced results in the brain. Studies have indicated that the bacosides also increase protein and serotonin levels, while decreasing norepinephrine concentration in the hippocampus, hypothalamus, and cerebral cortex. *Bacopa* thus reduces the neurodegeneration in the brain that is caused by oxidative stress related to the accumulation of neurotoxic free radicals in the brain. Accordingly, it may be used to alleviate symptoms of neurodegenerative disorders, such as memory loss, Alzheimer's disease, and Parkinson's disease, and even aging.

*Bacopa monniera*

*Bacopa monniera* (common names: water hyssop and Brahmi) is a creeping perennial that thrives in warmer temperate climates. The genus *Bacopa* includes over 100 species of aquatic herbs distributed throughout the warmer regions of the world. The plant is a profusely branched herb, rooting at the nodes and forming dense mats. *B. monniera* extract (Bacopin®) is a standardized extract prepared from the leaves of the *B. monniera* plant (Sabinsa Corporation, Piscataway, N.J., USA). It is standardized for a minimum of 20% bacosides A & B, the active ingredients beneficial in the support of cognitive functions. Other extracts of the *B. monniera* plant standardized for a greater minimum levels of bacosides A & B (e.g., 30%, 40%, 50%, etc.) are useful in the compositions of the present invention and can be prepared by extraction techniques known in the art. The pharmacological effects of *B. monniera* preparations/extracts also include antioxidant, anti-inflammatory, cardiotonic and anticancer effects. Extract of *B. monniera* is commercially available, e.g., Viable Herbal Solutions (Morrisville, Pa., USA).

In one embodiment of the method preventing, alleviating or treating oxidative stress in a subject, from about 10 mg to about 4,000 mg *B. monniera* extract is administered to a subject daily using an herb-containing composition of the invention (See generally, Table 2). In one embodiment of the method preventing, alleviating or treating oxidative stress in a subject, from about 50 mg to about 3,000 mg *B. monniera* extract is administered to a subject daily using an herb-containing composition of the invention. In one embodiment of the method preventing, alleviating or treating oxidative stress in a subject, from about 100 mg to about 2,000 mg *B. monniera* extract is administered to a subject daily using an herb-containing composition of the invention. In one embodiment of the method preventing, alleviating or treating oxidative stress in a subject, at least about 200 mg *B. monniera* extract is administered to a subject daily using an herb-containing composition of the invention. In one embodiment, the *B. monniera* extract of the herb-containing composition is Bacopin®. In one embodiment, the herb-containing composition of the invention contains a *B. monniera* extract standardized for a at least about 20% bacosides A & B. In another embodiment, the herb-containing composition of the invention contains a *B. monniera* extract standardized for at least about 30% bacosides A & B. In another embodiment, the herb-containing composition of the invention contains a *B. monniera* extract standardized for at least about 40% bacosides A & B. In another embodiment, the herb-containing composition of the invention contains a *B. monniera* extract standardized for at least about 50% bacosides A & B.

Milk Thistle

Milk thistle (botanical name; *Silybum marianum*; other common names: Marian, *Silybum*, Silymarin) is a fine, tall plant, about the size of the Cotton Thistle, with cut into root-leaves, waved and spiny at the margin, of a deep, glossy green, with milk white veins, and is found not uncommonly in hedgebanks and on waste ground. Useful parts of the plant include, e.g., the whole herb, root, leaves, seeds and hull. Milk thistle seeds contain a bioflavonoid complex known as silymarin. Silymarin is an extract of the seeds of the milk thistle plant. A standardized extract should be 80% silymarin (the active ingredient). This constituent is responsible for the medical benefits of the plant. Silymarin is made up of three parts: silibinin, silidianin, and silicristin. Silibinin is the most active and is largely responsible for the benefits attributed to silymarin. As with other bioflavonoids, silymarin is a powerful antioxidant. Milk thistle extract is useful to protect or reverse damage to liver cells from toxins (e.g., alcohol, drugs, pesticides, poisons), to promote the regeneration of liver cells, to prevent or treat liver disease (e.g., liver cirrhosis, chronic hepatitis, and diabetes due to cirrhosis), indigestion, and cancer. Silymarin's effect in preventing liver destruction and enhancing liver function relates largely to its ability to inhibit the factors that are responsible for hepatic damage, i.e., free radicals and leukotrienes, coupled with an ability to stimulate liver protein synthesis. Milk thistle (80% silymarin) extract is commercially available, e.g., Stayleaner.com (Las Vegas, Nev., USA).

In one embodiment of the method preventing, alleviating or treating oxidative stress in a subject, from about 15 mg to about 6,000 mg milk thistle extract (70%-80%) is administered to a subject daily using an herb-containing composition of the invention (See generally, Table 2). In one embodiment of the method preventing, alleviating or treating oxidative stress in a subject, from about 50 mg to about 5,000 mg milk thistle extract (70%-80%) is administered to a subject daily using an herb-containing composition of the invention. In one embodiment of the method preventing, alleviating or treating oxidative stress in a subject, from about 100 mg to about 3,000 mg milk thistle extract (70%-80%) is administered to a subject daily using an herb-containing composition of the invention. In one embodiment of the method preventing, alleviating or treating oxidative stress in a subject, at least about 300 mg milk thistle extract (70%-80%) is administered to a subject daily using an herb-containing composition of the invention.

Ashwagandha

Ashwagandha (botanical names: *Withania somnifera* and *Physalis flexuosa*; other common names: winter cherry, Ashgandh, Achuvagandi, Amikkira-gadday, Amkulang-kalang, Amukkira-kilzhangu, Amukran-kizhangu, Asagandha, Asana, Asgandh, Asundha, Asvagandhi, Fatarfoda, Hirimaddina-gadday, Hirre-gadday, Penneroo-gadda, Pevette, Sogade-beru, Indian ginseng) is an erect branched shrub native to India, Pakistan and Sri Lanka. Ashwagandha preparations are useful to promote relaxation, bone marrow and women's health (e.g. stabilizes fetus and regenerates hormones), to enhance mental function (e.g., memory and concentration), as an aphrodisiac, and to treat fatigue, stress, cough, infertility, tissue inflammation, cancer, infectious disease, anxiety disorders, panic attacks, rheumatism, arthritis, pain, manic depression, alcoholic paranoia, and schizophrenia, fever, insomnia, infertility, aging, skin inflammations and disorders, alcoholism, Alzheimer's disease, anemia, carbuncles, convalescence, emaciation, HIV support, AIDS, immune system problems, lumbago, multiple sclerosis, muscle energy loss, paralysis, skin afflictions, swollen glands, ulcers, as well as breathing difficulties and as a diuretic. Ashwaganda powder is commertically available, e.g., iHerb Inc. (Monrovia, Calif., USA).

In one embodiment of the method preventing, alleviating or treating oxidative stress in a subject, from about 10 mg to about 4,000 mg Ashwagandha powder is administered to a subject daily using an herb-containing composition of the invention (See generally, Table 2). In one embodiment of the method preventing, alleviating or treating oxidative stress in a subject, from about 50 mg to about 3,000 mg Ashwagandha powder is administered to a subject daily using an herb-containing composition of the invention. In one embodiment of the method preventing, alleviating or treating oxidative stress in a subject, from about 100 mg to about 2,000 mg Ashwagandha powder is administered to a subject daily using an herb-containing composition of the invention. In one embodiment of the method preventing, alleviating or treating oxidative stress in a subject, at least about 200 mg Ashwagandha powder is administered to a subject daily using an herb-containing composition of the invention.

Turmeric

Turmeric extract 95% is prepared from the root or rhizome of the *Curcuma longa* plant (common names: *Curcuma*, Turmeric, Ukon, Goeratji, Kakoenji, Koenjet, Kondin, Kunir, Kunyit, Oendre, Rame, Renet, Temu kuning, Temu kunyit, Tius. Curcumin). *C. longa* is a perennial plant native to India. A compound called curcumin is a potent extract of the root, and has been attributed a wide range of therapeutic benefits. Turmeric extract is useful as an antioxidant, anti-inflammatory, anti-mutagenic agent, anti-cancer agent, cholagogueue, depurative, diuretic, fumitory, hemostatic agent, hepatoprotective agent, lactagogue, stomachic, tonic, and vulnerary. Turmeric preparations are useful to protect the liver from toxins, to reduce platelet aggregation, to prevent or treat inflammatory disease, inflammation, arthritis, psoriasis, cancer (e.g., prostate cancer and breast cancer), pain, Alzheimer's Disease, cardiovascular disease (e.g., arteriosclerosis and atherosclerosis). Turmeric extract that is standardized to 95% curcumin contains turmeric (with 95% curcumin). Turmeric extract 95% is commercially available, e.g., EZ-FITNESS (Northborough, Mass., USA).

In one embodiment of the method preventing, alleviating or treating oxidative stress in a subject, from about 5 mg to about 2,000 mg Turmeric extract (95%) is administered to a subject daily using an herb-containing composition of the invention (See generally, Table 2). In one embodiment of the method preventing, alleviating or treating oxidative stress in a subject, from about 10 mg to about 1,000 mg Turmeric extract (95%) is administered to a subject daily using an herb-containing composition of the invention. In one embodiment of the method preventing, alleviating or treating oxidative stress in a subject, from about 50 mg to about 500 mg Turmeric extract (95%) is administered to a subject daily using an herb-containing composition of the invention. In one embodiment of the method preventing, alleviating or treating oxidative stress in a subject, at least about 100 mg Turmeric extract (95%) is administered to a subject daily using an herb-containing composition of the invention.

*Gotu kola*

*Gotu kola* (botanical names: *Hydrocotyle asiatica*, *Centella asiatica*; other common names: *Centella*, March Pennywort, Indian Pennywort, Hydrocotyle, Brahmi (Sanskrit), Luei Gong Gen (Chinese)) is a slender, creeping perennial plant that grows commonly in swampy areas of India, Sri Lanka, Madagascar, South Africa and the tropics. *Gotu kola* is distinct from the kola nut. *Gotu kola* powder is prepared from the leaves and aerial parts of the plant and used for medicinal purposes. *Gotu kola* powder is useful to promote relaxation, to enhance mental function (e.g., memory and concentration), to promote tissue healing (e.g., wounds, skin, other connective tissues, lymph tissue, blood vessels, and mucous membranes) and to treat fatigue, anxiety, attention deficit disorder, insomnia, skin inflammations, leprosy, cancer, arthritis (e.g., psoriatic arthritis, anklylosing spondvlitis, and rheumatoid arthritis), hemorrhoids, tuberculosis, high blood pressure, congestive heart failure, venous insufficiency (pooling of blood in the veins, usually in the legs), sore throat, hepatitis, syphilis, stomach ulcers, epilepsy, diarrhea, fever, and asthma and as a mild diuretic. *Gotu kola* powder is commercially available, e.g., @Internatural (Twin Lakes, Wis., USA).

In one embodiment of the method preventing, alleviating or treating oxidative stress in a subject, from about 10 mg to about 4,000 mg *Gotu kola* powder is administered to a subject daily using an herb-containing composition of the invention (See generally, Table 2). In one embodiment of the method preventing, alleviating or treating oxidative stress in a subject, from about 25 mg to about 2,000 mg *Gotu kola* powder is administered to a subject daily using an herb-containing composition of the invention. In one embodiment of the method preventing, alleviating or treating oxidative stress in a subject, from about 50 mg to about 1,000 mg *Gotu kola* powder is administered to a subject daily using an herb-containing composition of the invention. In one embodiment of the method preventing, alleviating or treating oxidative stress in a subject, at least about 200 mg *Gotu kola* powder is administered to a subject daily using an herb-containing composition of the invention.

*Aloe vera*

*Aloe vera* (common names: medicinal aloe, burn plant, Barbados aloe, unguentine cactus) is a perennial plant; the strong, fibrous root produces a rosette of fleshy basal leaves as in the agave but considerably smaller that grows wild in East and South Africa and also cultivated in the West Indies and other tropical areas. *Aloe* contains anthraquinone glycosides, resins, polysaccharides, sterols, gelonins, and chromones, which contribute to the herbs medicinal properties. *Aloe* preparations, e.g., sap or powder, are useful as emollients, purgatives, a vulnerary agent, tonic, demulcent, vermifuge, antifungal, emmenagogue. *Aloe* preparations are useful to treat burns, piles, sunburn, wrinkles, headache, insect bites, skin irritations, cuts, ulcers, sores, herpes, jaundice, bursitis, canker sores, sore gums, poison ivy, inflammation, gastritis, and cancer. *Aloe vera* powder is commercially available, e.g., Red Lion International Trading & Brokerage Co. (Fullerton, Calif., USA).

In one embodiment of the method preventing, alleviating or treating oxidative stress in a subject, from about 10 mg to about 4,000 mg *Aloe vera* powder is administered to a subject daily using an herb-containing composition of the invention (See generally, Table 2). In one embodiment of the method preventing, alleviating or treating oxidative stress in a subject, from about 25 mg to about 2,000 mg Aloe vera powder is administered to a subject daily using an herb-containing composition of the invention. In one embodiment of the method preventing, alleviating or treating oxidative stress in a subject, from about 50 mg to about 1,000 mg *Aloe vera* powder is administered to a subject daily using an herb-containing composition of the invention. In one embodiment of the method preventing, alleviating or treating oxidative stress in a subject, at least about 200 mg *Aloe vera* powder is administered to a subject daily using an herb-containing composition of the invention.

Green Tea

Green tea extracts are useful in the compositions of the present invention. In some embodiments of the compositions of the invention, the Green tea extract is standardized for polyphenols. For example, Green tea, 98% polyphenols containing 45% polyphenols such as polyphenol (–)-epigallocatechin gallate (EGCG) is prepared from the leaf of the tea herb *Camellia sinensis*. Polyphenols, e.g., EGCG, in green tea are useful to protective against certain cancers, and they are also potent antioxidants. Green tea preparations are useful to promote immune function and to prevent and treat high cholesterol, heart disease, infection (e.g., *Staphylococcus aureus* infection, skin infection, bacterial infection, viral infection), acne, aging, immune disorders, dental caries, periodontitis, halitosis, dandruff, cancer, cardiovascular disease (e.g., hypertension, thrombosis, arteriosclerosis), diabetes, elevated blood glucose, diseases of the alimentary canal and respiratory system, influenza hepatitis, liver disease. Green tea extracts are commercially available, e.g., Hunan Kinglong Bio-Resource Co., Ltd., (Xingsha, Changsha, Hunan, P. R. China).

In one embodiment of the method preventing, alleviating or treating oxidative stress in a subject, from about 5 mg to about 2,000 mg Green tea (98% polyphenols, 45% EGCG) is administered to a subject daily using an herb-containing composition of the invention (See generally, Table 2). In one embodiment of the method preventing, alleviating or treating oxidative stress in a subject, from about 10 mg to about 1,000 mg Green tea (98% polyphenols, 45% EGCG) is administered to a subject daily using an herb-containing composition of the invention. In one embodiment of the method preventing, alleviating or treating oxidative stress in a subject, from about 50 mg to about 500 mg Green tea (98% polyphenols, 45% EGCG) is administered to a subject daily using an herb-containing composition of the invention. In one embodiment of the method preventing, alleviating or treating oxidative stress in a subject, at least about 100 mg Green tea (98% polyphenols, 45% EGCG) is administered to a subject daily using an herb-containing composition of the invention.

*Ginkgo biloba*

*Ginkgo biloba* (common name: *Maidenhair tree*) is a dioecious tree. *Ginkgo* leaf extracts have been shown to have a wide range of biological activities. The leaf extract utilized in medicine is standardized in a multi-step procedure designed to concentrate the desired active principles from the plant. These extracts contain approximately flavone glycosides (primarily composed of quercetin, kaempferol, and isorhamnetin) and terpene lactones (ginkgolides A, B, and C, and bilobalide). Other constituents typically include proanthocyanadins, glucose, rhamnose, organic acids, D-glucaric acid and ginkgolic acid (at most 5 ppm ginkgolic acids). The complex extract itself, rather than a single isolated component, is believed to be responsible for *Ginkgo's* biological activity. The flavonoid complex can remove free radicals in the peripheral and/or cerebral vascular systems, and inhibit lipid peroxidation. *Ginko biloba* extract is commercially available, e.g., iHerb Inc. (Monrovia, Calif., USA).

Some of the many valuable effects ginkgo has are stabilizing cell membranes, reducing free radical damage, improving blood circulation and enhancing oxygen and glucose use. *Ginkgo* is very beneficial for the brain, nerves and blood vessels. It is useful to improve short-term memory *Ginkgo biloba* has been used to improve cerebral blood circulation and to protect the nerves against damaging free radicals. *Ginkgo* leaf helps to maintain integrity and permeability of cell walls by inhibiting lipid peroxidation of membranes. *Ginkgo* extracts are useful to prevent or treat age-related physical and mental deterioration (e.g., Alzheimer's Disease and age-related dementia), cardiovascular disease, cerebral vascular insufficiency and impaired cerebral performance, congestive symptoms of premenstrual syndrome, allergies, age-related vision loss, depression, Raynaud's disease, peripheral vascular disease, intermittent claudication, vertigo, equilibrium disorder, prevention of altitude sickness, tinnitus (ringing in the ear), liver fibrosis, macular degeneration, asthma, graft rejection, and immune disorders that induce toxic shock.

In one embodiment of the method preventing, alleviating or treating oxidative stress in a subject, from about 5 mg to about 2,000 mg *G. biloba* leaf extract is administered to a subject daily using an herb-containing composition of the invention (See generally, Table 2). In one embodiment of the method preventing, alleviating or treating oxidative stress in a subject, from about 10 mg to about 1,000 mg *G. biloba* leaf extract is administered to a subject daily using an herb-containing composition of the invention. In one embodiment of the method preventing, alleviating or treating oxidative stress in a subject, from about 50 mg to about 500 mg *G. biloba* leaf extract is administered to a subject daily using an herb-containing composition of the invention. In one embodiment of the method preventing, alleviating or treating oxidative stress in a subject, at least about 200 mg *G. biloba* leaf extract is administered to a subject daily using an herb-containing composition of the invention.

N-Acetyl Cysteine

N-Acetyl Cysteine (NAC) is an acetylated form of the amino acid cysteine. NAC is an antioxidant, an antitoxin and immune support substance, and is found naturally in foods. There have been several instances wherein NAC has been demonstrated to be an antioxidant. NAC is commercially available, e.g., Doctor's Trust Vitamins (Orlando, Fla., USA).

NAC reacts very slowly with superoxide or the hydrogen peroxide free radicals. It can be seen from the rate constants that GSH is a more effective antioxidant against the hydroxyl radical in comparison to NAC (GSH $K_2=8.8.\times 10^9$, NAC $K_2=1.36\times 10^{10}$ at a pH of 1.0). NAC will inhibit HOCl at physiological concentration in a 3:1 ratio (respectively).

NAC is a precursor for glutathione, an important antioxidant that protects cells against oxidative stress. In addition to maintaining intracellular glutathione levels, NAC supplementation has been shown to suppresses Human Immunodeficiency virus (HIV) replication, to be protective against cell damage caused by chemotherapy and radiation therapy, to be immune enhancing, to protect against toxins as acetametaphen and other drugs, mercury, lead, and others, and is mucolytic, that is, it breaks up mucus seen in bronchoulmonary disease as cystic fibrosis, chronic bronchitis, asthma, gastritis, heart attack, angina pectoris, chronic obstructive pulmonary disease, prevention of kidney damage during coronary angiography, Unverricht-Lundborg disease, pseudoporphyria, and pneumonia. It has also been shown to offer protection against the superoxide free radical in porcine aortic endothelial cells and protects animals against paracetamol hepatotoxicity.

In one embodiment of the method preventing, alleviating or treating oxidative stress in a subject, from about 50 mg to about 5,000 mg N-acetyl cysteine is administered to a subject daily using an herb-containing composition of the invention (See generally, Table 2). In one embodiment of the method preventing, alleviating or treating oxidative stress in a subject, from about 100 mg to about 4,000 mg N-acetyl cysteine is administered to a subject daily using an herb-containing composition of the invention. In one embodiment of the method preventing, alleviating or treating oxidative stress in a subject, from about 250 mg to about 2,000 mg N-acetyl cysteine is administered to a subject daily using an herb-containing composition of the invention. In one embodiment of the method preventing, alleviating or treating oxidative stress in a subject, at least about 500 mg N-acetyl cysteine is administered to a subject daily using an herb-containing composition of the invention.

Free radical damage on the clinical level will be determined by the location of the preponderance of the oxidants generated, the type of oxidants, and the generation of pathological prostaglandins. The administration of compositions of the present invention is dependent upon where pathological free radical reactions are taking place. In one embodiment, the compositions of the present invention are orally administered to a subject in need thereof. Measuring the rate of the appearance of oxidation products can assess the effectiveness of the compositions of the invention. Effectiveness can also be monitored in patients by their clinical progress.

In one aspect, the invention provides a method of increasing the antioxidant activity level of a mammalian subject in need thereof, by increasing the level of enzyme activity of at least one enzyme, e.g., superoxide dismutase; catalase; and glutathione peroxidase, by administering to the subject an effective amount of an antioxidant-promoting composition of the invention, wherein the increased enzyme activity decreases the tissue damage caused by pathological free radicals. In one embodiment, the tissue damage caused by pathological free radicals occurs in a mammalian subject with a disease or condition selected from the group which includes, e.g., inflammation; infection; atherosclerosis; hypertension; cancer; radiation injury; neurological disease; neurodegenerative disease; ischemia/reperfusion injury; aging; wound healing; glutathione deficiency; acquired immunodeficiency syndrome; sickle cell anemia; and diabetes mellitus. In one embodiment of the method, the antioxidant-promoting composition is administered as an oral dietary supplement.

In another embodiment the invention provides a method of reducing the plasma level of c-reactive protein in a mammalian subject, by administering to the subject an effective amount of an antioxidant-promoting composition of the invention. In one embodiment of the method, the antioxidant-promoting composition is administered as an oral dietary supplement. In one embodiment of the method, the plasma level of c-reactive protein decreases by at least 10% or more in a 30 day period. In one embodiment of the method, the plasma level of c-reactive protein decreases by at least 20% or more in a 30 day period.

In another embodiment, the invention provides a method of reducing the blood pressure in a mammalian subject, by administering to the subject an effective amount of an antioxidant-promoting composition of the invention. In one embodiment of the method, the antioxidant-promoting composition is administered as an oral dietary supplement.

ROS and Human Health

Our bodies are continuously exposed to free radicals and other ROS, from both external sources (sunlight, other forms of radiation, pollution) and generated endogenously; oxidative stress and ROS-mediated tissue injury is a final common pathway for a number of pathological processes. Oxidative stress results in increased immune system activity, which leads to inflammation, recruitment of more immune cells, and release of cytokines and acute phase proteins that further exacerbate the stress on the body.

Cytokines

It is postulated that in conditions where there is excessive free radical production or infection (e.g. AIDS), there is a severe alteration of interleukin-2 (IL-2) production, which secondarily occurs due to glutathione (GSH) depletion. IL-2 is a glycoprotein, which is produced in response to mitogens and antigenic stimuli; it and other cytokines show a multiplicity of functions. Glutathione levels regulate the alpha chain, the larger of the two IL-2 receptors. Decreasing GSH levels would decrease the affinity of IL-2 to its corresponding receptors; consequently there would be a compromise in the function of IL-2. It is postulated that maintenance of GSH levels by the use of the compositions of the present invention would allow IL-2 and its receptors to elicit the normal immunological response for this particular interleukin.

Excessive oxidative stress results in amplified production of TNF-alpha and IL-6. IL-6 initiates and encourages the production of acute phase proteins such as c reactive protein, serum amyloid A protein, fibrinogen, and mannan-binding lectin. IL-1, IL-6, and TNF-alpha stimulate, for example, CRP synthesis by inducing hepatic gene expression, which triggers a variety of inflammatory responses and associated pathologies (see, Albert M. A. The role of C-reactive protein in cardiovascular disease risk. Curr Cardiol Rep 2000; 2(4):274-9). CRP is also a mediator of the complement system, part of the innate immune response (see, Yuan G, Expression of C5aR (CD88) of synoviocytes isolated from patients with rheumatoid arthritis and osteoarthritis. Chin Med J (Engl). 2003 September; 116(9):1408-12). The complement system provides further stimulus of TH1 and TH2 adaptive immune responses, which adds to the inflammatory response.

Production of tumor necrosis factor-alpha (TNF-alpha) by macrophages is stimulated by free radicals or oxidants (Chaudhri, G. and Clark, I. A.: J Immunol, vol. 143, 1990-1294, No. 4, 1989). TNF-alpha induces oxidant production by stimulating leukocytes, releasing arachidonic acid from leukocytes and releasing lysosomes. Therefore, enhancing plasma levels of antioxidants by administering the compounds of the present invention would decrease the production of TNF-alpha. It follows that, the maintenance/increase in antioxidant potential by administering the compositions of the present invention to a subject as described can prevent or treat cytokine-mediated tissue injury.

Inflammation

Inflammation can arise from infective agents (e.g. virion), trauma, chemical agents, immune reactions, metallic agents, and ionizing or thermal agents. The sine qua non of inflammation is heat, redness, edema, pain and loss of function (e.g., of the surrounding tissue). In any type of inflammation, characteristic inflammatory cells can be found, for example leukocytes, eosinophils, and macrophages/macrocytes. Each of these cell types produce radicals as part of a programmed response. Also as part of that "programmed" response are the production of inflammatory cytokines, such as TNF-alpha, CM-CSF and IL-2 and IL-6. These particular cytokines promote the production of oxidants such as nitric oxide and other reactive compounds. Oxidants are also generated as a byproduct of prostaglandin (PG) production, which is part of the propagation and amplification of the inflammatory process. Platelets are also involved in the inflammatory process by virtue of their ability to act as a plug (as in a clot); but also due to their liberation of platelet activating factor (PAF). PAF liberates arachidonic acid from leukocytes.

The production of prostaglandins is dependent upon the free radical tone (or concentration) of the microenvironment and metabolite synthesis. By decreasing the free radical tone and PG free radical intermediate metabolites, it is postulated that the pathological production of prostaglandins would be reduced, the amplification effect that PGs have as a role in the inflammatory process could be limited. Theoretically, either the lipooxygenase limb or the cyclooxygenase limb of the prostaglandin pathway could be affected by increased cellular antioxidants.

Free radicals or oxidants also have a plethora of different effects on the tissue in which it occurs, e.g., membrane damage, platelet adhesion, blood vessel intimal damage, etc. By increasing the antioxidant levels in areas where inflammation is occurring, it is postulated that the propagatory effect, tissue damage and pathologic physiologic reactions would be curtailed as well. The NF-KB transcription protein regulates the expression of a number of genes for proteins and cytokines involved in the inflammatory process (Baeuerle, P. A. and Baltimore, D.: Science, vol. 242, October, 1988). The activity and affinity that the NF-KB protein has for DNA is also regulated by GSH level (Staal, F. J. T, et al.: Proc. Natl. Acad. Sci., USA, vol. 87, pp 9943-9947, December 1990; Duh, E. J., et al.: Proc. Natl. Sci. Acad., USA, vol. 86, p 5974-5978, 1989). Enhancing levels of GSH decreases the activity and binding of NF-KB to DNA. By enhancing GSH levels, those cytokines and proteins involved in the inflammatory process would be decreased. The maintenance/increase of antioxidant potential by administering the compositions of the invention to a subject can, therefore, prevent or treat inflammation-mediated injury.

One important marker for inflammation is c reactive protein (CRP), a major acute phase response protein synthesized in the liver in response to the elaboration of acute phase response cytokines, such as interleukin-1 (IL-1), interleukin-6 (IL-6), and tumor necrosis factor alpha (TNF-alpha). Other associated acute phase proteins include serum amyloid A protein, fibrinogen, and mannan-binding lectin.

CRP concentrations are elevated in almost all inflammatory, infectious, and neoplastic diseases. Specific conditions include rheumatologic diseases (e.g., systemic lupus erythematosus, Sjogren's syndrome, rheumatoid arthritis), vasculitides (e.g., Wegener's granulomatosis), and chronic infections (e.g., tuberculosis, endocarditis). Certain malignant neoplasms, such as solid tumors, also may be associated with an elevated CRP level. Because CRP has a long half-life, CRP levels correlate well to its synthesis induced by persistent inflammation. Elevated levels of CRP are also associated with cardiovascular diseases such as endocarditis, angina pectoris, and myocardial infarction (see, http://www.americanheart.org/presenterjhtml?identifier=4648 and http://www.americanheart.org/presenterjhtml?identifier=3006541). Certain pathogens have been linked to atherogenesis and the development of clinically relevant coronary atherosclerosis. For example, cytomegalovirus (CMV), Herpes simplex virus (HSV) *Chlamydia pneumoniae*, and *Helicobacter pylori* have been associated with coronary artery disease (CAD), through inducement of vascular inflammation in addition to other mechanisms. This finding suggests that CMV contributes to atherogenesis by provoking an inflammatory response. CRP levels correlate with the clinical severity of CAD and with coronary events in both the acute and subacute phases of myocardial ischemia. Patients who are hospitalized for the treatment of unstable angina and have CRP concentrations above 0.3 mg/dL have significantly more ischemic episodes in the hospital than patients with lower CRP levels (see, Morrow D, Rifai N, Antman E M, et al. C-reactive protein is a potent predictor of mortality independently of and in combination with troponin T in acute coronary syndromes: a TIMI 11A substudy. Thrombolysis in Myocardial Infarction. J Am Coll Cardiol 1998; 31(7):1460-5). CRP concentrations are significantly lower in patients with stable angina pectoris than in those with unstable angina pectoris or an acute coronary syndrome. Patients with chronic stable angina who have stable, low CRP levels over time have fewer subsequent cardiovascular events during follow-up (see, Bogaty P, Poirier P, Simard S, et al. Biological profiles in subjects with recurrent acute coronary events compared with subjects with long-standing stable angina. Circulation 2001;103(25):3062-8). On the other hand, in patients with unstable angina pectoris, elevated CRP levels are strong predictors of plaque instability.

Many trials have confirmed the association between high levels of CRP and the risk of future coronary events such as MI and sudden cardiac death. In the European Concerted Action on Thrombosis and Disabilities study (Bolibar I, von Eckardstein A, Assmann G, et al. Short-term prognostic value of lipid measurements in patients with angina pectoris. The ECAT Angina Pectoris Study Group: European Concerted Action on Thrombosis and Disabilities. Thromb Haemost 2000; 84(6):955-60), elevation of mean CRP levels by 20% or more was found in patients after an MI. CRP levels are higher in survivors of MI with or without a demonstrable coronary lesion and increase further if other sites, such as peripheral vasculature, also are involved. Hence, CRP levels may serve to represent the inflammatory burden.

In the Monitoring Trends and Determinants in Cardiovascular Disease trial (Koenig W, Sund M, Frohlich M, et al. C-reactive protein, a sensitive marker of inflammation, predicts future risk of coronary heart disease in initially healthy middle-aged men: results from the MONICA (Monitoring Trends and Determinants in Cardiovascular Disease) Augsburg Cohort Study, 1984 to 1992. Circulation 1999; 99(2):237-42), a long-term prospective study of cardiovascular risk, patients with the highest CRP levels had 2.6 times the risk of MI. In another study (Haverkate F, Thompson S G, Duckert F. Haemostasis factors in angina pectoris; relation to gender, age and acute-phase reaction. Results of the ECAT Angina Pectoris Study Group. Thromb Haemost 1995; 73(4):561-7), postinfarction angina occurred in only 14% of patients with a normal CRP level. By comparison, 64% of patients admitted with high CRP levels had evidence of postinfarction angina; nearly 42% required revascularization, and 21% had recurrent MI.

In patients with MI, increased CRP concentration is associated with the presence of complex angiographic lesions and the need for revascularization (Moukarbel G V, Arnaout M S, Alam S E. C-reactive protein is a marker for a complex culprit lesion anatomy in unstable angina. Clin Cardiol 2001; 24(7):506-10). Elevated CRP levels also may represent a biomarker for patients who are most susceptible to reocclusion. In patients with stable CAD who underwent stent implantation following angioplasty, CRP levels increased over 96 hours in those with restenosis; in patients without restenosis, CRP levels peaked at 48 hours and then declined.

The normal serum concentration of CRP ranges from 3 mg/dL (90th percentile of the general US population) to more than 200 mg/dL. Generally, the American Heart Association has suggested that if hs-CRP level is lower than 1.0 mg/L, a person has a low risk of developing cardiovascular disease; if hs-CRP is between 1.0 and 3.0 mg/L, a person has an average risk, and if hs-CRP is higher than 3.0 mg/L, a person is at high risk for cardiovascular disease.

Because these ranges are not sensitive for the values required to determine cardiovascular risk in otherwise healthy persons, investigators have developed new, modified techniques to measure high-sensitivity CRP. The high-sensitivity CRP assay has been shown to detect concentrations below 0.2 mg/mL and uses labeled monoclonal or polyclonal anti-CRP antibodies in an enzyme-linked immunosorbent assay (ELISA) or an immunofluorescent assay (see, Rifai N, Ridker P M. High-sensitivity C-reactive protein: a novel and promising marker of coronary heart disease. Clin Chem 2001; 47(3):403-11).

Many conditions, activities, and medications affect levels of C-reactive protein. Increased levels are seen following allografts and graft occlusion, in connective tissue diseases (e.g., lupus erythematosus, Wegener's granulomatosis), arthritis, coronary artery disease, obesity, sepsis, in smokers, etc. Decreased levels of CRP are seen in response to inhibitory cytokines, exercise, and therapeutic doses of aspirin or 3-hydroxy-3-methylglutaryl-coenzyme A reductase inhibitors ("statins"). Accordingly, the compositions of the present invention, when administered to a subject having inflammation or the related/resultant disorders listed, can reduce CRP levels thereby reducing the inflammation and the severity of the related/resultant disorders. Administration of these compositions along with aspirin, naproxen, nambutome, other NSAID's or with statins appears to have a synergistic or additive effect on controlling inflammation and disease, depending on the particular combination.

Atherosclerosis

Atherosclerosis remains the major cause of death and premature disability in developed societies. Moreover, current predictions estimate that by the year 2020 cardiovascular diseases, notably atherosclerosis will become the leading global cause of total disease burden, defined as the years subtracted from healthy life by disability or premature death. Atherosclerosis is an inflammatory vascular disease characterized by endothelial activation, cellular influx, and production of mediators and cytokines. This process leads to the formation of foamy macrophages and atheromatous plaques and, finally, to atherothrombotic disease. Atherosclerosis is associated with high morbidity and mortality.

Atherosclerosis is a complex process that leads to heart attack, stroke, and limb loss by the plugging of the arteries with atherosclerotic plaque. This plaque is a form of oxidized fat. It is now generally recognized that atherosclerosis is a chronic inflammatory disease, characterized by over-recruitment of leukocytes (monocytes and T-cells) to the site of inflammation. Vascular injury in response to cardiovascular risk factors promotes endothelial dysfunction, resulting in enhanced adhesion molecule expression and secretion of pro-inflammatory cytokines and chemokines. This, in turn, leads to adherence, migration and accumulation of leukocytes within atherosclerotic lesions. The recent findings on inflammatory processes involved in atherosclerosis development provide important links between risk factors and the mechanisms of atherogenesis. Thus, research interest has increasingly focused on inflammatory biomarkers as means of predicting the risk of future clinical events. Indeed, elevated plasma levels of molecules such as soluble intercellular adhesion molecule-1, interleukin-6 or C-reactive protein (CRP) have been shown to represent inflammatory markers of future cardiovascular risk. Among these, CRP has emerged as the most powerful and accessible for clinical use (see, Steffens S., Inflammation and Atherosclerosis, Herz. 2004 December; 29(8):741-748).

CRP is a member of the pentraxin protein family, which is so named because these proteins possess five identical subunits. CRP, which is elaborated dramatically during acute inflammation, augments the immune response to certain antigens, activates complement, and increases the monocytic production of tissue factors. CRP binds to phosphoryl choline on bacterial surfaces, acting as an opsonin and playing a pivotal role in host defense. Interestingly, CRP also appears to bind low-density lipoprotein cholesterol (LDL-C) in vitro, which suggests a direct interaction with the atherogenic lipids.

Inflammation in the vessels leads to the release of reactive oxides and radicals from the immune cells. When radicals react with lipids, the consequence is lipid peroxidation. While a number of factors influence the development and severity of atherosclerosis, a major factor is the ROS-mediated peroxidation of serum low-density lipoproteins (LDLs). The dietary approach to the prevention of heart disease and stroke is based partially on adding dietary antioxidants to limit LDL oxidation, as well as decreasing the intake of fat itself. These approaches already have made significant inroads into the mortality from heart disease, but the compositions of the present invention may offer a safe pharmacological prevention in the future that is not as dependent upon willpower as are diet and exercise. The maintenance/increase of antioxidant potential by administering the compositions of the present invention to a subject, therefore, can prevent or treat cardiovascular disease, e.g., atherosclerosis.

Hypertension

The link between the elevation of the arterial blood pressure and the production of vascular lesions remains an area of inquiry. Recent evidence in the spontaneously hypertensive rat and the salt dependent Dahl hypertensive strains indicate that there is an excessive production of superoxide anion in microvascular endothelium and in circulating leukocytes (Swei et al., Mechanisms of Oxygen Free Radical Formation in Experimental Forms of Hypertension, On-line Proceedings of the 5th Internet World Congress on Biomedical Sciences '98 at McMaster University, Canada, Presentation # SAswei0837, 1998). These studies examining the role of the endothelial xanthine oxidase as a source for the oxidative stress in the SHR and Dahl forms of hypertension and their normotensive controls indicated that both models of hypertension exhibit significantly elevated levels of XD and XO and enhanced oxidative stress in both the arterial and venular segments of the microcirculation compared with their respective normotensive controls. The elevation of the oxidative stress and blood pressures could be reduced significantly by blockade of XD and XO. Similarly, the maintenance/increase of antioxidant potential by administering the compositions of the present invention to a subject, therefore, can prevent or treat cardiovascular disease, e.g., hypertension.

Membrane abnormalities in essential hypertensives (EH) are known. The respiratory burst enzyme, NADPH oxidase is located in the cell membrane of the neutrophil (PMNLs) and its activity is important in generation of oxygen derived free radical (ROS). As noted above, ROS have been implicated in vascular changes in variety of conditions. Sagar and coworkers studied the status of ROS and antioxidants in EH (Sagar et al., Mol Cell Biochem. 1992 April; 111(1-2):103-8).

Sagar and coworkers studied ten, age and sex-matched, healthy controls (GpI) and 26 untreated EH (Gp IIA mild-8, Gp IIB Moderate-8, Gp IIC Severe-10). After clinical examination and basic laboratory evaluation of subjects, neutrophils isolated from their blood were studied. Chemiluminescence (CL) emitted by PMNLs after stimulation was measured (counts/min) in a luminometer and was taken as measure of OFR production and thereby of NADPH oxidase activity. The levels of antioxidants, superoxide dismutase (SOD) and reduced glutathione (GSH), were also estimated. Chemiluminescence was increased significantly (p less than 0.01) in Gp IIC (243.04+/−24.9×10(3) counts per minute) as compared to Gp IIA (2.80+/−1.87), Gp IIB (34.54+/−30.24) and Gp I (0.52+/−0.15) and SOD was reduced significantly (p less than 0.05) in all EH (Gp IIA 3.9+/−0.3 units per mg protein, Gp IIB 3.5+/−0.3 and Gp IIC 3.12+/−0.3) as compared to controls (4.1+/−0.2). Similarly GSH was reduced (p less than 0.05) in EH (Gp IIA 11.2+/−1.7 mg per grn protein, Gp IIB 8.5+/−1.1 and Gp IIC 6.6+/−0.3) as compared to Gp I (13.5+/−2.5).

In addition, there is significant evidence that indicates blood vessels thicken as a result of oxidative stress. Calcium antagonists, especially the highly lipophilic amlodipine, lacidipine and nisoldipine, are shown to possess antioxidant properties. These drugs reduce the oxidation of LDL and its influx into the arterial wall, and reduce atherosclerotic lesions in animals. Platelet production of malondialdehyde, a marker of oxygen free radical formation, is suppressed by amlodipine, lacidipine or nifedipine in hypertensive patients. In the Regression Growth Evaluation Statin Study (REGRESS), co-administration of calcium antagonist, amlodipine or nifedipine with pravasatin caused a significant reduction in the appearance of new angiographic lesions. In the Verapamil in Hypertension and Atherosclerosis Study (VHAS), verapamil was more effective than chlorthalidone in promoting regression of thicker carotid lesions in parallel with a reduction in the incidence of cardiovascular events. In the Prospective Randomized Evaluation of the Vascular Effects of Norvasc Trial (PREVENT), amlodipine slowed the progression of early coronary atherosclerosis in patients with coronary artery disease. In a subprotocol of the Intervention as a Goal in the Hypertension Treatment (INSIGHT) study, nifedipine GITS significantly decreased intima-media thickness as compared to co-amilozide (hydrochlorothiazide+amiloride). Preliminary results of the European Lacidipine Study on Atherosclerosis (ELSA) show that lacidipine reduced the intima-media thickness progression rate as compared to atenolol. Thus, selective calcium antagonists treat hypertension and are potential antiatherosclerotic agents. (see, Hernandez, R. H., Calcium antagonists and atherosclerosis protection in hypertension, Am J Ther. 2003 November-December; 10(6):409-14). Likewise, the maintenance/increase of antioxidant potential by administering the compositions of the present invention to a subject, alone or in conjunction with calcium channel antagonists therefore, can prevent or treat cardiovascular disease, e.g., atherosclerosis, arterial lesions, intima-media thickening, and hypertension. This is illustrated further in the examples below.

Arthritis

Rheumatoid arthritis (RA) is a chronic multisystem disease of unknown etiology. Although there are a variety of systemic manifestations, the characteristic feature of RA is persistent inflammatory synovitis, usually involving peripheral joints in a symmetric distribution. The potential of the synovial inflammation to cause cartilage destruction and bone erosions and subsequent changes in joint integrity is the hallmark of the disease.

Direct correlation between the increases in TNF-alpha and MMP-1 production and collagen degradation seen in the RA patient suggests that collagenase cleavage of cartilage collagen is related to the activities of TNF-alpha and MMP-1. The reduction in cartilage type II collagen synthesis in early RA may contribute to the developing pathology, since a lack of synthesis of this molecule would inhibit maintenance of cartilage matrix. (see, Fraser A., Turnover of type II collagen and aggrecan in cartilage matrix at the onset of inflammatory arthritis in humans: relationship to mediators of systemic and local inflammation. Arthritis Rheum. 2003 November; 48(11):3085-95).

Deterioration of the joint is less likely to occur when the patient CRP levels are consistently controlled (see, Dawes, P. T., Rheumatoid arthritis: treatment which controls the C-reactive protein and erythrocyte sedimentation rate reduces radiological progression. The British Journal of Rheumatology, Vol 25, 44-49). CRP levels may also be helpful in following response to therapy in rheumatic disorders, and may help to differentiate rheumatoid arthritis (high levels of C-reactive protein) from uncomplicated lupus (low levels of C-reactive protein). When used to evaluate patients with arthritis, serum is the preferred specimen; there is no reason to examine synovial fluid for C-reactive protein. CRP levels, insulin sensitivity, HDL cholesterol, triglycerides and hypertension are inter-related in RA patients, who typically experience a markedly increased frequency of cardiovascular disease (see, Dessein P H, Cardiovascular risk in rheumatoid arthritis versus osteoarthritis: acute phase response related decreased insulin sensitivity and high-density lipoprotein cholesterol as well as clustering of metabolic syndrome features in rheumatoid arthritis. Arthritis Res. 2002; 4(5):R5).

Generally, the first line of medical management of RA is the use of nonsteroidal anti-inflammatory drugs (NSAIDs) and simple analgesics to control the symptoms and signs of the local inflammatory process. These agents are rapidly effective at mitigating signs and symptoms, but they appear to exert minimal effect on the progression of the disease. NSAIDs block the activity of the Cox enzymes and therefore the production of prostaglandins, prostacyclin, and thromboxanes. As a result, they have analgesic, anti-inflammatory, and antipyretic properties. In addition, the agents may exert other anti-inflammatory effects. Since these agents are all associated with a wide spectrum of undesirable and even toxic side-effects, the natural dietary supplement compositions of the present invention provide a non-toxic alternative to NSAIDs.

Although osteoarthritis (OA) is thought to derive from defective chondrocyte metabolism and thus inherently lack the large scale systemic response of rheumatoid arthritis, there is increasing interest in the acute phase proteins in OA (see, Sowers M., C-reactive protein as a biomarker of emergent osteoarthritis. Osteoarthritis Cartilage. 2002 August; 10(8):595-601). Severity of pain, is associated with hsCRP levels in patients with advanced OA (see, Sturmer T., Severity and extent of osteoarthritis and low grade systemic inflammation as assessed by high sensitivity C reactive protein, Ann Rheum Dis. 2004 February; 63(2):200-5).

Accordingly, the maintenance/increase of antioxidant potential in a mammal provides a method of ameliorating or decreasing tissue degradation and inflammation seen in arthritis (RA and OA). By administering the compositions of the present invention to a subject as described above, the compositions can therefore, prevent or treat OA and RA. The compositions may be given with other pharmaceutical agents, e.g., Relafen and other NSAID's or glucocorticoids (cortisone, dexamethasone, etc.) to achieve a greater anti-inflammatory effect.

Cancer and Other Malignancies

Cancer and other malignancies all entail unconstrained cell growth and proliferation based upon changes in the cell's genetic information. In most cases, for example, one or more genes that normally constrain cell growth and replication is/are mutated, or otherwise inactivated. These genetic deficiencies correspond directly with deletions and sequence changes in the genetic code, resident in the cell's DNA. A frequently seen final common cause of such DNA damage is free radical injury. Of the myriad injuries sustained by our DNA on a daily basis, most are repaired by normal DNA repair mechanisms within the cell, while some result in cell death. Since such injuries are sporadic and distributed somewhat randomly across the genome, most lethal DNA injuries are clinically inconsequential, resulting in the loss of a few cells among millions. However, when a single cell sustains an injury that impairs growth regulation, it can proliferate disproportionately and grow rapidly to dominate the cell population by positive natural selection. The result is a tumor, frequently a malignant one, where the constraint of growth and proliferation is particularly deficient. Therefore, free radical injury to the genetic material is a major final common pathway for carcinogenesis.

An approach to creating anti-tumor therapeutics that appears to have early success is aimed at preventing tumor induced angiogenesis, thereby reducing blood supply to the tumor to prevent growth and to kill the proliferating cells by starving them of nutrients and oxygen. While most candidate therapeutics are direct inhibitors of angiogenesis, other treatments are designed to prevent initiation of the angiogenesis response. Tumor formation is associated with localized inflammation, and increases of c-reactive proteins (CRP), which are well known prognostic indicators of patient survival (see, McKeown, D J., The relationship between circulating concentrations of C-reactive protein, inflammatory cytokines and cytokine receptors in patients with non-small-cell lung cancer. Br J Cancer. Dec. 13, 2004; 91(12):1993-5). Elevated CRP levels are seen in many types of cancer, see for example, McArdle P A The relationship between interleukin-6 and C-reactive protein in patients with benign and malignant prostate disease, Br J Cancer. Nov. 15 2004; 91(10):1755-7; Saddler, D., C-reactive protein elevation and the risk of colorectal cancer, Gastroenterol Nurs. 2004 September-October; 27(5):246-7; and Alexandrakis, M G The relation between bone marrow angiogenesis and the proliferation index Ki-67 in multiple myeloma, J Clin Pathol. 2004 August; 57(8):856-60.

CRP can significantly influence gene expression in the vascular endothelium. CRP is upregulated by IL-6, and increases expression of IL-8, ZF9, Activin A, MCP-1, EXT1, Cited2, PAI-1, Fibronectin-1, Gravin, Connexin-43, and SORL-1, and decreases expression of MAT2A, WRB, RCN1, TEB4, DNCL1 and Annexin A1 (see, Wang, Q., Effect of C-Reactive Protein on Gene Expression in Vascular Endothelial Cells, Am J Physiol Heart Circ Physiol. Dec. 9, 2004). Thus, CRP-responsive genes may have a broad functional role in cell growth and differentiation, vascular remodeling and solid tumor development. Inhibiting CRP would provide an additional approach to current cancer therapies and may provide a prophylactic anticancer effect by inhibiting inflammation and angiogenesis.

By administering the compositions of the present invention to a subject as described above, the compositions can therefore, prevent or treat cancers that respond to antioxidant treatments. Such cancers include for example but not limited to, breast cancer (see, Kline K, Vitamin E and breast cancer, J Nutr. 2004 December; 134(12 Suppl):3458S-3462S); lung cancer (see, Wright M E, Development of a comprehensive dietary antioxidant index and application to lung cancer risk in a cohort of male smokers. Am J Epidemiol. Jul. 1, 2004; 160(1):68-76); ovarian cancer (see, Anderson K, Differential response of human ovarian cancer cells to induction of apoptosis by vitamin E Succinate and vitamin E analogue, alpha-TEA. Cancer Res. Jun. 15, 2004; 64(12):4263-9); and colon cancer (see, Al-Shaer MH., C-reactive protein and risk of colon cancer. JAMA. Jun. 16, 2004; 291(23):2819). In fact, colorectal carcinogenesis is associated with serious oxidative stress gradual advancement of oxidative-antioxidative disorders is followed by progression of colorectal cancer (see, Skrzydlewska E, Lipid peroxidation and antioxidant status in colorectal cancer. World J Gastroenterol. Jan. 21, 2005; 11(3):403-6).

The compositions may be given with other pharmaceutical agents, e.g., glucocorticoids, camptothecins, mustard agents, and other chemotherapy drugs, to achieve a greater anti-tumor response and to control inflammation.

Radiation Injury

Radiation injury represents an important cause of ROS-mediated disease. With respect to commonly encountered levels of radiation, depending upon the situation, about two-thirds of the sustained injury is mediated not by the radiation itself, but by the ROS generated secondarily. This applies not only to the acutely toxic forms of radiation injury, but the long-term, mutagenic (and hence carcinogenic) effects as well.

An important clinical application of this principle is encountered regularly in the treatment of cancer by radiation therapy. Large tumors often outgrow their blood supplies and tumor cells die within the center, despite being well oxygenated at the periphery. Between these two regions is an area of tumor that is poorly oxygenated, yet remains viable. Radiation therapy of such tumors is particularly effective at the periphery, where an abundant concentration of oxygen is available to form tumorcidal ROS. The poorly oxygenated center is injured to a significantly smaller degree. While the dead cells in the center don't survive anyway, the poorly oxygenated, yet viable, cells between these two areas can survive a safe dose of radiation therapy, and thereby seed a later local recurrence of the tumor. This is a major reason why many large tumors are treated by a combination of radiation therapy (to kill the tumor at its advancing edges) and surgical removal of the bulk of the tumor, including these particularly dangerous remaining cells.

ROS can be generated within the cell not only by external sources of radiation, but also within the body as a by-product of normal metabolic processes. An important source of endogenous free radicals is the metabolism of some drugs, pollutants, and other chemicals and toxins, collectively termed xenobiotics. While some of these are directly toxic, many others generate massive free radical fluxes via the very metabolic processes that the body uses to detoxify them. One example is the metabolism of the herbicide paraquat. At one time, drug enforcement authorities used this herbicide to kill marijuana plants. Growers realized they could harvest the sprayed crop before it wilted, and still sell the paraquat-laced product. Many who smoked this product subsequently died of a fulminate lung injury. Fortunately, this approach has been abandoned as a particularly inhumane way to solve the drug problem.

While the paraquat story is a particularly striking example of a metabolic mechanism of free radical toxicity, many commonly encountered xenobiotics, including cigarette smoke, air pollutants, and even alcohol are toxic, and often carcinogenic to a large degree by virtue of the free radicals generated by their catabolism within our bodies. Moreover, there is accumulating evidence that a diet rich in fruits and vegetables, which are high in natural antioxidants, and low in saturated fat (a particularly vulnerable target for damage by ROS), reduces the risk of atherosclerosis and cancer. The maintenance/increase of antioxidant potential by administering the compositions of the present invention, therefore, can prevent or treat atherosclerosis and cancer.

The maintenance/increase of antioxidant potential by administering the compositions of the present invention to a subject, therefore, can prevent or treat radiation-mediated injury.

Neurological and Neurodegenerative Diseases

Neurological and neurodegenerative diseases affect millions of Americans. These include depression, obsessive-compulsive disorder, Alzheimer's, allergies, anorexia, schizophrenia, as well as other neurological conditions resulting from improper modulation of neurotransmitter levels or improper modulation of immune system functions, as well as behavioral disorders such as ADD (Attention Deficit Disorder) and ADHD (Attention Deficit Hyperactivity Disorder). Oxidative stress links diverse neuropathological conditions that include stroke, Parkinson's Disease, and Alzheimer's Disease and has been modelled in vitro with various paradigms that lead to neuronal cell death following the increased accumulation of reactive oxygen species. For example, immortalized neurons and immature primary cortical neurons undergo cell death in response to depletion of the anti-oxidant glutathione, which can be elicited by administration of glutamate at high concentrations.

A number of these diseases appear to have ROS toxicity as a central component of their underlying mechanism of nerve cell destruction, including, but not limited to, amyotrophic lateral sclerosis (ALS, or Lou Gehrig's disease), Parkinson's disease, and Alzheimer's disease. For example, Alzheimer's disease is a neurodegenerative disorder associated with aging and cognitive decline. Amyloid beta peptide (1-42) is a primary constituent of senile plaques—a hallmark of Alzheimer's disease—and has been implicated in the pathogenesis of the disease. Studies have shown that methionine residue 35 of beta(1-42) may play a critical role in Abeta(1-42)-mediated oxidative stress and neurotoxicity (see, Boyd-Kimball D, Rodent Abeta(1-42) exhibits oxidative stress properties similar to those of human Abeta(1-42): Implications for proposed mechanisms of toxicity. J Alzheimer's Dis. 2004 October; 6(5):515-25).

Additionally, oxidative stress is associated with the selective loss of dopaminergic neurons of the substantia nigra in Parkinson's disease. The role of alpha synuclein as a potential target of intracellular oxidants has been demonstrated by identification of posttranslational modifications of synuclein within intracellular aggregates that accumulate in PD brains, as well as the ability of a number of oxidative insults to induce synuclein oligomerization (see, Cole N B., Metal-catalyzed oxidation of alpha synuclein: helping to define the relationship between oligomers, protofilaments and filaments. J Biol. Chem. 2004 Dec. 21).

Accordingly, the maintenance/increase of antioxidant potential by administering the compositions of the present invention to a subject, therefore, can prevent or treat neurological and neurodegenerative diseases that have inflammation and oxidative stress as causative or complicating factors.

Ischemia/Reperfusion Injury

When an organ is deprived of its blood supply (ischemia) it is injured, not just by the temporary loss of oxygen, but also by the ROS that are generated by reaction with the oxygen that is reintroduced at reperfusion, when the blood supply is restored. In some clinical situations, this injury can prevented by giving antioxidants, sometimes even after the period of ischemia, but just prior to reperfusion. For example, the preservation of kidneys, livers, and other organs in solutions that contain antioxidants, as well as other agents, is now routine prior to their transplantation. Another example is the use of drugs that block the function of free radical generating enzymes prior to stopping the heart for cardiac surgery. These drugs help prevent reperfusion injury when the heart is restarted and flow is restored. This reperfusion injury mechanism also has been found to play an important role in patients suffering from multiple organ failure after trauma, massive surgery, or shock. Multiple organ failure is now the leading cause of death in intensive care units, and extensive efforts are under way to understand better how ROS contribute to this syndrome.

Ischemia, which is low tissue oxygen saturation of a given tissue, can occur in any organ system. All organs require a blood supply in order to remain viable. The intact organ whose arterial supply is compromised (either by partial or total occlusion) is rendered ischemic (e.g., coronary artery occlusion, organs awaiting transplantation, cerebral vascular accident, compartment syndrome, etc.). There are reversible and irreversible histological, physiological and biochemical changes which occur as a result of ischemic injury to tissue. End stage ischemia is universal and demonstrates necrosis. Demopoulos et al. (Fed. Proc. 32:1859-1861, 1973b) theorized that the necrosis observed in ischemic tissue was due to oxidants generated by the uncoupling of the oxidative phosphorylation chain in mitochondria. Zweir, et al., provided direct evidence that free radical production resulted from ischemia using electron spin resonance spectroscopy (Proc. Natl. Acad. Sci. USA, vol. 84, pp: 1404-1407). In reperfusion studies Zweir showed the alteration of one of the free radicals with the use of superoxide dismutase (which eliminated superoxide). In ischemic cardiac myocyte a depletion of ATP induces the release of arachidonic acid and palmitic acid. Vitamin E (Massey, K. D. and Burton, K. P.: Am. J. Physiol. 256 (Heart Circ. Physiol. 25): H1192-H1199, 1989), vitamin E acetate and selenium selenite have been used to protect tissue against free radicals, which have occurred in ischemia. It is postulated that enhancement of tissue antioxidants would eliminate the superoxide free radical, as well as other oxidants that are not double produced as a result of ischemia and prostaglandin metabolite production. The maintenance/increase of antioxidant potential by administering the compositions of the present invention to a subject, therefore, can prevent or treat ischemia/reperfusion injury, e.g., brain ischemia and heart ischemia (i.e., myocardial infarction).

Aging

Aging is a remarkably complex process that has managed to remain relatively opaque to scientific understanding. There is now evidence that aging is a series of processes, i.e., a series of controlled mechanisms, and not just the passive accumulation of wear and tear over the years. If aging is a series of processes, some of these processes are potentially controllable, or at least modifiable. One of the most important of these processes is comprised of an accumulation of the molecular injuries that are mediated by free radicals and other ROS. Recent studies indicate that the therapeutic manipulation of ROS metabolism can actually extend the total life span of mice to a significant degree. The maintenance/increase of antioxidant potential by administering the compositions of the present invention to a subject can, therefore, prevent or treat age-mediate injury.

Burns/Wound Healing

Burn wounds to skin and other organs can occur by ultraviolet radiation (UV), chemical agents, conductive or convective heat, electrocution, etc. Burns can occur in lung parenchyma by the inhalation of smoke or caustic gases (see section on tissue injury). Burn wounds to the skin are graded as first, second, and third degree burns (the most severe). It is postulated that any burn wound produces tissue damage, largely by the production of oxidants (Till, G. O.: Am J. Pathol. July; 1325(1): 195-202, 1989). Liposomes (artificial membranes) when exposed to UV undergo peroxidation (Bose, B: Biotechnol Appl. Biochem, October, 12 (5): 557-61, 1990). It has been postulated that similar peroxidation occurs in skin when it is exposed to UV radiation (Somer, E.:Shape Magazine, p 33-35, November 1992; Hamanka, H.: J. Dermatol, October 17(10):595-8, 1990). Exposure of skin to UV varies in intensity and length of exposure. Daily exposure to UV (e.g., sunlight) has been postulated to result in skin wrinkling. Depending on the intensity and/or length of skin exposure to UV light, first, second or third degree burns can result.

Hairless mice exposed to a single exposure of UV resulted in a broad range decrease of antioxidants: glutathione, beta-carotene, alpha-tocopherol. The enzyme activity of catalase and glutathione reductase was also decrease (Fuchs, J.: J. Invest Dermatol, December, 93(6): 769-73, 1989). These decreases in the concentration of antioxidants and enzyme activity in skin due to UV exposure supports the concept of the occurrence of free radicals in skin. It is postulated that lipid peroxidation could be inhibited by an enhancement of antioxidants in skin. Lipid peroxidation in liposomes exposed to UV can be inhibited by placement of beta-carotene or alpha-tocopherol in liposomes (Pelle, E.: Arch. Biochem. Biophys. December 283 (2): 234-40, 1990).

Excessive free radical production has been cited as a factor in delayed wound healing (Yukie, N.: Dermatolgica, 179 (suppl 1): 101-106, 1989). The maintenance/increase of antioxidant potential by administering the compositions of the present invention to a subject of antioxidants would, therefore, ameliorate the effects of pathologic oxidants and prostaglandin production as well as promote wound healing in various skin injuries.

Tissue Injury and Degeneration

Tissue injury occurs as a result of an inflammatory focus occurring in the area of a cell or an organ. For example plasma oxidative stress occurs in patients with ulcerative colitis, and omega-3 fatty acids are under study as free radical scavengers for protecting the patients against the overall effect of oxidative stress (see, Barbosa D S, Decreased oxidative stress in patients with ulcerative colitis supplemented with fish oil omega-3 fatty acids., Nutrition. 2003 October; 19(10):837-42). C-reactive protein levels corresponded closely with clinical and pathological indices of relapse, remission and response to therapy in patients with Crohn's disease. Assay of serum C-reactive protein provides an objective criterion of inflammatory activity, which may be useful in the assessment, management and study of Crohn's disease (see, Fagan, E. A., Serum levels of C-reactive protein in Crohn's disease and ulcerative colitis. Eur J Clin Invest. 1982 August; 12(4):351-9). Accordingly, CRP levels may also be helpful in following response to therapy for tissue injuries, and may help to differentiate in Crohn's disease (high C-reactive protein) from ulcerative colitis (low C-reactive protein).

Inflammation can occur due to a local inducement (e.g. hepatitis) or due to an injury occurring to one organ in a remote location and another discontiguous organ, which also sustains an injury (e.g., severe burns occurring to skin (the first organ) with subsequent injury to the lungs (the second organ)). In either case, local or remote tissue injury is believed to be mediated by activated leukocytes, which release oxidants. Oxidants released from leukocytes react with cellular (organ) membranes (Fantone, J. C. and Ward, P. A.: Am. J. of Path., vol. 107(3), P. 397-418, 1982). Repeated cellular membrane exposure to oxidants decreases antioxidant levels, which increases their susceptibility to damage. Increasing the levels of antioxidants in the extracellular and/or intracellular, and/or the lipid-aqueous interface is postulated to thwart oxidant damage to vital cellular structures. The maintenance/increase of antioxidant potential by administering the compositions of the invention to a subject can, therefore, prevent or treat ROS-mediated tissue injury or other types of inflammatory tissue degeneration.

Sepsis

Sepsis is characterized as a systemic infection by a microorganism. Frequently it is fatal and if not fatal increases the morbidity of the patient. In sepsis, red blood cells become sticky and deformed (Baker, C. H., et al.: Circ. Shock 20:127-139, 1986; Powell, J., et al.: Critical Care Med., vol 19 (5), 1991), which can lead to occlusion of the microvasculature. Cardiac output is increased, but in the kidney, liver, and musculature blood flow is decreased (Hurd, T. C., et al.: Archives of Surg., vol. 123, 1988). Evidence of free radical damage has been demonstrated in in vitro and in vivo studies involving shock induced by endotoxins (McKechnie, K., et al.: Circ. Shock 19: 429-439, 1986). Findings include increased vascular permeability, damaged mitochondria, disruption of calcium transport by the sarcoplasmic reticulum, and the activation of the complement system (particularly C5a). In septic infections, serum levels of acute phase proteins, particularly CRP, are elevated, which increases activation of the complement response as well as other cell mediated responses.

The maintenance/increase of antioxidant potential by administration of the compositions of the present invention to a subject can, therefore, prevent or treat sepsis-mediated inflammatory cellular damage.

GSH Deficiency

Artificial depletion of glutathione interferes with normal T cell function, particularly within the first 30-60 minutes of activation (Fischman, C. M., et. al: The Journal of Immunology, vol. 127(6), p 2257-2262, 1981; Hamilos, D. L. and Wedner, H. H.: Journal of Immunology, vol. 135 (4), 1985). Glutathione deficient T cells showed a decrease in thymidine incorporation and blast transformation. The greater the depletion of glutathione the longer it took cells to recover to normal levels. If cellular GSH depletion was severe enough the cells never recovered to normal GSH levels. Increased glutamate levels, which are found in AIDS patients (Eck, H.-P. and Droge, W.: Bio. Chem. Hoppe-Seyler, vol. 370, pp 109-113), appear to inhibit the transport of cystine into macrophages. Under normal circumstances cysteine is reduced to cysteine by the macrophages. Cysteine is exported into the microenvironment for the use of T cells for the ultimate conversion to intracellular glutathione. T cells cannot utilize cystine. In AIDS patients glutathione is depleted (Eck, H.-P, et al.: Biol. Chem. Hoppe-Seyler, vol. 370, pp 101-108), which is postulated to adversely effect T cell function. This scenario is believed to be similar to the experimental studies, which demonstrated abnormal T cell function as a result of artificial GSH depletion. The maintenance/increase of antioxidant potential by administering the compositions of the present invention to a subject can, therefore, prevent or treat GSH deficiency.

AIDS

There is considerable evidence which indicates that HIV infection and subsequently ARC/AIDS is by in large a free radically mediated disease. This analysis can be made indirectly as judged by the antioxidant levels in humans and their consequences on the immune system. One of those antioxidants, glutathione (GSH), is decreased as a result of HIV infecting the host. The GSH levels continue to decrease as the disease progresses through ARC and finally to AIDS. Micromolar changes in GSH levels have an untoward effect on the function of T lymphocytes (which can be viewed as the pivotal leader of the immune system). GSH shows a multiplicity of uses in the immune system. Thiol concentrations (e.g. GSH) regulate the replication of HIV genomic expression (Kalebic, T., et al.: Proc. Natl. Acad. Sci., USA,; 88: 986-90, 1991; Roeder, M., et al.,: Porc. Natl. Acad. Sci., USA, vol. 87, p 4884-4888). Increasing the concentrations of thiols (GSH, NAC, GSE (glutathione ester)) in culture medium of U1 cell line (promonocytes) results in suppression of viral assembly, HIV reverse transcriptase production and viral replication. The maintenance of antioxidant potential by administering the compositions of the invention to a subject can, therefore, prevent or treat HIV-mediated injury.

Immunomodulation

There are numerous activators of leukocytes (e.g., exposure to ingestible particles, certain soluble factors such as complement, lectins, phorbol esters, etc.). A consequence of leukocyte activation is the release of the MPO system ($H_2O_2$+halide+myleoperoxidase) and other oxidants. The more potent the stimulus of activation of leukocytes is, the greater the release of oxidants and the greater the suppression of T lymphocytic function. When activated leukocytes were combined with T lymphocytes and catalase, there was no suppression of lymphocytic function; monocytes (which contain enzymatic antioxidants: glutathione peroxidase, catalase, myeloperoxidase) were used in lieu of catalase, again there was no suppression (Lipsky, P. E.: J. Clin, Invest. 73:53, 1984). Antibody production by B lymphocytes showed a similar susceptibility to free radical damage as did lymphocytes (El-Hag, A., et al.: J. of Immunol., vol. 136 (9), 1986). A following is a rank order for various lymphocytic functions to free radical attack: immunoglobulin secreting cells were the most sensitive (particularly to the MPO system); Natural Killer cell activity, DNA synthetic responses to PHA and Con A were intermediate; and the DNA response to PWM was the least susceptible. Monocytes/macrophages have approximately 15-20 times higher catalase content in comparison to lymphocytes (Meerhof, L. J. and Roos, D.: J. Reticulendothel. Soc. 28: 419) and would therefore be much less susceptible to oxidative damage. Lymphocytes exposed to a free radical generating system demonstrate changes in membrane characteristics: 63% decrease in E rosette formation, 44% decrease in surface immunoglobulins and 90% decrease in cap formation (Kraut, E. H. and Sagone, A. L.: J. of Lab. Clin. Med., November 1981, p 697-703). The maintenance/increase of antioxidant potential by administering the compositions of the invention to a subject can, therefore, prevent or treat immune damage by ROS.

Sickle Cell Anemia

Sickle cell anemia is a genetically determined disease. Analysis of sickle cell patients RBC (HbS) demonstrates a number of peculiarities of the membrane: frozen spectrin shell of irreversibly sickled RBC, an abnormal orientation of the lipid bilayer phospholipids, deficient calcium-ATPase, a propensity for HbS RBCs to adhere to vascular endothelium, and oxidized thiol groups on the HbS molecule. It is the characteristic of the tendency of adherence to the vascular endothelium, which is the likely primary pathogenesis of the disease, which is occlusion of the microvasculature. Consequently, ischemic injury occurs to organs (see section on ischemia). Additional evidence of free radical damage to HbS is a deficiency of alpha-tocopherol, increased amounts of malondialdehyde, and abnormal group cross linking by malonadehyde. Superoxide anion can enter into erthrocytes via anion channels, resulting in the formation of methemoglobin and the ultimate lysis of erythrocytes (Weiss, S. J.: J. Biol. Chem. 225: 9912-9917, 1980). Sickle RBCs spontaneously generate sixty percent greater quantities of superoxide and approximately 75% more hydrogen peroxide when compared with controls (Hebbel, R. P., et al.: J. Clin. Invest., vol. 70, p. 1253-1259, 1982). Superoxide dismutase is increased by about 50%, glutathione peroxidase and catalase were decreased by approximately 50% and 29% respectively. Glutathione and vitamin E levels were significantly reduced. It is postulated that by increasing both bone narrow and serum antioxidant levels that free radicals produced by sickled RBCs would be markedly reduced. Accordingly, maintenance/increase of antioxidant potential by administering the compositions of the present invention is useful to prevent or treat anemia-mediated injury.

Diabetes

Diabetes mellitus (DM) is a common disease affecting over 124 million individuals worldwide. DM is associated with high risk of atherosclerosis and renal, neural, and ocular damage. Oxidative stress results from a cell or tissue failing to detoxify the free radicals that are produced during metabolic activity. Diabetes is characterized by chronic hyperglycemia that produces dysregulation of cellular metabolism. Vincent and coworkers have suggested that diabetes overloads glucose metabolic pathways, resulting in excess free radical production and oxidative stress (Vincent et al., Endocr Rev. August; 25(4):612-28 (2004). Vincent and coworkers have presented evidence to support the idea that both chronic and acute hyperglycemia cause oxidative stress in the peripheral nervous system that can promote the development of diabetic neuropathy. Proteins that are damaged by oxidative stress have decreased biological activity leading to loss of energy metabolism, cell signaling, transport, and, ultimately, to cell death. Examination of the data from animal and cell culture models of diabetes, as well as clinical trials of antioxidants, strongly implicates hyperglycemia-induced oxidative stress in diabetic neuropathy. Vincent et al., concluded that superior antioxidative therapies remains essential for the prevention of neuropathy in diabetic patients (Vincent et al., Endocr Rev., August; 25(4): 612-28 (2004). The maintenance/increase of antioxidant potential by administering the compositions of the invention to a subject can, therefore, prevent or treat diabetes-related, ROS-mediated tissue damage.

Pasaoglu and coworkers, investigated lipid peroxidation, resistance of plasma and red blood cells to oxidation, and antioxidant defense system in erythrocytes and sera in patients with type 2 diabetes mellitus (Pasaoglu et al., Tohoku J Exp Med., July; 203(3):211-8 (2004). One group included newly diagnosed 20 patients and the other included 20 patients treated with oral antidiabetic agents (OAD). Twenty healthy subjects served as controls. Serum and red blood cell malondialdehyde (MDA), glutathione (GSH), resistance to oxidation, and plasma thiol (total -SH) levels were measured. In addition, glycated hemoglobin, serum fructosamine, uric acid, total protein, total cholesterol, triglyceride and glucose levels were determined. Although newly diagnosed patients had higher serum and erythrocyte MDA levels than those of controls, the highest levels of MDA were determined in patients treated with OAD. MDA levels after exposing to oxidation increased in OAD group more than in newly diagnosed patients. Total -SH and erythrocyte GSH levels of the both diabetic groups were lower than controls. These results showed that serum and erythrocyte lipid peroxidation was increased in diabetic patients. The sera of the patients showed a decreased resistance against oxidation. Pasaoglu and coworkers proposed that the effect of increased free radicals may be prevented by antioxidant systems in early stages of type 2 diabetes but in advanced stages this relationship is impaired owing to decreased antioxidant activity. Decreased red blood cell GSH and serum total -SH levels may be due to a compensation mechanism of the antioxidants. The maintenance/ increase of antioxidant potential by administering the compositions of the invention to a subject can, therefore, prevent or treat diabetes-related (e.g., diabetes type-2), ROS-mediated tissue damage.

Administration of the antioxidant enzymes superoxide dismutase (SOD) and catalase prevented destruction of islet allografts in NOD mice (Nomikos et al., Immunol Cell Biol 67:85-87 (1989)). Furthermore, the antioxidant probucol was shown to reduce the diabetes incidence and to delay diabetes onset in the BB rats (Drash A L et al., Am J Cardiol, 62:27B-30B (1988)). Tabatabaie and coworkers have demonstrated that chronic administration of the free radical scavenger phenyl-N-tert-butylnitrone (PBN) inhibits STZ-induced diabetes in mice (Tabatabaie et al., FEBS Lett, 407:148-152 (1997)). The low level of antioxidant enzymes such as SOD, catalase, and glutathione peroxidase in the islets is another indication that β-cells are exceptionally vulnerable to oxidative damage (Lenzen et al., Free Radical Biol. Med., 20:463-466 (1996)).

ROS generation, evidenced by the formation of lipid peroxidation products, is believed to be the ultimate cause of cytokine-mediated death of β-cells in isolated islets (Rabinovitch et al., J. Clin. Endocrinol. Metab., 81:3197-3202 (1996)). Tabatabaie and coworkers recently demonstrate the formation of free radicals in the pancreatic islets as a result of cytokine treatment using EPR spectroscopy (Tabatabaie et al., Diabetes, August. (2003)). Based on their studies, Tabatabaie and coworkers concluded that free radicals have a role in the pathogenesis of type 1 diabetes through β-cell cytokine-mediated free radical generation in the pancreatic Islets (Tabatabaie et al., Diabetes, August. (2003)). The maintenance/increase of antioxidant potential by administering the compositions of the invention to a subject can, therefore, prevent or treat diabetes-related (e.g., diabetes type-1), ROS-mediated tissue damage.

Pharmaceutical Compositions and Formulations

The compositions of the present invention can be used in beverages, tonics, infusions, or foodstuffs alone, or in combination with other dietary supplements or therapeutics. The compositions of the invention can be used alone or further formulated with pharmaceutically acceptable compounds, vehicles, excipients or adjuvants with a favorable delivery profile, i.e., suitable for delivery to a subject. Such compositions typically comprise the compositions of the invention and a pharmaceutically acceptable carrier. As used herein, "pharmaceutically acceptable carrier" is intended to include any and all solvents, dispersion media, coatings, antibacterial and antifungal compounds, isotonic and absorption delaying compounds, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include oral, intravenous, intraperitoneal, subcutaneous, intramuscular, intraarticular, intraarterial, intracerebral, intracerebellar, intrabronchial, intrathecal, topical, and aerosol route. The pH can be adjusted with acids or bases, such as hydrochloric acid or sodium hydroxide. Oral compositions generally include an inert diluent or an edible carrier. They can be enclosed in gelatin capsules, caplets or compressed into tablets. For the purpose of oral therapeutic administration, the compositions of the invention can be incorporated with one or more excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring. Excipients can also include, but are not limited to, e.g., calcium carbonate; croscarmellose sodium; dicalcium phosphate; magnesium stearate; microcrystalline cellulose; modified cellulose; silica; and stearic acid.

The compositions of the invention can also be prepared as pharmaceutical compositions in the form of suppositories (e.g., with conventional suppository bases such as cocoa butter and other glycerides) or retention enemas for rectal delivery.

In one embodiment, the compositions of the invention are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the composition of the invention and the particular therapeutic effect to be achieved, and the limitations inherent in the art of compounding such an active compound for the treatment of individuals. The pharmaceutical compositions can be included in a container, pack, or dispenser together with instructions for administration.

The present compositions may be provided as a single dose, however, it is preferred that the compounds be administered in multiple doses. Particularly preferred are intermittent doses, such as twice daily or once daily doses. However beneficial effects are still seen with more sporadic intermittent doses, e.g., once every 36, 48, 60 or 72 hours, or once per week. Duration of treatment will depend on the disorder being treated. For example, as discussed herein, an average 24% decrease of serum CRP levels was observed in human subjects treated intermittently for a 30 day period with the present compositions. Further decrease in serum CRP levels was observed to continue during the 90 day period of the study. Extrapolating this information to a suggested dosage regimen, one week may be sufficient to treat inflammation in post operative surgical patients, whose serum CRP levels usually peak in three days follow surgery, and naturally decline shortly thereafter. Alternatively, chronic conditions such as arthritis or atherosclerosis may require long term therapy over many years. A medical professional will be able to determine dosage levels and intervals in view of the teachings provided herein.

The invention is further defined by reference to the following examples, which are not meant to limit the scope of the present invention. It will be apparent to those skilled in the art that many modifications, both to the materials and methods, may be practiced without departing from the purpose and interest of the invention.

EXAMPLES

Example 1

Herbal Compositions of the Invention Alter Antioxidant Enzymes and Decrease Lipid Peroxidation in Wild Type C57BL/6J Mice I. General Purpose and Study Design The purpose of this study was to observe and effects of an herbal composition of the present invention on normal 4 week old wild type C57BL/6J mice. The exemplary herbal composition, Protandim I, is a dietary supplement containing eight herbal extracts, including, *B. monniera* extract, Milk Thistle extract 70-80%, Ashwagandha powder, Turmeric extract 95% curcumin, *Gotu Kola* powder, *Aloe vera* powder, Green tea (98% Polyphenols, 45% EGCG), and *Ginko biloba* leaf extract and specifically detailed below in Table 3.

TABLE 3

Composition of Protandim I.

| Active Ingredient | Amount | Percent Weight Total Active Ingredients |
|---|---|---|
| *Bacopa monniera* extract, 45% bacosides | 150 mg | 12.77 |
| Milk Thistle extract, 70-80% silymarin | 275 mg | 23.4 |
| Ashwagandha powder | 150 mg | 12.77 |
| Gotu kola power | 150 mg | 12.77 |
| Turmeric extract, 95% curcumin | 75 mg | 6.38 |
| Green tea 98% polyphenols, 45% EGCG | 75 mg | 6.38 |
| *Ginko biloba* leaf extract | 150 mg | 12.77 |
| *Aloe vera* powder | 150 mg | 12.77 |
| Total | 1175 mg | 100 |

The composition was mixed with the powdered diet, then pelleted. Mice were assigned to four groups as defined below in Table 4, receiving dosages ranging from 0 to 1, 3, or 10 times the anticipated human dosage. The estimated human dose for the present studies was 1175 mg/day or 16 mg/kgbw/day. However, in other embodiments of the invention the dosage to a subject is the amount required to yield the desired antioxidant effect.

TABLE 4

Mice received the indicated amounts of Protandim I

| | No. of mice | Diet | Dose µg/gbw/day | Protandim I mg/kg diet |
|---|---|---|---|---|
| Group 1 | 7 | Control | 0 | 0 |
| Group 2 | 8 | 1X | 16 | 100 |
| Group 3 | 7 | 3X | 48 | 300 |
| Group 4 | 8 | 10X | 160 | 1000 |
| TOTAL | 30 | | | |

The amount added was based on the assumption that the average mouse consumes 5 g/d. The amount of Protandim I composition received by each mouse in Group 2 was equivalent in mg/gbw to the anticipated human dosage for a 70 kg person. Group 3 received a 3-fold higher dosage of Protandim I and Group 4 received a 10-fold higher dosage of Protandim I. Mice were weighed at day 1 and day 23. After 23 days, the animals were sacrificed and tissues were harvested for analysis. The end points measured included activities of the major antioxidant enzymes SOD, CAT, and GPX in RBCs, liver, and brain. In addition, the extent of lipid peroxidation was assessed by measuring thiobarbituric acid reactive substances (TBARS) in plasma, liver, and brain.

Thiobarbituric acid reactive substances, or TBARS, were determined by the method of Ohkawa et al. (Ohkawa et al., Anal. Biochem., 95: 351-358 (1979). The reaction mixture (total volume of 1 ml) contained 50 µl of 8.1% sodium dodecyl sulfate, 0.375 ml of 20% acetic acid and 0.375 ml 0.8% thiobarbituric acid, and 200 µl of plasma or tissue homogenate supernate. The mixture was heated in boiling water for 1 hr, cooled with tap water and extracted with n-butanol/pyridine (15:1 v/v) by vortexing for 1-2 min. The mixture was then centrifuged at 500-1000 g for 10 min or until a good aqueous-organic phase separation occurred. The organic phase was removed and its absorbance at 532 nm was measured against a reaction mixture blank. A standard curve was prepared with 1,1,3,3-tetramethoxypropane, and TBARS are reported as molar equivalents.

Superoxide dismutase activity was determined by the method of McCord and Fridovich. McCord et al., J. Biol. Chem., 244: 6049-6055 (1969).

Catalase was assayed by the method of Beers and Sizer. Beers et al., J. Biol. Chem., 195, pp. 133-140 (1952). The disappearance of peroxide is followed spectrophotometrically at 240 nm. The incubation mixture (3 ml) contains 50 µl of sample supernatant in 0.05 M potassium phosphate (pH 7.0) and 0.02 M hydrogen peroxide. The decrease in absorbance recorded at 240 nm for 2 min. The rate of decrease in absorbance per min. is calculated from the initial (45 sec.) linear portion of the curve.

The value of 0.0394 cm$^2$/µmol is used as the extinction coefficient of $H_2O_2$ One unit of catalase is defined as the amount of enzyme which decomposes 1 µmol of $H_2O_2$/min at 250° C. at pH 7.0 under the specified conditions.

Glutathione peroxidase was assayed as described by Carrillo et al. (Carrillo et al., Life Sci., 48:517-521 (1991)).

II. Results

A. Assessment of Protandim I Toxicity

To assess any possible toxic effect of Protandim I supplementation, animals were weighed at the beginning and at the end of the study, and a percentage weight gain or loss was calculated for each. The most general indication of toxicity is "failure to thrive," which may manifest as a decreased rate of growth, or as an actual weight loss. FIG. 1 shows that supplementation actually caused modest but non-significant increases in growth rate. The absence of toxicity was evidenced as failure to thrive at any level of Protandim I supplementation, from the anticipated human dosage (1×) to a level of ten times that amount.

B. Protandim I Effect on SOD Activity

Figure 2:
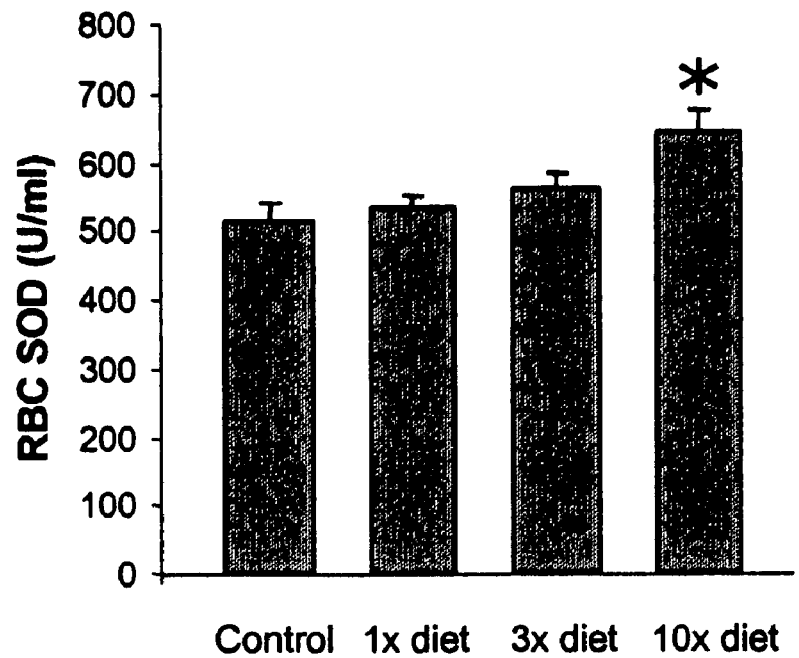
FIG. 2 shows graphs illustrating effect of Protandim I dietary supplement on murine red blood cell SOD concentration (RBC SOD). Panel A shows a graph of RBC SOD concentration (U/ml) observed in mice fed 1×, 3× and 10× dosage of Protandim I dietary supplement for 23 days. Panel B shows a graph of the percent increase in RBC SOD after 23 days on 1×, 3× and 10× dosage of Protandim I dietary supplement. An asterisk indicated statistical significance at p<0.02 level.
Figure 2:
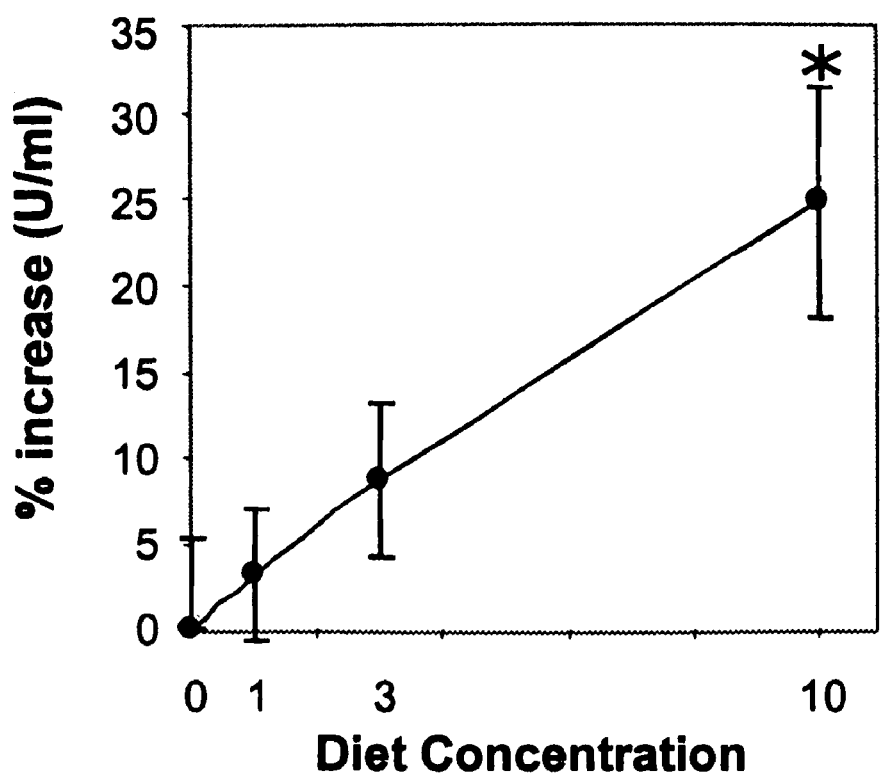

SOD activity was measured in the mice RBCs (FIG. 2), livers (FIG. 3) and brains (FIG. 4) to assess the effect of Protandim I on this enzyme. Animals supplemented with Protandim I showed a dose-dependent increase in RBC SOD activity, as seen in FIG. 2. A significant 25% increase was seen at the highest level of supplementation. It should be noted that mature, circulating RBC do not contain nuclei, and therefore are not capable of inducing new synthesis of enzymes once they enter the circulation. RBC have a circulating lifespan of 120 days. Thus, during the 23 day course of the experiment about 20% of the RBC would have been replaced by maturing reticulocytes from the bone marrow. As the older RBC are diluted out by the newly produced cells, one may predict that the increase in RBC SOD will proceed linearly with time until all cells have been replaced at 120 days. Therefore, the predicted final RBC SOD activities expected (after 120 days) would be about 16%, at 1×, 44%, at 3×, and 125% at 10× diet.

Figure 3:
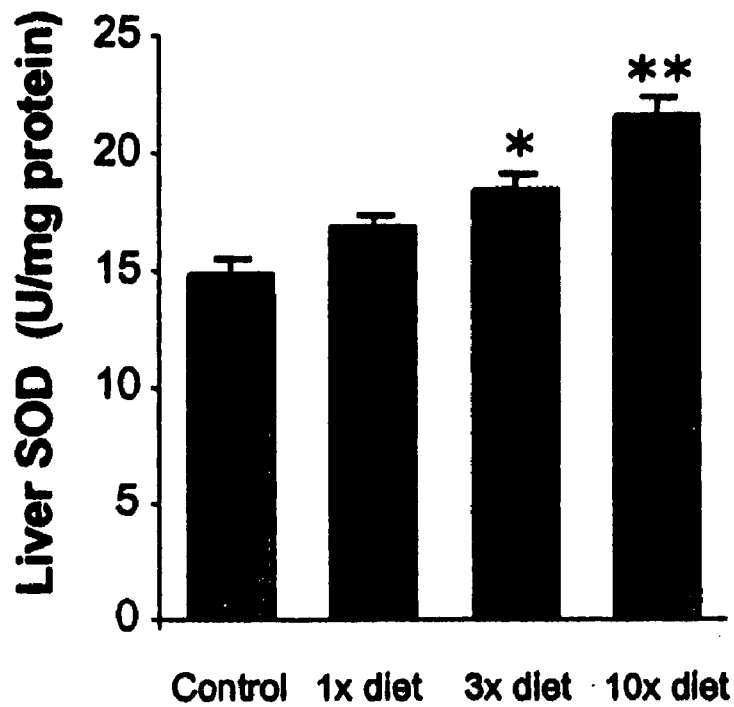
FIG. 3 shows graphs effect of Protandim I dietary supplement on murine liver SOD concentration. Panel A shows a graph of liver SOD concentration (U/mg protein) observed in mice fed for 23 days on 1×, 3× and 10× dosage of Protandim I dietary supplement. Panel B shows a graph of the percent increase in liver SOD after 23 days on 1×, 3× and 10× dosage of Protandim I dietary supplement. An asterisk indicates statistical significance at p<0.02 level. A double asterisk indicates statistical significance at p<0.0001 level.
Figure 3:
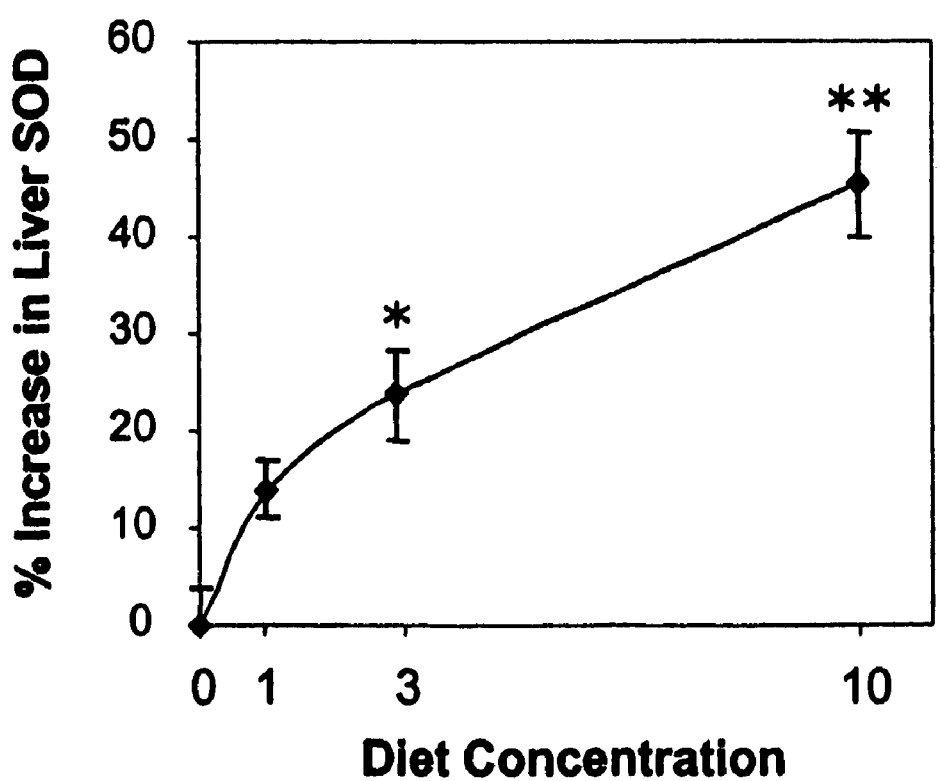
Figure 4:
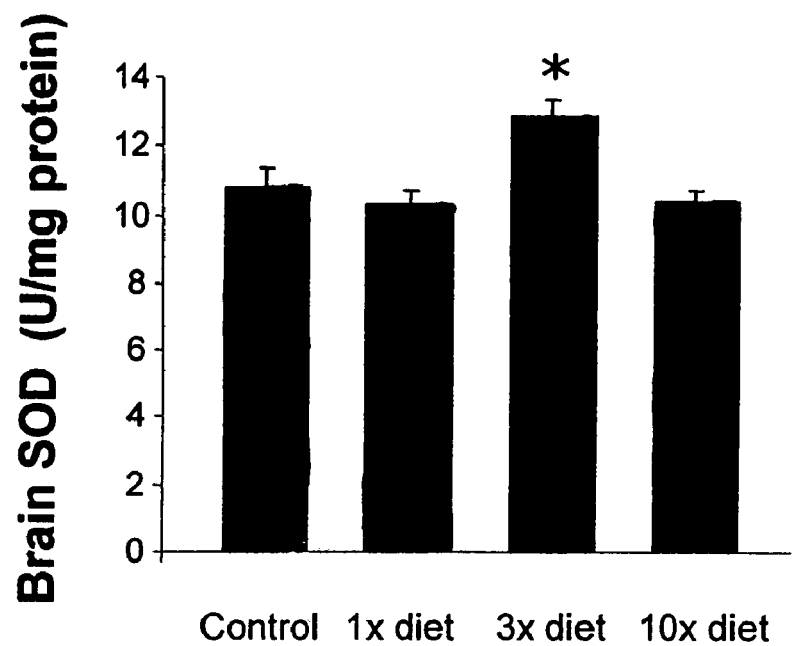
FIG. 4 shows graphs illustrating effect of Protandim I dietary supplement on murine brain SOD concentration. Panel A shows a graph of brain SOD concentration (I/mg protein) observed in mice fed 1×, 3× and 10× dosage of Protandim I dietary supplement for 23 days. Panel B shows a graph of the percent change in brain SOD after 23 days on 1×, 3× and 10× dosage of Protandim I dietary supplement. An asterisk indicates statistical significance at p<0.02 level.
Figure 4:
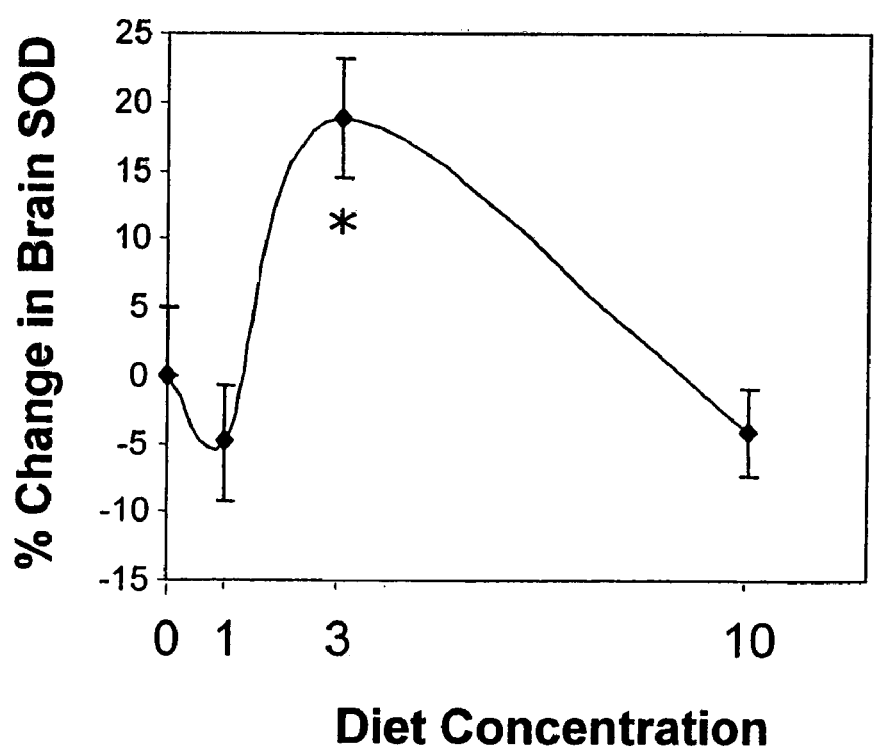

As detailed in FIG. 3, a dose-dependent increase in liver SOD activity was observed. As shown in the figure, a significant increase was seen at all levels of supplementation: 13% at 1×, 23% at 3×, and 45% at 10× diet. Also, a significant increase in brain SOD activity was seen, but only at the 3× level of Protandim I (FIG. 4). The percentage increase was about 20%.

C. Protandim I Effect on CAT Activity

Figure 5:
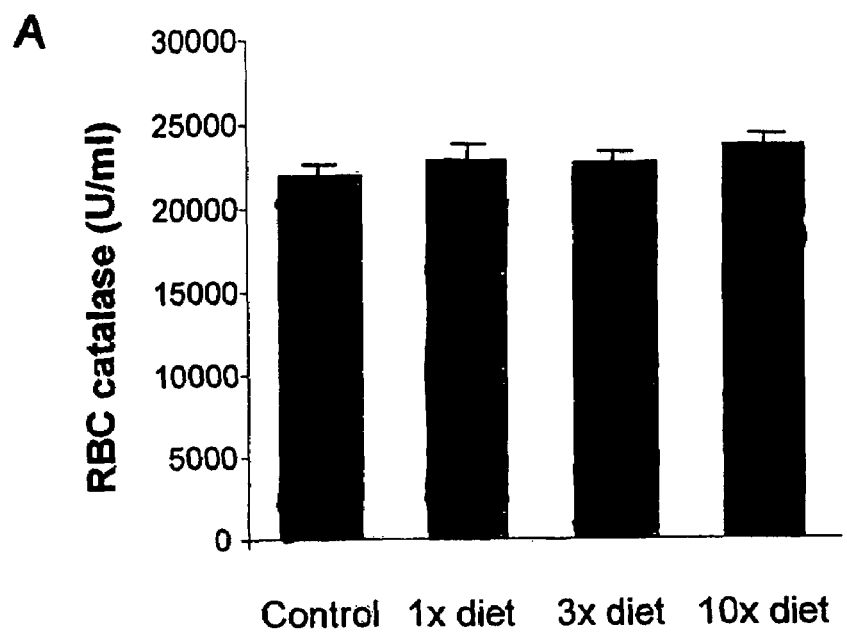
FIG. 5 shows graphs illustrating effect of Protandim I dietary supplement on murine red blood cell catalase concentration (RBC CAT). Panel A shows a graph of RBC CAT concentration (U/ml) observed in mice fed 1×, 3× and 10× dosage of Protandim I dietary supplement for 23 days. Panel B shows a graph of the percent increase in RBC CAT after 23 days on 1×, 3× and 10× dosage of Protandim I dietary supplement.
Figure 5:
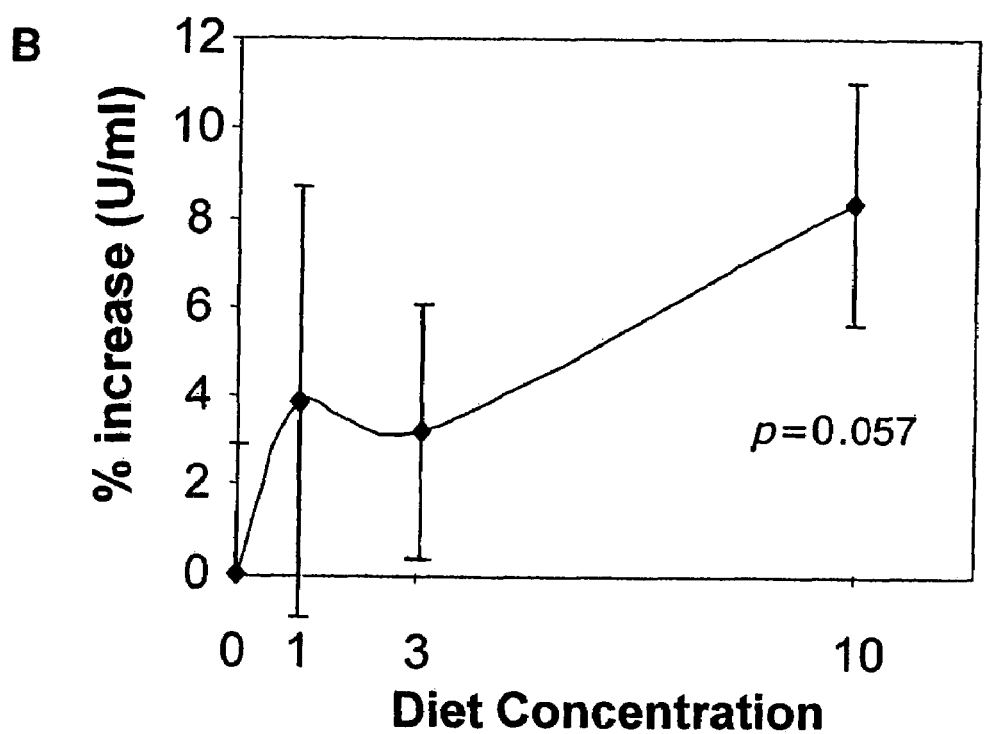

Animals supplemented with Protandim I showed little change in CAT. In RBC, there appeared to be a small dose-dependent increase, with an increase in the 10× group that approached statistical significance (p=0.057) (FIG. 5). Based on the turnover of RBC as discussed above, one can predict that the increase in RBC CAT would proceed linearly with time until all cells have been replaced at 120 days. Therefore, the predicted final RBC CAT activities expected after 120 days might approach 10% at 1×, 20% at 3×, and 40% at 10× diet.

Figure 6:
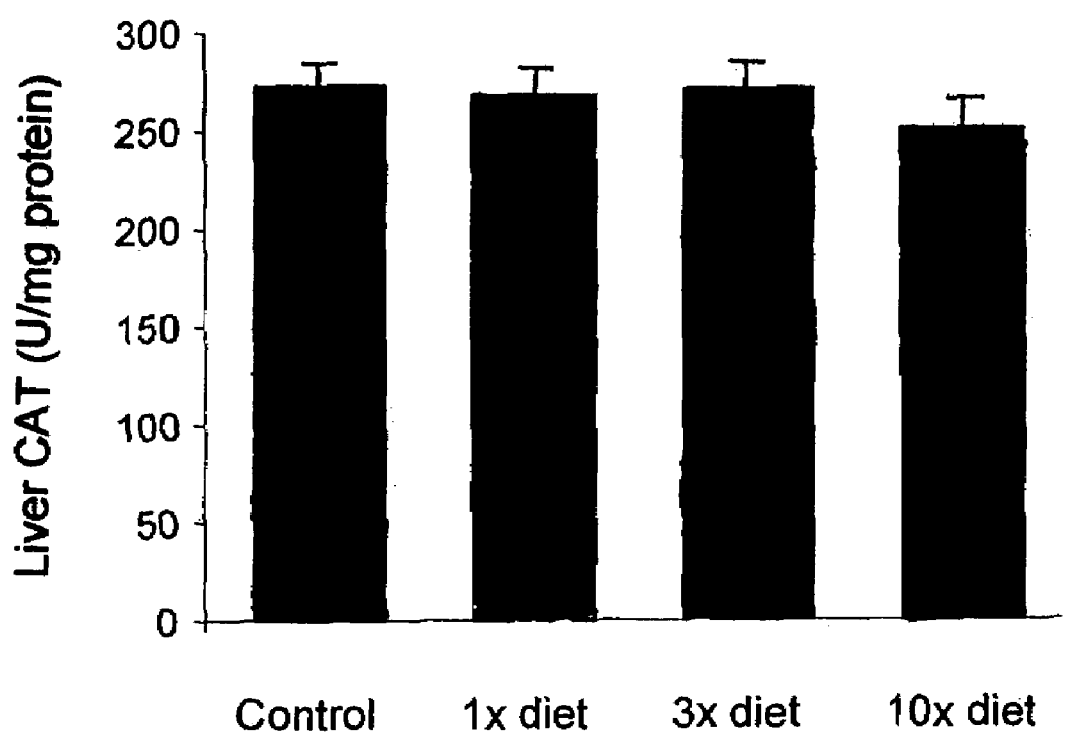
FIG. 6 is a graph illustrating effect of Protandim I dietary supplement on murine liver CAT concentration (U/mg protein) observed in mice fed 1×, 3× and 10× dosage of Protandim I dietary supplement for 23 days.

Liver CAT was unchanged on 1× and 3× diets, but showed a small non-significant decrease in activity on the 10× diet (FIG. 6). Brain normally contains very little catalase, and the small amounts detected did not change at any diet level.

D. Protandim I Effect on GPX Activity

Figure 7:
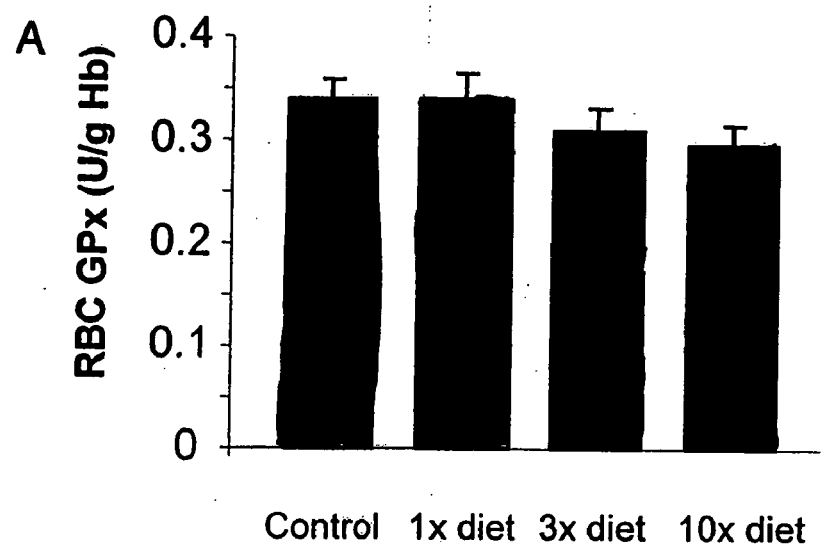
FIG. 7 shows graphs effect of Protandim I dietary supplement on murine red blood cell glutathione peroxidase concentration (RBC GPX). Panel A shows a graph of RBC GPX concentration (U/ml) observed in mice fed 1×, 3× and 10× dosage of Protandim I dietary supplement for 23 days. Panel B shows a graph of the percent change in RBC GPX (U/g Hb) after 23 days on 1×, 3× and 10× dosage of Protandim I dietary supplement.
Figure 7:
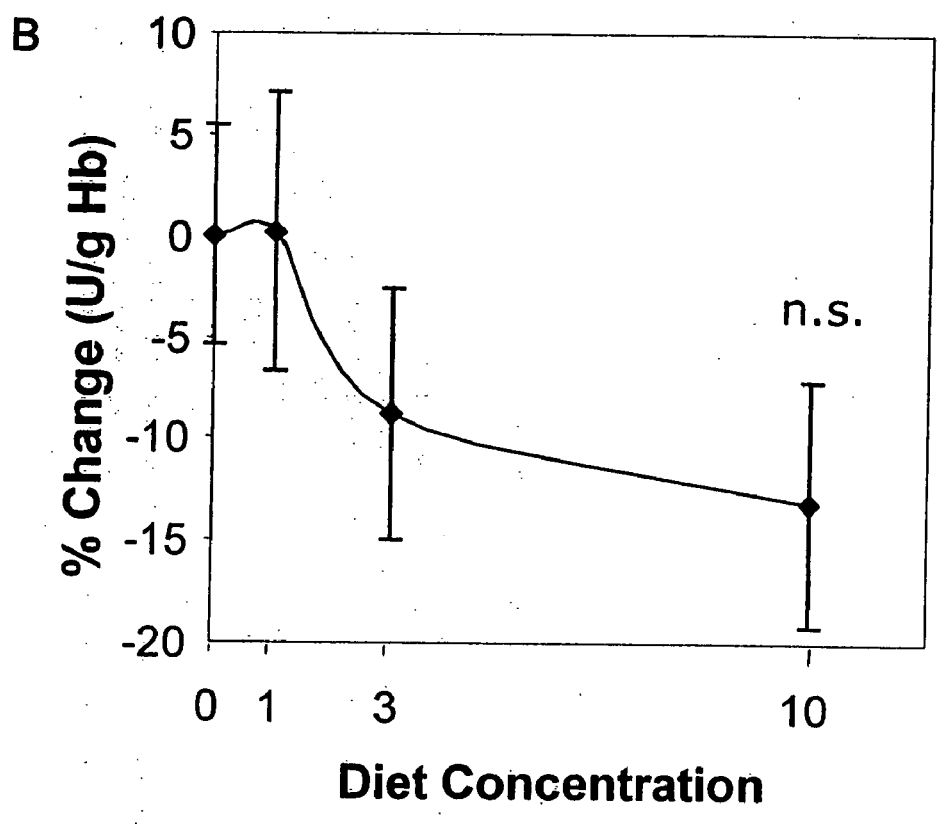
Figure 8:
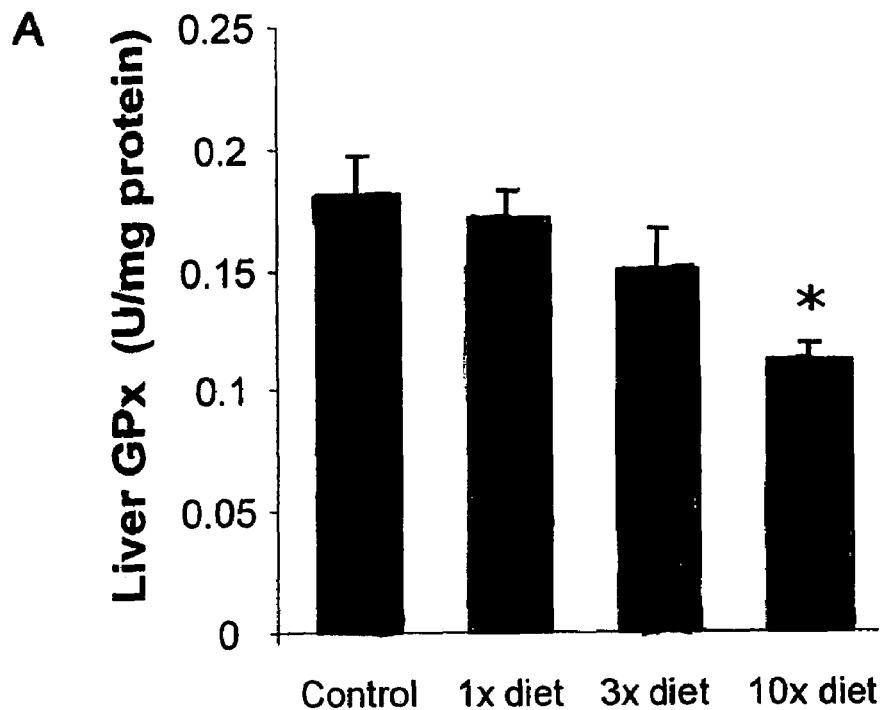
FIG. 8 shows graphs illustrating effect of Protandim I dietary supplement on murine liver GPX concentration. Panel A shows a graph of liver GPX concentration (U/mg protein) observed in mice fed 1×, 3× and 10× dosage of Protandim I dietary supplement for 23 days. Panel B shows a graph of the percent change in liver GPX after 23 days on 1×, 3× and 10× dosage of Protandim I dietary supplement. An asterisk indicated statistical significance at p<0.004 level.
Figure 8:
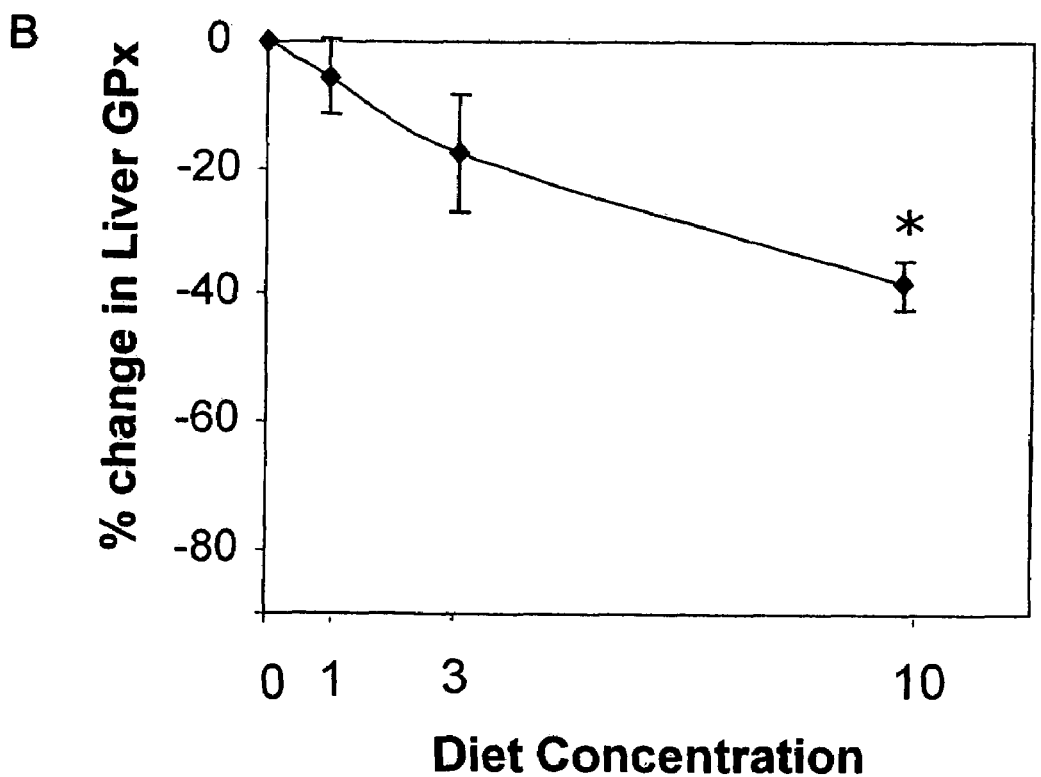
Figure 9:
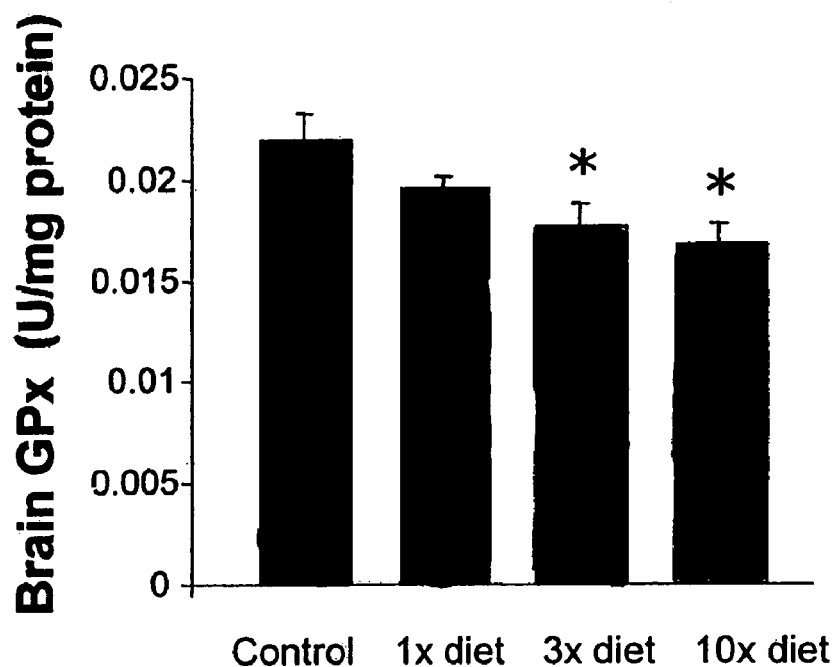
FIG. 9 shows graphs illustrating effect of Protandim I dietary supplement on murine brain GPX concentration. Panel A shows a graph of brain GPX concentration (U/mg protein) observed in mice fed 1×, 3× and 10× dosage of Protandim I dietary supplement for 23 days. Panel B shows a graph of the percent change in brain GPX after 23 days on various diets of a composition of the present invention. An asterisk indicates statistical significance at p<0.03 level.
Figure 9:
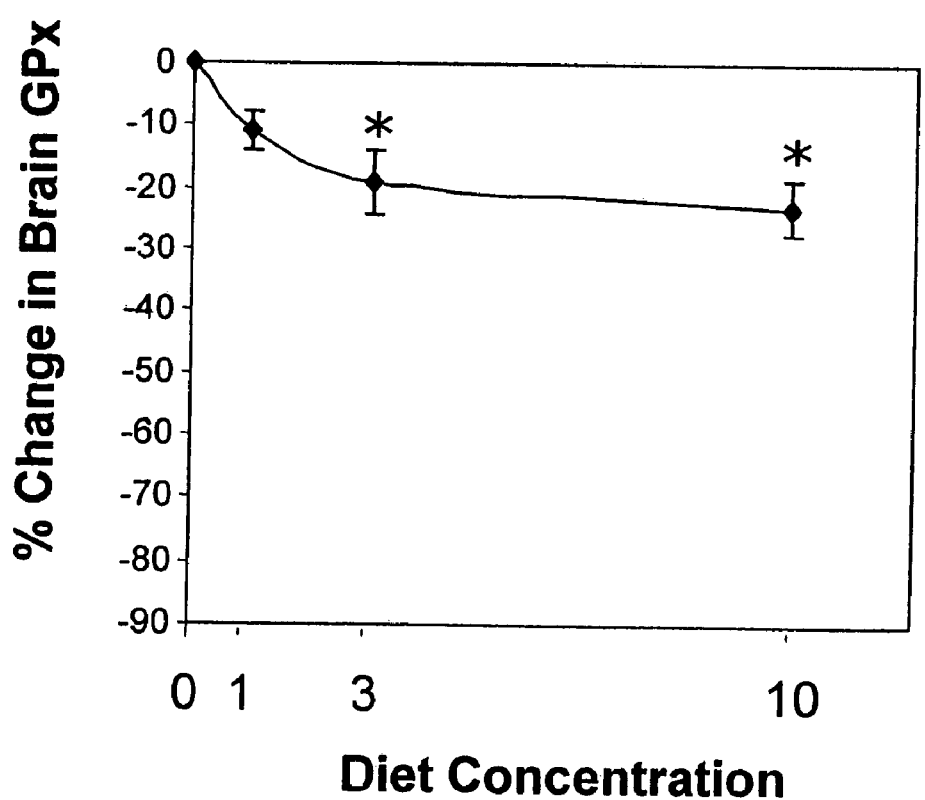

Animals supplemented with Protandim I showed an unexpected decrease in GPX activity. In RBC, there appeared to be a small dose-dependent decrease, with a 13% decrease in the 10× group that was not statistically significant (FIG. 7). Based on the turnover of RBC as discussed above, one can predict that the decrease in RBC GPX would proceed linearly with time until all cells have been replaced at 120 days. Therefore, the predicted decrease in RBC GPX activity expected after 120 days might approach 65% at 10× diet. There was a similar decrease in liver GPX that appeared to be dose-dependent, with a 40% decrease in the 10× group that was statistically significant at p<0.004 (FIG. 8). Brain followed a similar pattern, with significant decreases of 19% at 3× (p<0.03) and 23% at 10× (p=0.01 (FIG. 9).

E. Protandim I Effect on Lipid Peroxidation (TBARS)

Figure 10:
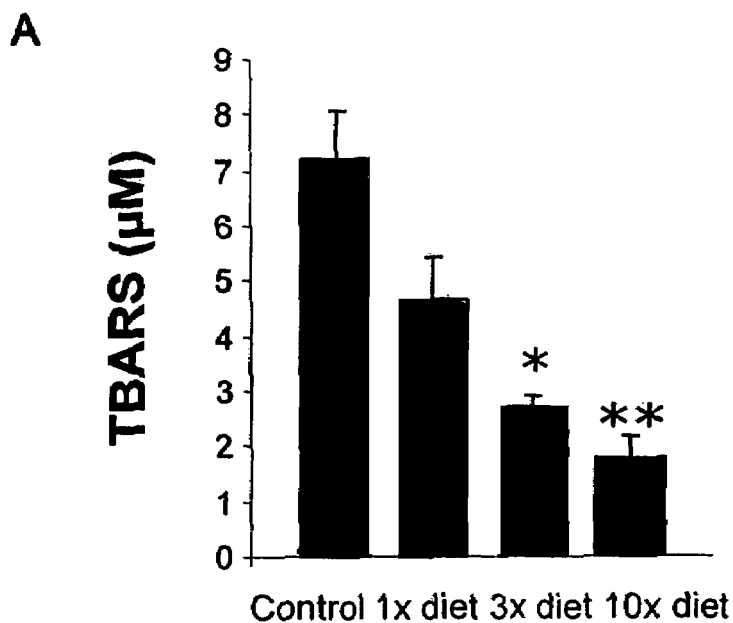
FIG. 10 shows graphs illustrating effect of Protandim I dietary supplement on murine plasma lipid peroxidation products measured as TBARS. Panel A shows a graph of plasma TBARS concentration (μM) observed in mice fed 1×, 3× and 10× dosage of Protandim I dietary supplement for 23 days. Panel B shows a graph of the percent change in plasma TBARS after 23 days on 1×, 3× and 10× dosage of Protandim I dietary supplement. A single asterisk indicates statistical significance at p<0.004 level. A double asterisk indicates statistical significance at the p<0.0004 level.
Figure 10:
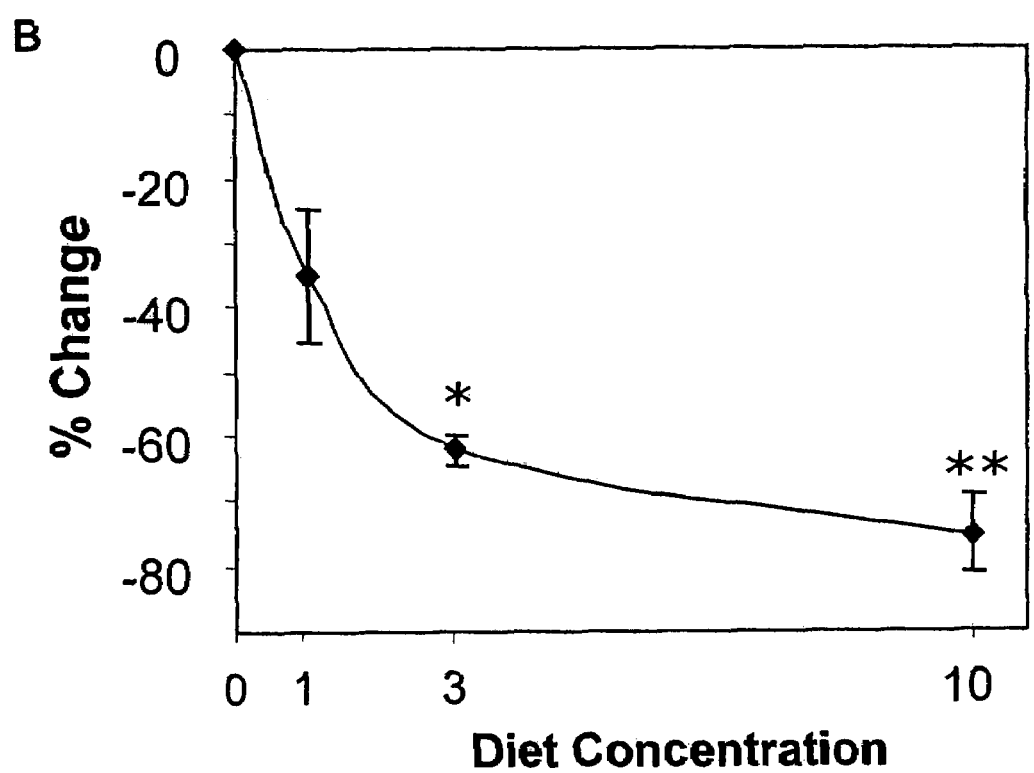

One objective of Protandim treatment is to decrease oxidative stress. Our endpoint to assess oxidative stress in this study was TBARS. Animals supplemented with Protandim I showed dramatic and highly significant decreases in TBARS in all tissues studied. In plasma, there was a dose-dependent decrease: 135% decrease in animals on the 1× diet; 62# on the 3× diet; and 75% on the 10× diet. The changes in the 3× and 10× groups had high statistical significance: p=0.004 and p=0.0004, respectively (FIG. 10).

Figure 11:
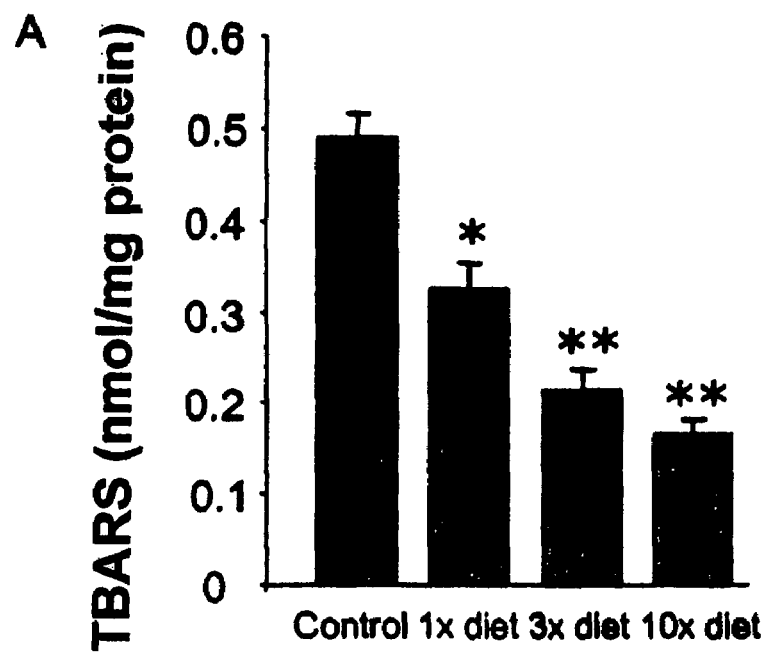
FIG. 11 shows graphs illustrating the effect of diets of a composition of the present invention on murine liver lipid peroxidation products measured as TBARS. Panel A shows a graph of liver TBARS concentration (nmol/mg protein) observed in mice fed 1×, 3× and 10× dosage of Protandim I dietary supplement for 23 days. Panel B shows a graph of the percent change in liver TBARS after 23 days on 1×, 3× and 10× dosage of Protandim I dietary supplement. A single asterisk indicates statistical significance at p=0.001 level. A double asterisk indicates statistical significance at the p<0.00001 level.
Figure 11:
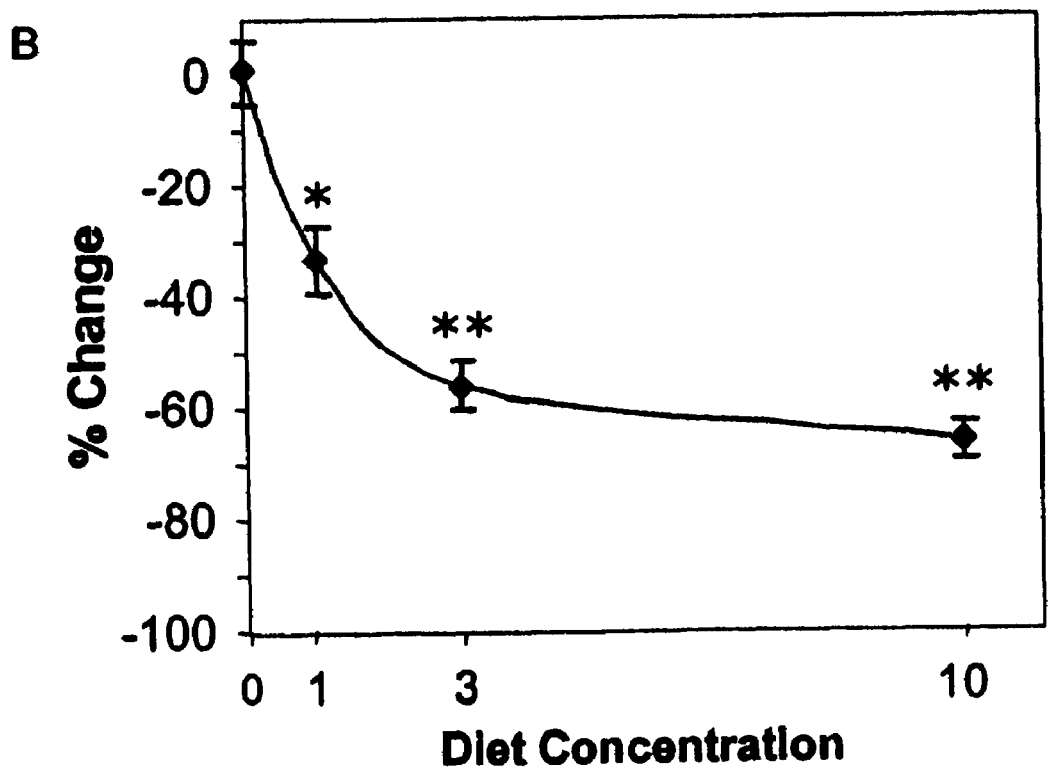
Figure 12:
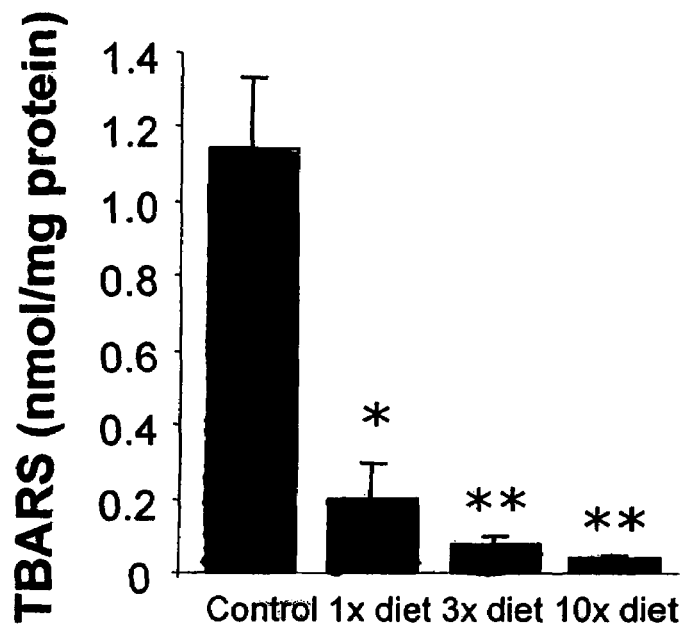
FIG. 12 shows graphs illustrating effect of Protandim I dietary supplement on murine brain lipid peroxidation products measured as TBARS. Panel A shows a graph of brain TBARS concentration (nmol/mg protein) observed in mice fed 1×, 3× and 10× dosage of Protandim I dietary supplement for 23 days. Panel B shows a graph of the percent change in brain TBARS after 23 days 1×, 3× and 10× dosage of Protandim I dietary supplement. A single asterisk indicates statistical significance at p<0.004 level. A double asterisk indicates statistical significance at the p<0.0001 level.
Figure 12:
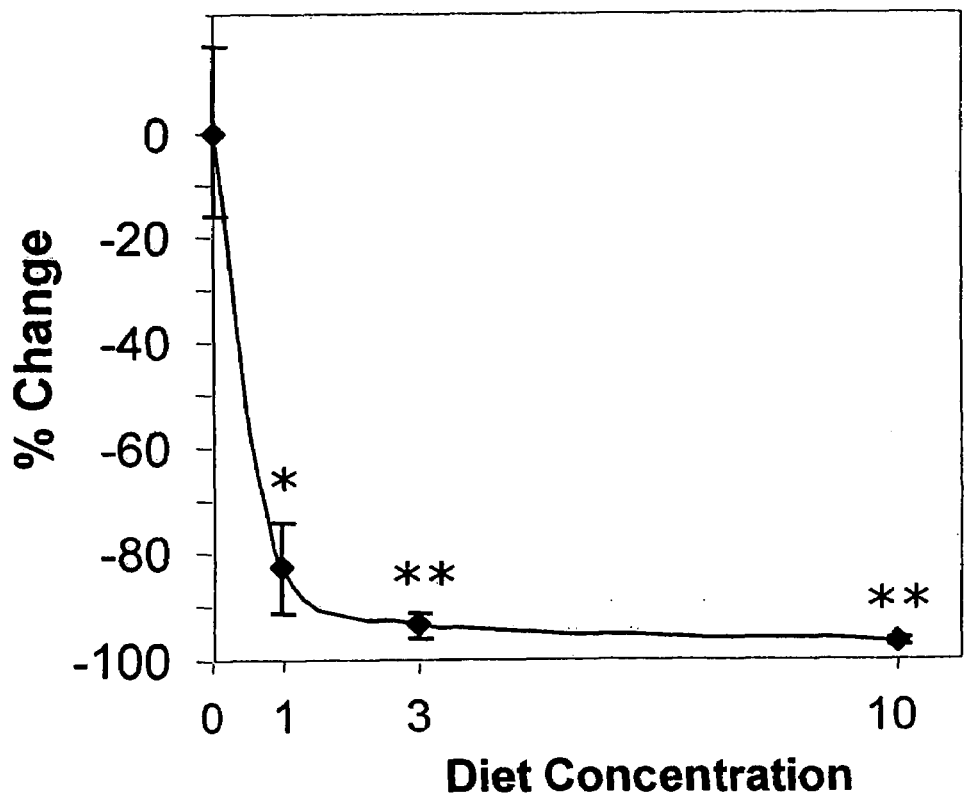

As shown in FIG. 11, in liver homogenates, there was a similar dose-dependent decrease: a 34% decrease in animals on the 10× diet; 56% on the 3× diet; and 66% on the 10× diet. The changes in this tissue had high statistical significance at all there diet concentrations (FIG. 11). In brain homogenates, the effect of Protandim I was even more striking: an 83% decrease was seen on the 1× diet (p<0.004); 94% on the 3× diet (p<0.0001; and 97% on the 10× diet (p<=0.0001) (FIG. 12).

III. Summary of Protandim I's Effects

The present study established that herbal compositions of the present invention, e.g., Protandim I (as defined in Table 3), are a safe and effective way of decreasing oxidative stress. The dosage defined as "1×" (16 mg/kg body weight) seems perfectly positioned for safety and efficacy. The major unexpected finding of the study was that, of the three antioxidant enzymes measured, only SOD was clearly induced. CAT was unaffected, and GPX levels actually showed a significant decline. This study was based on claims in the literature that seven of the eight herbal ingredients upregulated SOD (Bhattacharya et al., Phytother, Res., 14:174-179 (2000); Soto et al., Comp Biochem. Physiol C. Toxicol. Pharmacol., 136:205-212 (2003); Bhattacharya et al., Indian J. Exp. Biol., 35:236-239 (1997); Bridi et al., Phytother. Res., 15:449-451 (2001); Luczaj et al., J. Toxicol. Environ. Health A, 67:595-606 (2004); Reddy et al., Food Chem., Toxicol., 32:279-283 (1994); Singh et al., Phytomedicine, 7:209-219 (2000); Naidu et al., Indian J. Exp. Biol., 40:894-900 (2002)), and that all eight upregulated CAT, and GPX (Bhattacharya et al., Phytother, Res., 14:174-179 (2000); Soto et al., Comp Biochem. Physiol C. Toxicol. Pharmacol., 136:205-212 (2003); Bhattacharya et al., Indian J. Exp. Biol., 35:236-239 (1997); Bridi et al., Phytother. Res., 15:449-451 (2001); Luczaj et al., J. Toxicol. Environ. Health A, 67:595-606 (2004); Reddy et al., Food Chem., Toxicol., 32:279-283 (1994); Singh et al., Phytomedicine, 7:209-219 (2000); Naidu et al., Indian J. Exp. Biol., 40:894-900 (2002); Skukla et al., Phytother. Res., 13:50-54 (1999)).

Figure 13:
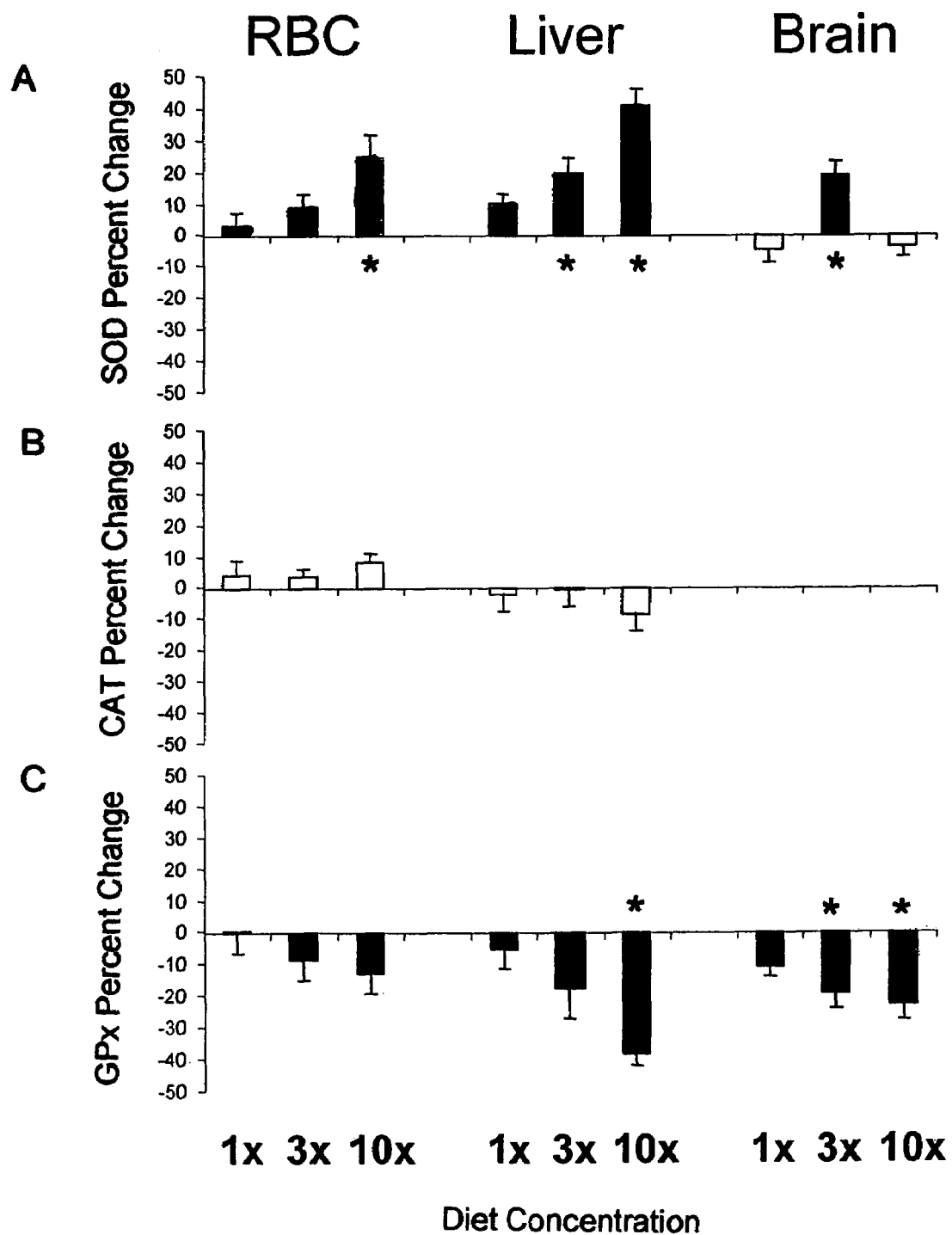
FIG. 13 shows graphs illustrating effect of Protandim I dietary supplement on murine SOD, CAT and GPX in various tissues. Panel A shows a graph of the percent change in SOD observed in RBC, liver and brain of mice fed 1×, 3× and 10× dosage of Protandim I dietary supplement for 23 days. Panel B shows a graph of the percent change in CAT observed in RBC and liver of mice fed 1×, 3× and 10× dosage of Protandim I dietary supplement for 23 days. Panel C shows a graph of the percent change in GPX observed in RBC, liver and brain of mice fed 1×, 3× and 10× dosage of Protandim I dietary supplement for 23 days. A single asterisk indicates statistical significance at relative to the control diet.

FIG. 13 summarizes the Protandim-induced changes in antioxidant enzymes in blood, liver, and brain where clear and distinctly different patterns emerge. SOD was induced in a dose-dependent fashion, with the only departure from the pattern being seen in brain with the 10× diet. As may be seen in FIG. 14, brain TBARS was, in fact, nearly totally eliminated on the 10× diet, suggesting that protection from oxidative stress was maximal.

Figure 14:
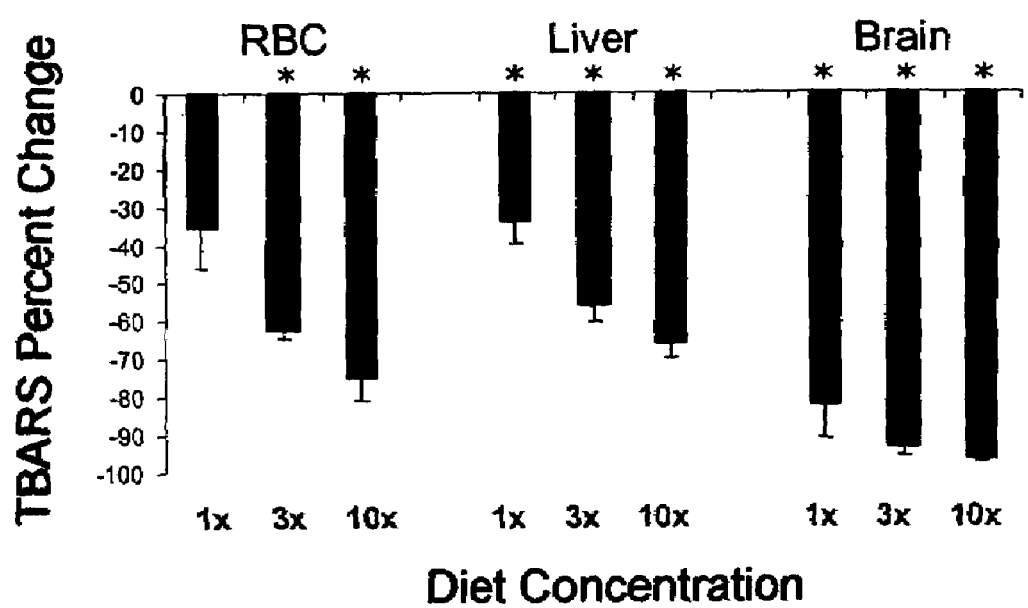
FIG. 14 is a graph illustrating the effect of Protandim I dietary supplement on murine lipid peroxidation in various tissues. The graph shows the percent change in lipid peroxidation measured as TBARS in RBC, liver and brain of mice fed 1×, 3× and 10× dosage of Protandim I dietary supplement for 23 days. A single asterisk indicates statistical significance at relative to the control diet.

FIG. 14 summarizes the effect of each Protandim I diet level on lipid peroxidation in each of the three tissues examined. There was a strong dose-dependency apparent, with no suggestion of any paradoxical increase in lipid peroxidation due to the well-established bell-shaped curve seen with the effect of increasing SOD concentration on rate of lipid peroxidation. This is an important safety consideration. While it is clear that increasing SOD will be beneficial to individuals experiencing high oxidative stress, there was a possibility that increased SOD would become problematic to healthy individuals with little oxidative stress. This study, therefore, was designed to examine the ability of Protandim I to decrease oxidative stress in young, normal mice, without causing a paradoxical increase in oxidative stress at the upper end of a ten-fold dosage range. Other compositions of the invention likely share the same positive health benefits when administered to a subject.

Example 2

Herbal Compositions of the Invention Alter Antioxidant Enzymes and Decreased Lipid Peroxidation in Human Subjects I. General Purpose and Design of Study The purpose of this study was to observe the effects of herbal compositions of the present invention on human subjects. An exemplary dietary supplement containing five herbal extracts, called Protandim II was administered to sixteen healthy human subjects ranging in age from 20 to 78 years old. The composition of Protandim II is shown below in Table 5.

TABLE 5

Composition of Protandim II.

| Active Ingredient | Amount | Percent Weight Total Active Ingredients |
| --- | --- | --- |
| B. monniera extract, 45% Bacosides | 150 mg | 22.2 |
| Milk Thistle extract, 70-80% Silymarin | 225 mg | 33.3 |
| Ashwagandha powder | 150 mg | 22.2 |
| Turmeric extract, 95% Curcumin | 75 mg | 11.1 |
| Green tea, 98% polyphenols, 45% EGCG | 75 mg | 11.1 |
| Total | 675 mg | 99.9 |

Subjects were assigned to two groups as defined in Table 6.

TABLE 6

Protandim II Dosing of Human Subjects

| | No. of subjects | Age range | Daily supplement of Protandim II |
| --- | --- | --- | --- |
| Group 1 | 12 | 20 to 78 | 675 mg |
| Group 2 | 4 | 29 to 66 | 338 mg |
| TOTAL | 16 | | |

Group 1 had twelve subjects who received the full daily Protandim II supplement of 675 mg in a single daily capsule for 120 days. At 0, 30, and 120 days, blood was taken by venipuncture for analysis. Group 2 had four additional participants who received one-half as much Protandim (i.e., half dose), or 338 mg in a single daily capsule for 30 days.

II. Methods

The end points measured in tissue from human subjects included activities of the major antioxidant enzymes SOD and CAT in RBCs. The extent of lipid peroxidation was assessed by measuring thiobarbituric acid reactive substances (TBARS) in plasma. In addition, uric acid was measured in plasma because it is believed to be an endogenous antioxidant of some importance, especially with regard to scavenging and neutralizing the oxidant peroxynitrite. If oxidative stress were decreased, one might expect a sparing effect on plasma uric acid levels. High sensitivity CRP was monitored as an indicator of inflammatory activity, and lipid profiles (total cholesterol, LDL, HDL, and triglycerides) were assessed.

Thiobarbituric acid reactive substances, or TBARS, were determined by the method of Ohkawa et al. (Ohkawa et al., Anal. Biochem., 95: 351-358 (1979). The reaction mixture (total volume of 1 ml) contained 50 µl of 8.1% sodium dodecyl sulfate, 0.375 ml of 20% acetic acid and 0.375 ml 0.8% thiobarbituric acid, and 200 µl of plasma or tissue homogenate supernate. The mixture was heated in boiling water for 1 hr, cooled with tap water and extracted with n-butanol/pyridine (15:1 v/v) by vortexing for 1-2 min. The mixture was then centrifuged at 500-1000 g for 10 min or until a good aqueous-organic phase separation occurred. The organic phase was removed and its absorbance at 532 nm was measured against a reaction mixture blank. A standard curve was prepared with 1,1,3,3-tetramethoxypropane, and TBARS are reported as molar equivalents.

Superoxide dismutase activity was determined by the method of McCord and Fridovich. McCord et al., J. Biol. Chem., 244: 6049-6055 (1969).

Catalase was assayed by the method of Beers and Sizer. Beers et al., J. Biol. Chem., 195, pp. 133-140 (1952). The disappearance of peroxide is followed spectrophotometrically at 240 nm. The incubation mixture (3 ml) contains 50 μl of sample supernatant in 0.05 M potassium phosphate (pH 7.0) and 0.02 M hydrogen peroxide. The decrease in absorbance recorded at 240 nm for 2 min. The rate of decrease in absorbance per min. is calculated from the initial (45 sec.) linear portion of the curve.

The value of 0.0394 cm2/μmol is used as the extinction coefficient of $H_2O_2$

One unit of catalase is defined as the amount of enzyme which decomposes 1 μmol of $H_2O_2$/min at 250° C. at pH 7.0 under the specified conditions.

High sensitivity C-reactive protein, uric acid, and lipid profile analyses (total cholesterol, LDL, HDL, triglycerides) were performed by the clinical chemistry laboratory of the University Hospital/University of Colorado Health Sciences Center, Denver, Colo.

Glutathione peroxidase was assayed as described by Carrillo et al. (Carrillo et al., Life Sci., 48:517-521 (1991)).

III. Results

A. Assessment of Protandim II Toxicity or Side Effects

All subjects were instructed to report any suspected adverse reaction or side effect (such as nausea, vomiting, headache, gastrointestinal discomfort, diarrhea, constipation, itching, etc.) to the investigators immediately, and to discontinue use of the supplement. No such reactions or side effects were reported. No toxicity or evidence of other unwanted pharmacological effects of Protandim II were noted at either level of supplementation.

B. Effect of Protandim II on Lipid Peroxidation and TBARS

One objective of Protandim II treatment was to decrease oxidative stress. Our endpoint to assess oxidative stress in this study was TBARS, which measures a family of lipid peroxidation products (mostly lipid hydroperoxides) which break down during the analysis to yield malondialdehyde, which reacts with thiobarbituric acid to yield the chromophore measured at 532 nm. The TBA assay has been somewhat controversial, criticized by some for lack of specificity because it yields higher values than gas chromatographic methods specific for malondialdehyde. The ability of the TBA test to collectively measure lipid peroxidation products, including precursors that will continue to break down to yield malondialdehyde, is a strength of the TBA assay. Gutteridge et al., J. Appl. Biochem., 5:293-299 (1983); Liu et al., Anal. Biochem. 245:161-166 (1997). It is clear that native fatty acids in the absence of lipid peroxides do not undergo significant peroxidation during the acid-heating stage of the TBA test. Gutteridge et al., J. Appl. Biochem., 5:293-299 (1983). Furthermore, the TBA test is the most widely used in the literature to assess lipid peroxidation, enabling easy comparison with the largest number of studies from other laboratories. In particular, a recent study found plasma TBARS to be a predictor of cardiovascular events in patients with established heart disease, independently of traditional risk factors and inflammatory markers. Walter et al., J. Am. Coll. Cardiol., 44:1996-2002 (2004).

Figure 15:
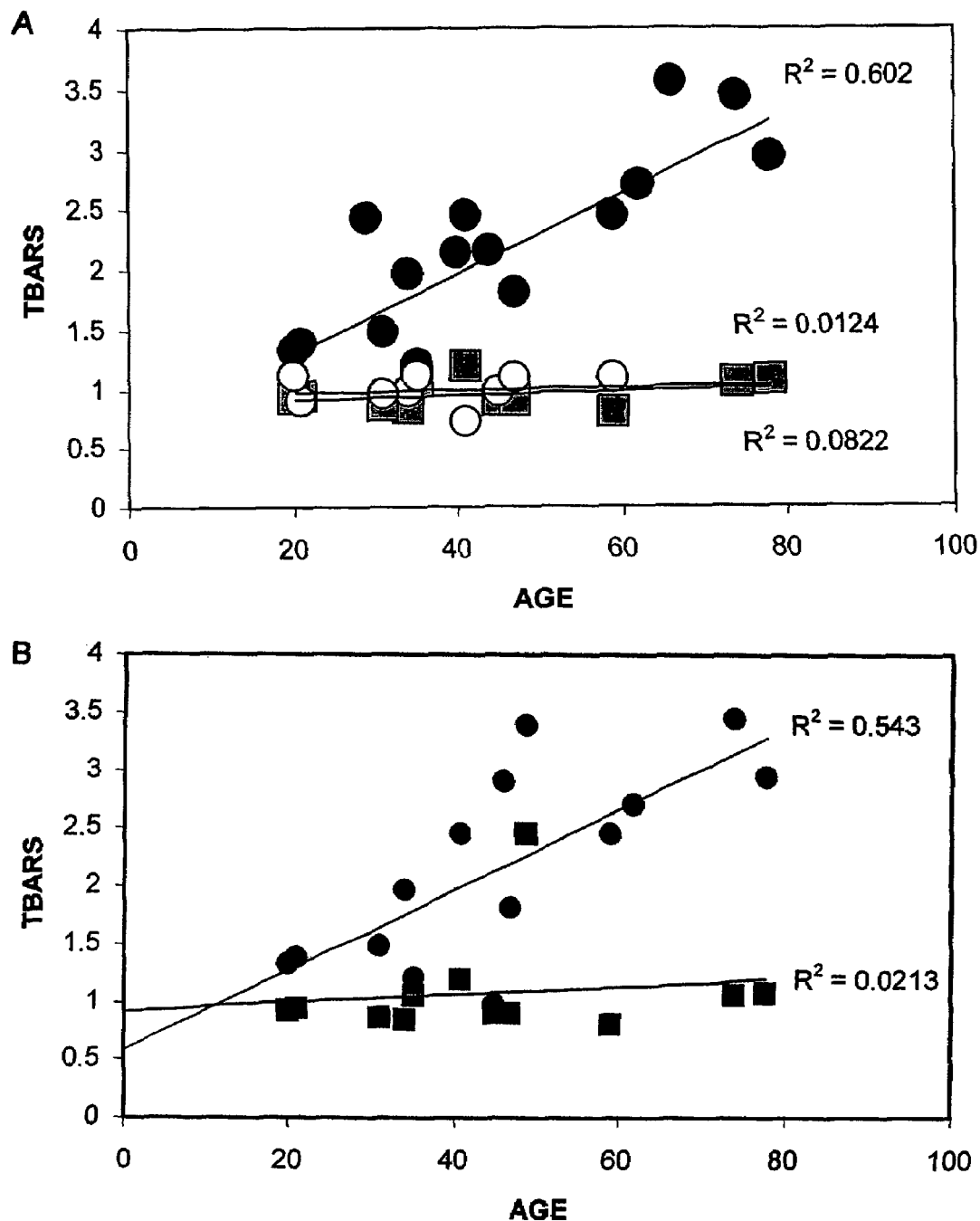
FIG. 15 is a graph showing response of human subjects to dietary supplementation with the herbal composition Protandim II. Panel A shows plasma TBARS level in human subjects prior to supplementation with Protandim II at 675 mg/day (closed circles), after 30 days of supplementation (gray squares), and after 120 days (open circles). The levels of plasma TBARS dropped an average of 51% (p<0.002) after 30 days of Protandim treatments (gray squares) the age-related increase in TBARS virtually disappeared. Panel B shows plasma TBARS level in normal subjects before supplementation with Protandim II showed a strong age-dependent increase in TBARS (circles). The levels of plasma TBARS dropped on average 51% (p<0.002) after 30 days of Protandim II (squares) supplementation, and the age-related increase in TBARS virtually disappeared.

FIG. 15 (panel A and panel B) illustrates the age-related increase in plasma TBARS in sixteen healthy human subjects ranging in age from 20 to 78 years old, prior to supplementation with Protandim II (solid circles). As shown in FIG. 15, panel A, while there is substantial scatter around the linear regression line, there is a strong correlation with age ($R^2$=0.602) with the oldest individuals showing values approximately three-fold higher than the youngest individuals. After supplementation with Protandim II for 30 days (675 mg/day, n=11), the values for plasma TBARS declined as shown by the gray squares. The scatter is remarkably less, and the correlation with age virtually disappears ($R^2$=0.082). After 30 days, the average TBARS concentration was 0.95±0.04 μM. Nine of these individuals were assayed after 120 days of supplementation (open circles), showing no further change (0.99±0.05 μM; $R^2$=0.012). All subjects showed decreased TBARS after 30 days on Protandim II. The age-related increase in lipid peroxidation products disappeared with Protandim II supplementation. The changes were maintained at 120 days, with results indistinguishable from those at 30 days.

C. Effect of Protandim II on SOD Activity

Figure 16:
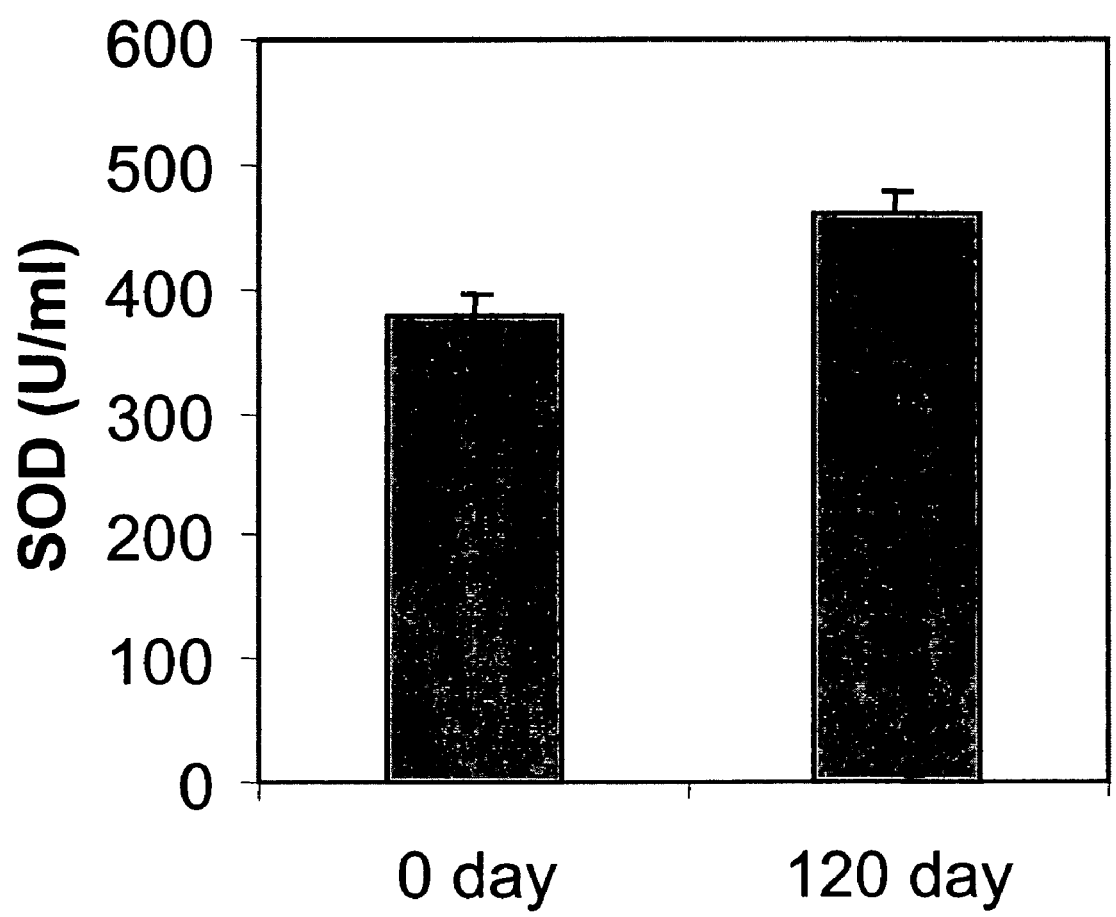
FIG. 16 is a graph illustrating the effect of Protandim II dietary supplementation on human SOD in RBCs.

Subjects supplemented with Protandim II showed a statistically significant increase of 22% (n=9, p=0.04) in erythrocyte SOD activity after 120 days of supplementation, as seen in FIG. 16. Erythrocyte SOD at day 0 was 378±17 U/ml and 460±18 U/ml by day 120. It should be noted that mature, circulating erythrocytes do not contain nuclei, and therefore are not capable of inducing new synthesis of enzymes once they enter the circulation. Erythrocytes have a circulating lifespan of 120 days. Thus, during the 120 day course of the experiment 100% of the red cells would have been replaced by maturing reticulocytes from the bone marrow.

D. Effect of Protandim II on CAT Activity

Figure 17:
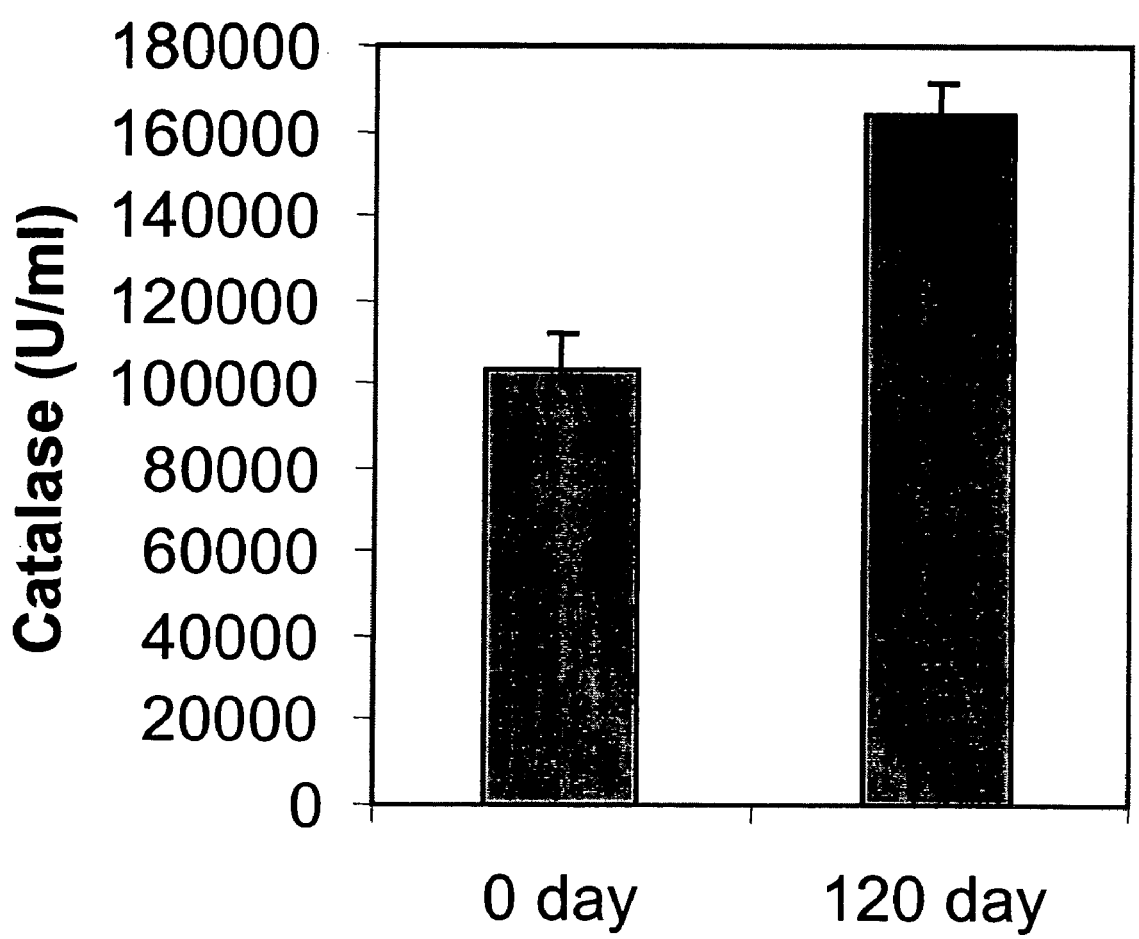
FIG. 17 is a graph illustrating the effect of Protandim II dietary supplementation on human CAT in RBCs.

Subjects supplemented with Protandim II showed a statistically significant increase of 57% (n=9, p=0.001) in erythrocyte CAT activity after 120 days of supplementation, as seen in FIG. 17. Erythrocyte CAT at day 0 was 104,000±8,000 U/ml and 163,000±8,000 U/ml by day 120. The same considerations regarding turnover and replacement of erythrocytes apply to catalase as discussed above for SOD.

E. Effect of Protandim II on Select Blood Parameters

Subjects supplemented with Protandim II showed an increase of 4.6% in plasma uric acid concentration after 30 days of supplementation, but this increase did not achieve statistical significance. Because uric acid serves as an endogenous antioxidant, it was anticipated that uric acid levels might rise as a result of increased SOD activity, which would lead to lower levels of peroxynitrite production. Uric acid is thought to scavenge the oxidant peroxynitrite.

Figure 18:
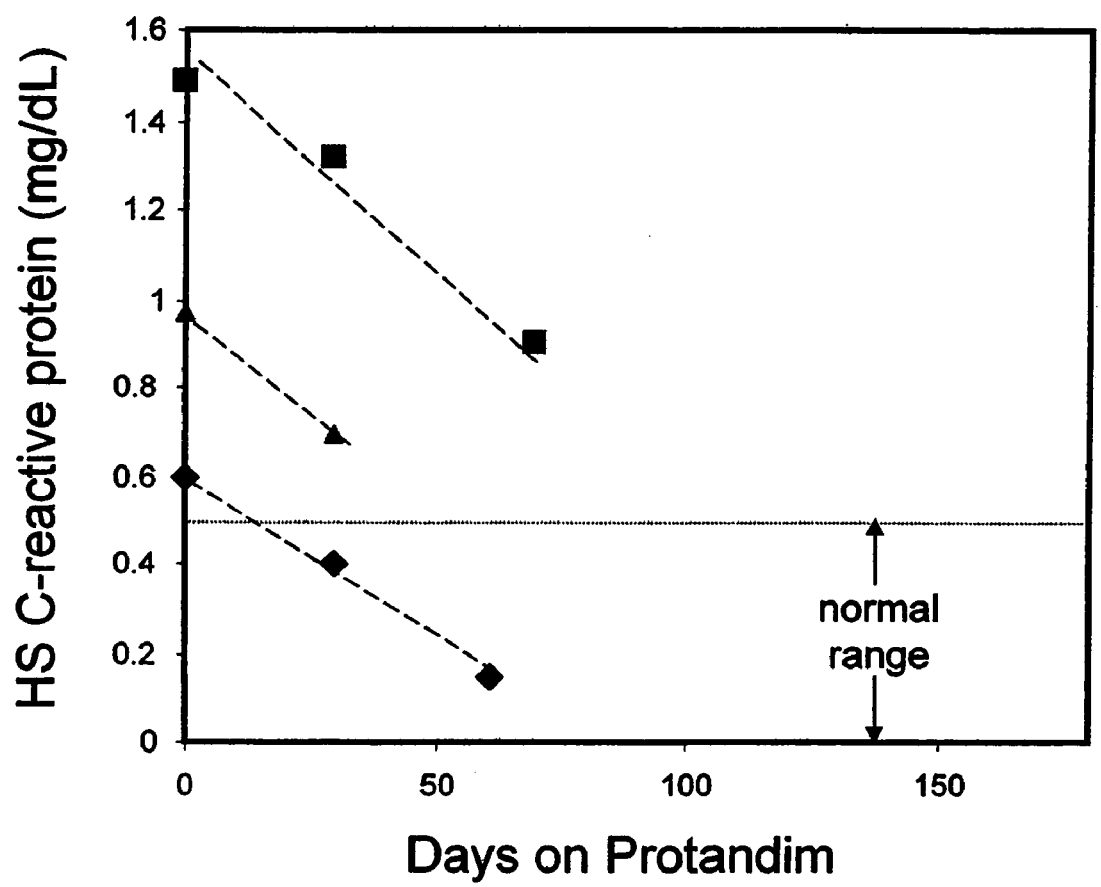
FIG. 18 is a graph illustrating the effect of Protandim II dietary supplementation on human CRP protein level.

Three subjects entered the study with elevated CRP levels, there was a trend towards reduction of these levels with Protandim II supplementation. As shown in FIG. 18, the CRP dropped an average of 24% after 30 days of Protandim II supplementation. The CRP levels continued to decline at 60-70 days, illustrating a decrease of greater than average of 30%-33% decline in CRP levels over the time tested. No significant changes were seen in total cholesterol, LDL, HDL, or triglycerides.

F. Effect of Low-Dose Protandim II (338 mg/day)

Figure 19:
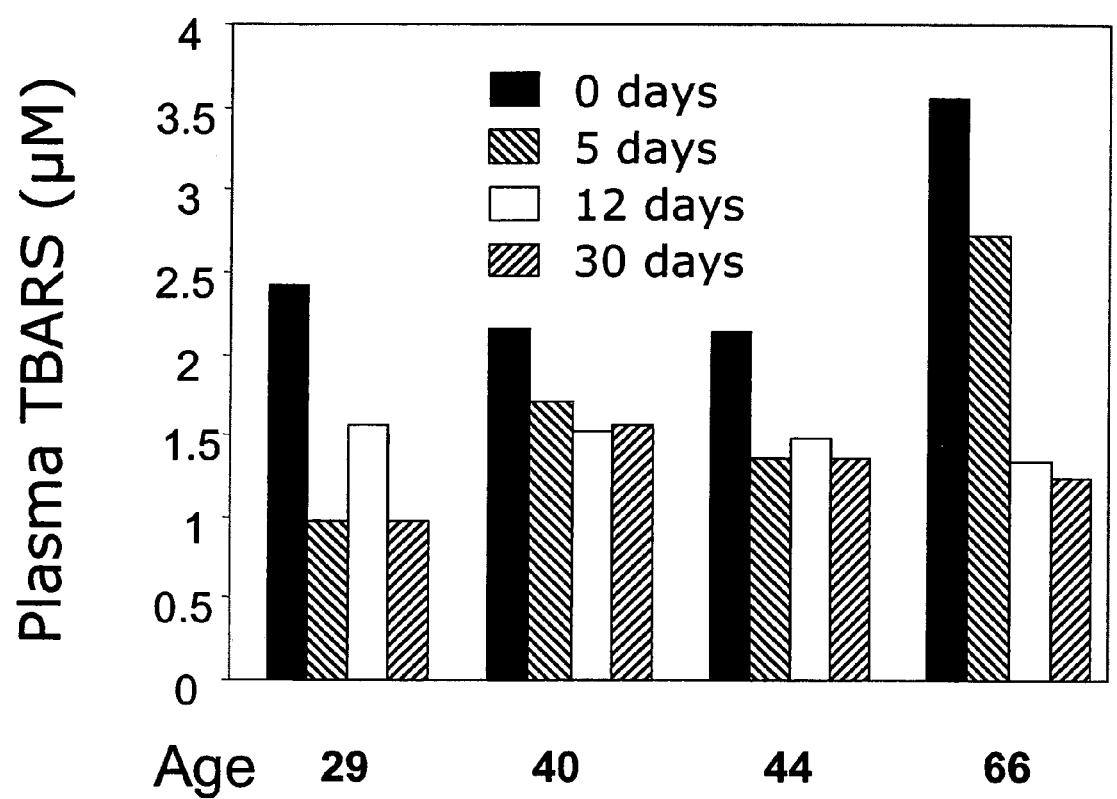
FIG. 19 is a graph illustrating the effect of half-dose Protandim II on plasma TBARS in humans subjects. The half-dose Protandim II was 338 mg/day dietary supplement.
Figure 20:
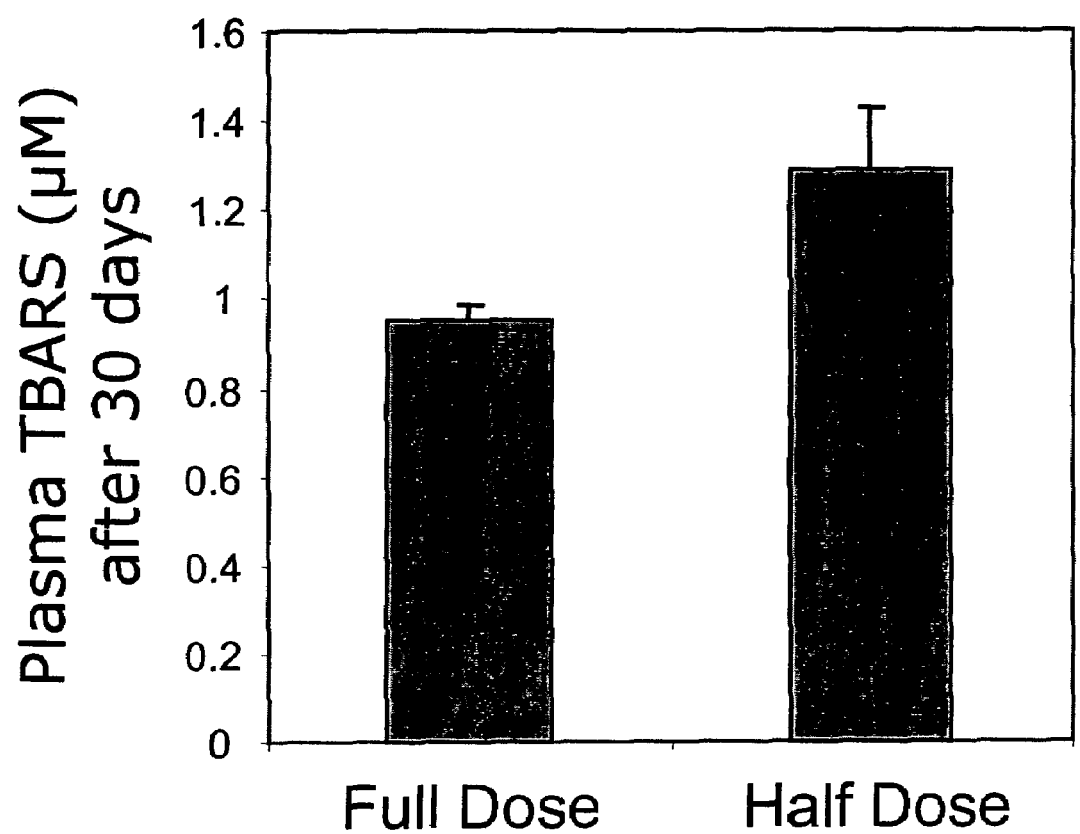
FIG. 20 is a graph comparing the effect of Protandim II dosage on plasma TBARS in human subjects. Average plasma TBARS concentrations are shown after 30 days supplementation of Protandim II at full-dose (675 mg/day; n=11) and half-dose (338 mg/day; n=4). The difference was statistically significant at p<0.03 as determined by one-tailed paired t-test.

To assess whether the suggested human supplement of 675 mg/day might be more than needed to achieve the desired reduction in oxidative stress, four subjects were given a lower dose of 338 mg/day for 30 days. Blood was drawn from these individuals on day 0, 5, 12 and 30 to provide additional information regarding the time required for the reduction in oxidative stress to manifest. FIG. 19 shows that the response of plasma TBARS is fairly rapid, with most of the change occurring by 5 to 12 days. FIG. 20 shows that the lower dose of Protandim II was not quite as effective as the full dose, lowering TBARS to an average value of 1.29±0.14 µM (n=4) versus 0.95±0.04 µM (n=11). Using a one-tailed t-test, this difference was significant at $p<0.03$. This provides reassurance of the appropriateness of the full recommended dose of Protandim of 675 mg/day is not an excessive dose.

IV. Discussion

The present study established that herbal compositions of the present invention, e.g., Protandim II (as defined in Table 5), are a safe and effective way of decreasing oxidative stress in healthy human subjects ranging in age from 20 to 78. The dosage defined (675 mg/kg body weight) seems well-positioned for safety and efficacy. The age-dependent increase in oxidative stress as measured by lipid peroxidation was abolished. There was no evidence that the subjects showing the lowest initial levels of oxidative stress were in any way compromised by the modest elevations of SOD and catalase that were achieved—an outcome considered remote but theoretically possible due to our recognition that there is a bell-shaped dose-response curve to SOD. That is, problems can result from too much SOD as well as from too little. The results from this study suggest that all subjects benefited from the Protandim II-induced elevations of SOD and catalase activities.

The effects of Protandim II may go beyond direct induction of the SOD and/or catalase genes. The antioxidant enzymes form a system of mutual protection: superoxide inactivates both CAT and GPX, while hydrogen peroxide inactivates the cytosolic SOD. McCord, *Free Radical Biol. Med.,* 4:9-14 (1988); Kono et al., *J. Biol. Chem.,* 257:5751-5754 (1982); Blum et al., *Arch. Biochem. Biophys.,* 240:500-508 (1985); Bray et al., *Biochem. J.,* 139:43-48 (1974). Thus, in a system experiencing substantial oxidative stress the entire group of antioxidant enzymes may be subject to partial inactivation by the unscavenged concentrations of superoxide and hydrogen peroxide. If, under these conditions, SOD alone were induced, the concentration of superoxide would decrease, allowing partial recovery of the activities of CAT and GPX as they escape from superoxide-mediated inactivation. Thus, it would appear that all three enzymes were induced. This might be expected only when starting under conditions of substantial oxidative stress. Under normal conditions, there may be little inactivation of CAT and GPX taking place, so the induction of SOD might have less effect on the activities of the other two enzymes. Another factor to consider is that 4-hydroxynonenal, a product of lipid peroxidation, serves to induce the synthesis of GPX. Larini et al., *Free Radic. Res.,* 38:509-516 (2004). If the induction of SOD results in a lowering of the rate of lipid peroxidation, then the concentration of 4-hydroxynonenal would fall and one might expect that less GPX would be synthesized. This, in fact, is what we observed: SOD was induced, lipid peroxidation was inhibited, and GPX activity fell. Other compositions of the invention likely share the same positive health benefits when administered to a subject.

Example 3

Herbal Compositions of the Invention Normalize Blood Pressure in Human Subjects

Hypertension has been recognized as a multi-factorial trait resulting from the effect of a combination of environmental and genetic factors, including excess dietary salt or alcohol intake, stress, age, genetics and family history, obesity, physical inactivity, as well as high saturated fat diet. During the past few years, however, a large amount of information has been collected on the vascular inflammation, indicating that inflammation may involve in the initiation as well as development of hypertension. Evidence from animal models as well as patients, have indicated that hypertension, an established major risk factor for coronary artery disease, has been suggested to exert pro-inflammatory actions through the increased expression of several mediators, including leukocyte adhesion molecules, chemokines, specific growth factors, heat shock proteins, endothelin-1, and angiotensin. Endothelial dysfunction as well as increased serum levels of C-reactive protein are observed in patients with hypertension (see, Li., J., Med Hypotheses. Is hypertension an inflammatory disease? 2005; 64(2):236-240). Assessment of changes in gene expression associated with increased arterial stiffness and gene polymorphisms that increase the risk for vascular stiffening suggests that components of the renin-angiotensin system, matrix metalloproteinases, intracellular signaling, and extracellular matrix components may all be involved in this process. Interventions aimed at these targets may reduce vascular stiffness, lower systolic blood pressure, decrease the prevalence of ISH, and improve outcomes for patients (particularly older patients) with hypertension or other CV conditions (see, Schiffrin E L., Vascular stiffening and arterial compliance: implications for systolic blood pressure. Am J Hypertens. 2004 December; 17(12 Pt 2):39S-48S). The compositions of the present invention thus provide novel therapeutic strategies to decrease the morbidity as well as mortality of hypertension, and alleviated hypertensive target organ damage.

Subject #1 was a 50 year old man whose blood pressure readings prior to administration of a composition of the invention ranged from 140 to 150 systolic over 90 to 100 diastolic. Following daily ingestion of 1500 mg of a composition containing *B. monniera* extract, Milk Thistle extract 70-80%, Ashwagandha powder, Turmeric extract 95%, *Gotu Kola* powder, *Aloe vera* powder, Green tea (98% Polyphenols 45% EGCG), and *Ginko biloba* leaf extract for 14 days, the subjects blood pressure was measured as 126 systolic over 74 diastolic. The approximate daily dosage of each of the components of the herb-containing composition was as follows: *B. monniera* extract (200 mg), Milk Thistle extract 70-80% (300 mg), Ashwagandha powder (200 mg), Turmeric extract (95%) (100 mg), *Gotu Kola* powder (200 mg), Aloe vera powder (200 mg), Green tea (98% Polyphenols 45% EGCG) (100 mg), and Ginko biloba leaf extract (200 mg).

Figure 21:
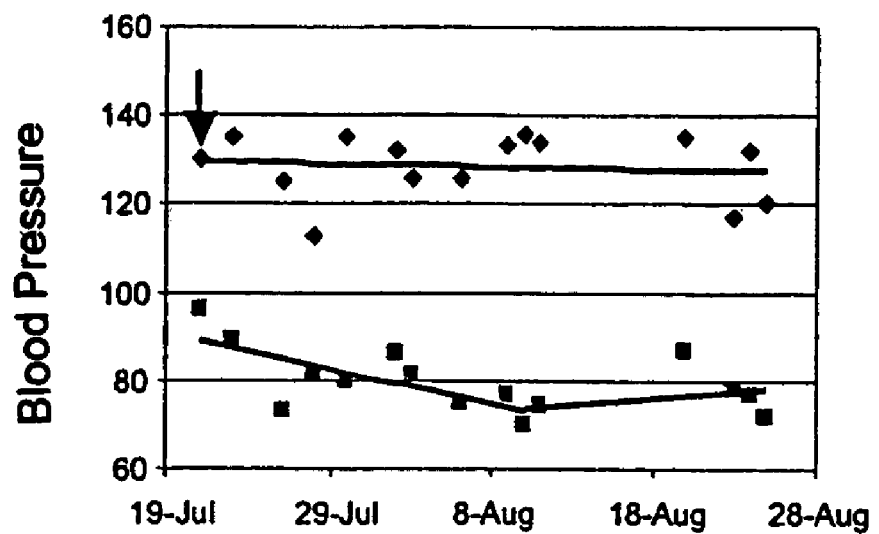
FIG. 21 shows graphs detailing the blood pressure measurements of human subjects administered an herbal composition of the invention. Panel A shows the blood pressure measurements for Subject #2 in Example 2. Panel B shows the blood pressure measurements for Subject #4 in Example 2. The arrow indicates the point in time at which the individual began treatment with an herbal composition of the invention. In both individuals, diastolic blood pressure dropped significantly over a period of about 21 days, remaining constant thereafter.
Figure 21:
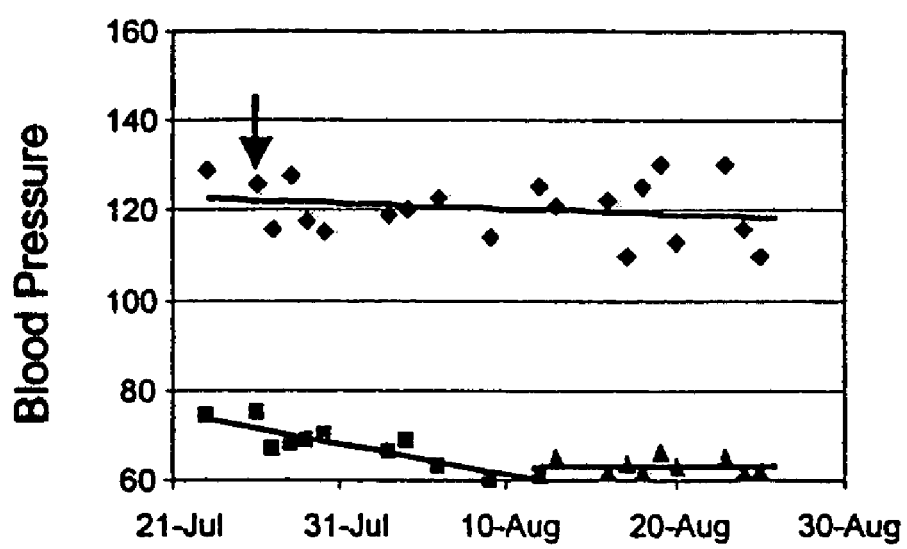

Subject # 2 was a 44 year old woman whose blood pressure readings prior to any treatment were approximately 165 systolic over 113 diastolic to 160 systolic over 103 diastolic. The subject began taking ATENOLOL 25 mg/day (9 months). The ATENOLOL medication reduced the subject's blood pressure to 142 systolic over 98 diastolic to 135 systolic over 96 diastolic, however, the subject's diastolic measurement never got down below 91 (the lowest on ATENOLOL). Following daily ingestion of 1,500 mg of an herb-containing composition containing B. monniera extract, Milk Thistle extract 70-80%, Ashwagandha powder, Turmeric extract 95%, Gotu Kola powder, Aloe vera powder, Green tea (98% Polyphenols 45% EGCG), and Ginko biloba leaf extract for 21 days (while ATENOLOL treatment was continued), the subjects blood pressure was measured as 136 systolic over 70 diastolic. Thus, a drop in diastolic pressure of more than 20 mm was observed during this period (see FIG. 21, panel A). Thereafter, blood pressure remained constant as both treatments continued. The approximate daily dosage of each of the components of the herb-containing composition was as follows: B. monniera extract (200 mg), Milk Thistle extract 70-80% (300 mg), Ashwagandha powder (200 mg), Turmeric extract (95%) (100 mg), Gotu Kola powder (200 mg), Aloe vera powder (200 mg), Green tea (98% Polyphenols 45% EGCG) (100 mg), and Ginko biloba leaf extract (200 mg).

Subject #3 was a 49 year old man whose blood pressure readings prior to administration of a composition of the invention was 135 systolic over 78 diastolic. Following daily ingestion of 1500 mg of a composition containing B. monniera extract, Milk Thistle extract 70-80%, Ashwagandha powder, Turmeric extract 95%, Gotu Kola powder, Aloe vera powder, Green tea (98% Polyphenols 45% EGCG), and Ginko biloba leaf extract for 7 days, the subjects blood pressure was measured as 117 systolic over 75 diastolic. The approximate daily dosage of each of the components of the herb-containing composition was as follows: B. monniera extract (200 mg), Milk Thistle extract 70-80% (300 mg), Ashwagandha powder (200 mg), Turmeric extract (95%) (100 mg), Gotu Kola powder (200 mg), Aloe vera powder (200 mg), Green tea (98% Polyphenols 45% EGCG) (100 mg), and Ginko biloba leaf extract (200 mg).

Subject # 4 was a 59 year old man whose blood pressure readings prior to any treatment were approximately 128 systolic over 75 diastolic. Following daily ingestion of 1000 mg of a composition containing B. monniera extract, Milk Thistle extract 70-80%, Ashwagandha powder, Turmeric extract 95%, Gotu Kola powder, Aloe vera powder, Green tea (98% Polyphenols 45% EGCG), and Ginko biloba leaf extract for 21 days, the subject's blood pressure was measured as 125 systolic over 61 diastolic. Thus, a drop in diastolic pressure of about 14 mm was observed during this period (see FIG. 21, panel B). After 21 days, blood pressure remained constant as treatment continued. The approximate daily dosage of each of the components of the herb-containing composition was as follows: B. monniera extract (134 mg), Milk Thistle extract 70-80% (200 mg), Ashwagandha powder (134 mg), Turmeric extract (95%) (67 mg), Gotu Kola powder (134 mg), Aloe vera powder (134 mg), Green tea (98% Polyphenols, 45% EGCG) (67 mg), and Ginko biloba leaf extract (134 mg).

Example 4

Compositions of the Invention Prevents or Alleviates Migraine Headaches in Human Subjects Migraines afflict about 24 million people in the United States. They may occur at any age, but usually begin between the ages of 10 and 40 and diminish after age 50. Some people experience several migraines a month, while others have only a few migraines throughout their lifetime. Approximately 75% of migraine sufferers are women.

A migraine is a throbbing or pulsating headache that is often one sided (unilateral) and associated with nausea; vomiting; sensitivity to light, sound, and smells; sleep disruption; and depression. Attacks are often recurrent and tend to become less severe as the migraine sufferer ages. Migraines are classified according to the symptoms they produce. The two most common types are migraine with aura and migraine without aura. Less common types include the following: Basilar artery migraine; Carotidynia; Headache-free migraine; Ophthalmoplegic migraine; Status migraine The cause of migraine is unknown. The condition may result from a series of reactions in the central nervous system caused by changes in the body or in the environment. There is often a family history of the disorder, suggesting that migraine sufferers may inherit sensitivity to triggers that produce inflammation in the blood vessels and nerves around the brain, causing pain.

A trigger is any stimulus that initiates a process or reaction. Commonly identified migraine triggers include the following: Alcohol (e.g., red wine); environmental factors (e.g., weather, altitude, time zone changes); foods that contain caffeine (e.g., coffee, chocolate); monosodium glutamate (MSG; found in Chinese food); and nitrates (e.g., processed foods, hot dogs); glare; hormonal changes in women; hunger; lack of sleep, medications (over-the-counter and prescription); perfume; stress.

In the present study, a female subject (woman) who routinely suffers migraine headaches was administered a composition of the invention to assess the affect of the composition on the incidence of her migraine headaches. The subject ingested a composition containing B. monniera extract, Milk Thistle extract 70-80%, Ashwagandha powder, Turmeric extract 95%, Gotu Kola powder, Aloe vera powder, Green tea (98% Polyphenols 45% EGCG), and Ginko biloba leaf extract for 30 days. The approximate daily dosage of each of the components of the herb-containing composition was as follows: B. monniera extract (134 mg-200 mg), Milk Thistle extract 70-80% (200 mg-300 mg), Ashwagandha powder (134 mg-200 mg), Turmeric extract (95%) (67 mg-100 mg), Gotu Kola powder (134 mg-200 mg), Aloe vera powder (134 mg-200 mg), Green tea (98% Polyphenols 45% EGCG) (67 mg-100 mg), and Ginko biloba leaf extract (134 mg-200 mg). Following the initiation of administration of the composition of the invention, the subject has not had a migraine headache. The composition of the invention is therefore useful to prevent or alleviate migraine headaches in a subject.

Similarly, the compositions of the present invention are useful to prevent or treat headaches in a subject associated with high altitude (e.g., acute mountain sickness (AMS)). In the context of a recent ascent, a headache, with any one or more of the following symptoms above 2500 meters (8000 feet) qualifies a subject for the diagnosis of AMS: loss of appetite, nausea, or vomiting; fatigue or weakness; dizziness or light-headedness; difficulty sleeping; confusion; staggering gait. The compositions of the present invention are also useful to prevent or treat headaches, both acute and chronic.

Example 5

Embodiments of the Herb-Containing Composition of the Invention

In one embodiment of the method preventing, alleviating or treating oxidative stress in a subject, an herb-containing composition containing B. monniera extract, Milk Thistle extract, 70-80% Silymarin, Ashwagandha powder, Green tea, 98% polyphenols, 45% EGCG, and Turmeric extract, and 95% Curcumin is administered at least daily to a subject. In one embodiment, the herb-containing composition of the invention contains B. monniera extract, 45% bacosides, Milk Thistle extract, 70-80% Silymarin, Ashwagandha powder, Green tea, 98% polyphenols, 45% EGCG, and turmeric extract, 95% curcumin in concentrations as detailed below in Table 7.

TABLE 7

Composition of Protandim II

| Active Ingredient | Quantity | Weight Percent (wt %) Total Active Ingredients |
|---|---|---|
| Bacopa monniera, extract 45% bacosides | 150 mg | 22.2 |
| Milk Thistle extract, 70-80% silymarin | 225 mg | 33.3 |
| Ashwagandha powder | 150 mg | 22.2 |
| Green tea, 98% polyphenols, 45% EGCG | 75 mg | 11.1 |
| Turmeric extract, 95% curcumin | 75 mg | 11.1 |
| Total | 675 mg | 99.9 |

In one embodiment, the herb-containing composition of the invention contains from about 5 wt % to about 50 wt % B. monniera extract (45% bacosides) of the total weight of active ingredients. In one embodiment, the herb-containing composition of the invention contains from about 10 wt % to about 30 wt % B. monniera extract (45% bacosides) of the total weight of active ingredients. In one embodiment, the herb-containing composition of the invention contains at least about 22 wt % B. monniera extrac (45% bacosides) of the total weight of active ingredients.

In one embodiment, the herb-containing composition of the invention contains from about 5 wt % to about 60 wt % milk thistle extract (70%-80% silymarin) of the total weight of active ingredients. In one embodiment, the herb-containing composition of the invention contains from about 10 wt % to about 50 wt % milk thistle extract (70%-80% silymarin) of the total weight of active ingredients. In one embodiment, the herb-containing composition of the invention contains at least about 33 wt % milk thistle extract (70%-80% silymarin) of the total weight of active ingredients.

In one embodiment, the herb-containing composition of the invention contains from about 5 wt % to about 50 wt % Ashwagandha powder of the total weight of active ingredients. In one embodiment, the herb-containing composition of the invention contains from about 10 wt % to about 30 wt % Ashwagandha extract of the total weight of active ingredients. In one embodiment, the herb-containing composition of the invention contains at least about 22 wt % Ashwagandha extract of the total weight of active ingredients.

In one embodiment, the herb-containing composition of the invention contains from about 2.5 wt % to about 25 wt % turmeric extract (95% curcumin) of the total weight of active ingredients. In one embodiment, the herb-containing composition of the invention contains from about 5 wt % to about 15 wt % turmeric extract (95% curcumin) of the total weight of active ingredients. In one embodiment, the herb-containing composition of the invention contains at least about 11 wt % turmeric extract (95% curcumin) of the total weight of active ingredients.

In one embodiment, the herb-containing composition of the invention contains from about 2.5 wt % to about 25 wt % green tea (98% polyphenols, 45% EGCG) of the total weight of active ingredients. In one embodiment, the herb-containing composition of the invention contains from about 5 wt % to about 15 wt % green tea (98% polyphenols, 45% EGCG) of the total weight of active ingredients. In one embodiment, the herb-containing composition of the invention contains at least about 11 wt % green tea (45% polyphenols) of the total weight of active ingredients.

In some embodiments of the herb-containing composition of the present invention, the composition comprises the active ingredients as summarized above in Table 7 as well as Gotu kola powder, Ginko biloba leaf extract and Aloe vera powder as detailed below in Table 8.

TABLE 8

Composition of Protandim I.

| Active Ingredient | Amount | Percent Weight Total Active Ingredients |
|---|---|---|
| Bacopa monniera extract, 45% bacosides | 150 mg | 12.77 |
| Milk Thistle extract, 70-80% silymarin | 275 mg | 23.4 |
| Ashwagandha powder | 150 mg | 12.77 |
| Gotu kola power | 150 mg | 12.77 |
| Turmeric extract, 95% curcumin | 75 mg | 6.38 |
| Green tea 98% polyphenols, 45% EGCG | 75 mg | 6.38 |
| Ginko biloba leaf extract | 150 mg | 12.77 |
| Aloe vera powder | 150 mg | 12.77 |
| Total | 1175 mg | 100 |

In one embodiment, the herb-containing composition of the invention contains from about 5 wt % to about 50 wt % B. monniera extract (45% bacosides) of the total weight of active ingredients. In one embodiment, the herb-containing composition of the invention contains from about 10 wt % to about 30 wt % B. monniera extract (45% bacosides) of the total weight of active ingredients. In one embodiment, the herb-containing composition of the invention contains at least about 22 wt % B. monniera extract (45% bacosides) of the total weight of active ingredients. In one embodiment, the herb-containing composition of the invention contains at least about 12 wt % B. monniera extract (45% bacosides) of the total weight of active ingredients.

In one embodiment, the herb-containing composition of the invention contains from about 5 wt % to about 60 wt % milk thistle extract (70%-80% silymarin) of the total weight of active ingredients. In one embodiment, the herb-containing composition of the invention contains from about 10 wt % to about 50 wt % milk thistle extract (70%-80% silymarin) of the total weight of active ingredients. In one embodiment, the herb-containing composition of the invention contains at least about 33 wt % milk thistle extract (70%-80% silymarin) of the total weight of active ingredients.

In one embodiment, the herb-containing composition of the invention contains at least about 23 wt % milk thistle extract (70%-80% silymarin) of the total weight of active ingredients.

In one embodiment, the herb-containing composition of the invention contains from about 5 wt % to about 50 wt % Ashwagandha powder of the total weight of active ingredients. In one embodiment, the herb-containing composition of the invention contains from about 10 wt % to about 30 wt % Ashwagandha extract of the total weight of active ingredients. In one embodiment, the herb-containing composition of the invention contains at least about 22 wt % Ashwagandha extract of the total weight of active ingredients. In one embodiment, the herb-containing composition of the invention contains at least about 12 wt % Ashwagandha extract of the total weight of active ingredients.

In one embodiment, the herb-containing composition of the invention contains from about 2.5 wt % to about 25 wt % turmeric extract (95% curcumin) of the total weight of active ingredients. In one embodiment, the herb-containing composition of the invention contains from about 5 wt % to about 15 wt % turmeric extract (95% curcumin) of the total weight of active ingredients. In one embodiment, the herb-containing composition of the invention contains at least about 11 wt % turmeric extract (95% curcumin) of the total weight of active ingredients. In one embodiment, the herb-containing composition of the invention contains at least about 6 wt % turmeric extract (95% curcumin) of the total weight of active ingredients.

In one embodiment, the herb-containing composition of the invention contains from about 2.5 wt % to about 25 wt % green tea (98% polyphenols, 45% EGCG) of the total weight of active ingredients. In one embodiment, the herb-containing composition of the invention contains from about 5 wt % to about 15 wt % green tea (98% polyphenols, 45% EGCG) of the total weight of active ingredients. In one embodiment, the herb-containing composition of the invention contains at least about 11 wt % green tea (45% polyphenols) of the total weight of active ingredients. In one embodiment, the herb-containing composition of the invention contains at least about 6 wt % green tea (45% polyphenols) of the total weight of active ingredients.

In one embodiment the composition, the *Gotu kola* powder is present at a concentration from at least about 5 weight percent to about 50 weight percent of the total dry weight of active ingredients of the composition. In one embodiment of the composition, the *Gotu kola* powder is present at a concentration from at least about 10 weight percent to about 30 weight percent of the total dry weight of active ingredients of the composition. In one embodiment of the composition, the *Gotu kola* powder extract is present at a concentration at least about 12 weight percent of the total dry weight of active ingredients of the composition.

In one embodiment of the composition, the *Ginko biloba* leaf extract is present at a concentration from at least about 5 weight percent to about 50 weight percent of the total dry weight of active ingredients of the composition. In one embodiment of the composition, the *Ginko biloba* leaf extract is present at a concentration from at least about 10 weight percent to about 30 weight percent of the total dry weight of active ingredients of the composition. In one embodiment of the composition, the *Ginko biloba* leaf extract is present at a concentration at least about 12 weight percent of the total dry weight of active ingredients of the composition.

In one embodiment of the composition, the *Aloe vera* powder is present at a concentration from at least about 5 weight percent to about 50 weight percent of the total dry weight of active ingredients of the composition. In one embodiment of the composition, the *Aloe vera* powder is present at a concentration from at least about 10 weight percent to about 30 weight percent of the total dry weight of active ingredients of the composition. In one embodiment of the composition, the *Aloe vera* powder is present at a concentration of at least about 12 weight percent of the total dry weight of active ingredients of the composition.

In some embodiments, the herb-containing compositions of the invention are formulated to contain at least one excipient such as, e.g., calcium carbonate; croscarmellose sodium; dicalcium phosphate; magnesium stearate; microcrystalline cellulose; modified cellulose; silica; and stearic acid.

EQUIVALENTS

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

We claim:

1. A composition comprising: (a) at least about 150 milligrams Bacopa monniera extract, wherein said Bacopa monniera extract is comprised of 45 percent bacosides; at least about 225 milligrams silybum marianum (milk thistle) extract, wherein said milk thistle extract is comprised of between about 70 percent and about 80 percent silymarin; at least about 150 mg Withania somnifera (ashwagandha) powder; at least about 75 milligrams Camellia sinensis (green tea extract); wherein said green tea extract is comprised of 98 percent polyphenols; said polyphenols comprised of 45 percent (−)-epigallocatechin gallate; at least about 75 milligrams Curcuma longa (turmeric) extract; wherein said turmeric extract is comprised of 95 percent curcumin; wherein the composition increases the enzyme activity level of at least one antioxidant enzyme selected from the group consisting of: superoxide dismutase and catalase and decreases the plasma concentration level of thiobarbituric acid reactive chemical species, when administered in an effective amount to a mammalian subject in need thereof.

2. The composition according to claim 1, wherein the composition is formulated as an oral dosage form.

3. The composition according to claim 2, wherein the oral dosage form is selected from the group consisting of: a tablet; capsule; and caplet.

* * * * *